(12) United States Patent
Ma

(10) Patent No.: US 11,655,497 B2
(45) Date of Patent: May 23, 2023

(54) METHOD OF AMPLIFYING A TARGET NUCLEIC ACID

(71) Applicant: NINGBO SHINING BIOTECHNOLOGY CO., LTD, Zhejiang (CN)

(72) Inventor: Zhaochun Ma, Sunnyvale, CA (US)

(73) Assignee: NINGBO SHINING BIOTECHNOLOGY CO., LTD, Zhejiang (CN)

( * ) Notice: Subject to any disclaimer, the term of this patent is extended or adjusted under 35 U.S.C. 154(b) by 158 days.

(21) Appl. No.: 16/649,659

(22) PCT Filed: Sep. 19, 2018

(86) PCT No.: PCT/CN2018/106436
§ 371 (c)(1),
(2) Date: Mar. 22, 2020

(87) PCT Pub. No.: WO2019/062614
PCT Pub. Date: Apr. 4, 2019

(65) Prior Publication Data
US 2021/0189477 A1    Jun. 24, 2021

(30) Foreign Application Priority Data

Sep. 26, 2017   (WO) ................ PCT/CN2017/103393

(51) Int. Cl.
*C12Q 1/68* (2018.01)
*C12Q 1/6853* (2018.01)
*C12Q 1/6811* (2018.01)
*C12Q 1/6876* (2018.01)

(52) U.S. Cl.
CPC .......... *C12Q 1/6853* (2013.01); *C12Q 1/6811* (2013.01); *C12Q 1/6876* (2013.01)

(58) Field of Classification Search
None
See application file for complete search history.

(56) References Cited

U.S. PATENT DOCUMENTS

| | | | |
|---|---|---|---|
| 6,534,269 B2 | 3/2003 | Liu et al. | |
| 7,238,480 B2 | 7/2007 | Liu et al. | |
| 2004/0175733 A1* | 9/2004 | Andersen | C12Q 1/6827 435/6.11 |
| 2014/0329245 A1* | 11/2014 | Spier | C12Q 1/6848 435/6.12 |

FOREIGN PATENT DOCUMENTS

| | | |
|---|---|---|
| CN | 103266103 A | 8/2013 |
| CN | 105368924 A | 3/2016 |
| CN | 106811537 A | 6/2017 |
| CN | 106987622 A | 7/2017 |
| WO | 2015073931 A1 | 5/2015 |

OTHER PUBLICATIONS

International Search Report of PCT Application No. PCT/CN2018/106436, dated Dec. 26, 2018.
Ku, C.-S. et al., "A new era in the discovery of de novo mutations underlying human genetic disease", Human Genomics (2012), vol. 6, p. 27.
Chiu, R. W. K. et al., "Noninvasive prenatal diagnosis empowered by high-throughput sequencing", Prenatal Diagnosis (2012), vol. 32, pp. 401-406.
Helleday, T. et al., "Mechanisms underlying mutational signatures in human cancers", Nature Reviews Genetics (Sep. 2014), vol. 15(9), pp. 585-598. doi:10.1038/nrg3729.
Veltman, J. A. et al., "De novo mutations in human genetic disease", Nature Reviews Genetics (Aug. 2012), vol. 13, pp. 565-575.

* cited by examiner

*Primary Examiner* — Suryaprabha Chunduru
(74) *Attorney, Agent, or Firm* — Jun He Law Offices P.C.; Zhaohui Wang

(57) ABSTRACT

The present disclosure provides a method of amplifying a target nucleic acid, wherein the method comprises: (a) providing a reaction mixture comprising: (i) a nucleic acid sample comprising or suspected of comprising the target nucleic acid, (ii) multiple primer pairs, wherein at least one primer of each type of primer pairs is complementary to a portion of the target nucleic acid, and each primer pair has at least one blocking primer comprising a blocking group capable of blocking polymerase extension, (iii) nucleic acid polymerase, and (iv) de-blocking agent capable of enabling polymerization of the target nucleic acid by said nucleic acid polymerase using the blocking primers; and (b) incubating the reaction mixture under a condition for amplification of the target nucleic acid and a kit used for the method. The present disclosure further provides a method of sequencing a target nucleic acid and a kit used for the method.

17 Claims, 15 Drawing Sheets
Specification includes a Sequence Listing.

Figure 3. NGS library construction for fragmented DNA with single strand molecular index tag Figure 4. NGS library construction for fragmented DNA with double strand molecular index tag Figure 8. Mutant enriched NGS library construction for fragmented DNA with double strand molecular index tag

SEQUENCE LISTING

<160> NUMBER OF SEQ ID NOS: 437

<210> SEQ ID NO 1
<211> LENGTH: 57
<212> TYPE: DNA
<213> ORGANISM: Artificial Sequence
<220> FEATURE:
<223> OTHER INFORMATION: Synthetic

<400> SEQUENCE: 1
acactctttc cctacacgac gctcttccga tctaaaacaa gctctcatgt ctgaact        57

<210> SEQ ID NO 2
<211> LENGTH: 58
<212> TYPE: DNA
<213> ORGANISM: Artificial Sequence
<220> FEATURE:
<223> OTHER INFORMATION: Synthetic

<400> SEQUENCE: 2
gtgactggag ttcagacgtg tgctcttccg atctcatgtg gttgtgaaaa ctgttcaa       58

<210> SEQ ID NO 3
<211> LENGTH: 53
<212> TYPE: DNA

<213> ORGANISM: Artificial Sequence
<220> FEATURE:
<223> OTHER INFORMATION: Synthetic

<400> SEQUENCE: 3
acactctttc cctacacgac gctcttccga tctcatggtt actgcctctg gtg        53

<210> SEQ ID NO 4
<211> LENGTH: 52
<212> TYPE: DNA
<213> ORGANISM: Artificial Sequence
<220> FEATURE:
<223> OTHER INFORMATION: Synthetic

<400> SEQUENCE: 4
gtgactggag ttcagacgtg tgctcttccg atctcaccag cgtgtccagg aa          52

<210> SEQ ID NO 5
<211> LENGTH: 52
<212> TYPE: DNA
<213> ORGANISM: Artificial Sequence
<220> FEATURE:
<223> OTHER INFORMATION: Synthetic

<400> SEQUENCE: 5
acactctttc cctacacgac gctcttccga tctacatgga gatcgatggg ca          52

<210> SEQ ID NO 6
<211> LENGTH: 52
<212> TYPE: DNA
<213> ORGANISM: Artificial Sequence
<220> FEATURE:
<223> OTHER INFORMATION: Synthetic

<400> SEQUENCE: 6
gtgactggag ttcagacgtg tgctcttccg atctgctgcc tgtcaggcag at          52

<210> SEQ ID NO 7
<211> LENGTH: 51
<212> TYPE: DNA
<213> ORGANISM: Artificial Sequence
<220> FEATURE:
<223> OTHER INFORMATION: Synthetic

<400> SEQUENCE: 7
acactctttc cctacacgac gctcttccga tctcbgaggt cactcacctg g           51

<210> SEQ ID NO 8
<211> LENGTH: 59
<212> TYPE: DNA
<213> ORGANISM: Artificial Sequence
<220> FEATURE:
<223> OTHER INFORMATION: Synthetic

<400> SEQUENCE: 8
gtgactggag ttcagacgtg tgctcttccg atctggggag aagtaagtat atacacagt   59

<210> SEQ ID NO 9
<211> LENGTH: 61
<212> TYPE: DNA
<213> ORGANISM: Artificial Sequence
<220> FEATURE:
<223> OTHER INFORMATION: Synthetic

<400> SEQUENCE: 9
acactctttc cctacacgac gctcttccga tctagaacaa aaccatgtaa taaaattctg  60
a                                                              61

<210> SEQ ID NO 10
<211> LENGTH: 60
<212> TYPE: DNA
<213> ORGANISM: Artificial Sequence
<220> FEATURE:
<223> OTHER INFORMATION: Synthetic

<400> SEQUENCE: 10
gtgactggag ttcagacgtg tgctcttccg atctattgta acagcataca aggatcttcc    60

<210> SEQ ID NO 11
<211> LENGTH: 61
<212> TYPE: DNA
<213> ORGANISM: Artificial Sequence
<220> FEATURE:
<223> OTHER INFORMATION: Synthetic

<400> SEQUENCE: 11
acactctttc cctacacgac gctcttccga tctttcattt gttttcccct ttaaacaatt    60
a                                                              61

<210> SEQ ID NO 12
<211> LENGTH: 62
<212> TYPE: DNA
<213> ORGANISM: Artificial Sequence
<220> FEATURE:
<223> OTHER INFORMATION: Synthetic

<400> SEQUENCE: 12
gtgactggag ttcagacgtg tgctcttccg atctgagtaa tggtaggtaa tctgtttctt    60
ac                                                             62

<210> SEQ ID NO 13
<211> LENGTH: 52
<212> TYPE: DNA
<213> ORGANISM: Artificial Sequence
<220> FEATURE:
<223> OTHER INFORMATION: Synthetic

<400> SEQUENCE: 13
acactctttc cctacacgac gctcttccga tcttgagggt accagagaca gt             52

<210> SEQ ID NO 14
<211> LENGTH: 62
<212> TYPE: DNA
<213> ORGANISM: Artificial Sequence
<220> FEATURE:
<223> OTHER INFORMATION: Synthetic

<400> SEQUENCE: 14
gtgactggag ttcagacgtg tgctcttccg atctaatttt tatgtacttt tcattccctg    60
aa                                                             62

<210> SEQ ID NO 15
<211> LENGTH: 61
<212> TYPE: DNA
<213> ORGANISM: Artificial Sequence
<220> FEATURE:
<223> OTHER INFORMATION: Synthetic

<400> SEQUENCE: 15
acactctttc cctacacgac gctcttccga tctytgttat ttagtttga aacacagaga    60 a    61

<210> SEQ ID NO 16
<211> LENGTH: 56
<212> TYPE: DNA
<213> ORGANISM: Artificial Sequence
<220> FEATURE:
<223> OTHER INFORMATION: Synthetic

<400> SEQUENCE: 16
gtgactggag ttcagacgtg tgctcttccg atctctccac acactccagt taggta    56

<210> SEQ ID NO 17
<211> LENGTH: 60
<212> TYPE: DNA
<213> ORGANISM: Artificial Sequence
<220> FEATURE:
<223> OTHER INFORMATION: Synthetic

<400> SEQUENCE: 17
acactctttc cctacacgac gctcttccga tcttctatgc aagatacaca gtaaaggttc    60

<210> SEQ ID NO 18
<211> LENGTH: 54
<212> TYPE: DNA
<213> ORGANISM: Artificial Sequence
<220> FEATURE:
<223> OTHER INFORMATION: Synthetic

<400> SEQUENCE: 18
gtgactggag ttcagacgtg tgctcttccg atctgtgcac tgaaagagga tcgt    54

<210> SEQ ID NO 19
<211> LENGTH: 55
<212> TYPE: DNA
<213> ORGANISM: Artificial Sequence
<220> FEATURE:
<223> OTHER INFORMATION: Synthetic

<400> SEQUENCE: 19
acactctttc cctacacgac gctcttccga tctctctgac aagagcatgc catag    55

<210> SEQ ID NO 20
<211> LENGTH: 56
<212> TYPE: DNA
<213> ORGANISM: Artificial Sequence
<220> FEATURE:
<223> OTHER INFORMATION: Synthetic

<400> SEQUENCE: 20
gtgactggag ttcagacgtg tgctcttccg atctcgtttc agatccacag ggattg    56

<210> SEQ ID NO 21
<211> LENGTH: 51
<212> TYPE: DNA
<213> ORGANISM: Artificial Sequence
<220> FEATURE:
<223> OTHER INFORMATION: Synthetic

<400> SEQUENCE: 21
acactctttc cctacacgac gctcttccga tctccacctg attgcatgcc a    51

<210> SEQ ID NO 22
<211> LENGTH: 52

<212> TYPE: DNA
<213> ORGANISM: Artificial Sequence
<220> FEATURE:
<223> OTHER INFORMATION: Synthetic

<400> SEQUENCE: 22
gtgactggag ttcagacgtg tgctcttccg atctggcact tctccagccc aa         52

<210> SEQ ID NO 23
<211> LENGTH: 54
<212> TYPE: DNA
<213> ORGANISM: Artificial Sequence
<220> FEATURE:
<223> OTHER INFORMATION: Synthetic

<400> SEQUENCE: 23
acactctttc cctacacgac gctcttccga tcttgacraa gaacagctca aagc       54

<210> SEQ ID NO 24
<211> LENGTH: 56
<212> TYPE: DNA
<213> ORGANISM: Artificial Sequence
<220> FEATURE:
<223> OTHER INFORMATION: Synthetic

<400> SEQUENCE: 24
gtgactggag ttcagacgtg tgctcttccg atctactgaa tttggctgat ctcagc     56

<210> SEQ ID NO 25
<211> LENGTH: 57
<212> TYPE: DNA
<213> ORGANISM: Artificial Sequence
<220> FEATURE:
<223> OTHER INFORMATION: Synthetic

<400> SEQUENCE: 25
acactctttc cctacacgac gctcttccga tctatgtcta tgaagtgttg tggttcc    57

<210> SEQ ID NO 26
<211> LENGTH: 62
<212> TYPE: DNA
<213> ORGANISM: Artificial Sequence
<220> FEATURE:
<223> OTHER INFORMATION: Synthetic

<400> SEQUENCE: 26
gtgactggag ttcagacgtg tgctcttccg atctaaaatt ttccgtctta tttcatttct 60
gt                                                                62

<210> SEQ ID NO 27
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (38)..(38)
<223> OTHER INFORMATION: n is a, c, g, or t

<400> SEQUENCE: 27
acactctttc cctacacgac gctcttccga tctggtcnga ttccagttaa atgg       54

<210> SEQ ID NO 28
<211> LENGTH: 57
<212> TYPE: DNA

```
<213> ORGANISM: Artificial Sequence
<220> FEATURE:
<223> OTHER INFORMATION: Synthetic

<400> SEQUENCE: 28
gtgactggag ttcagacgtg tgctcttccg atctacgcaa agtgatgtgt aagtgtg          57

<210> SEQ ID NO 29
<211> LENGTH: 51
<212> TYPE: DNA
<213> ORGANISM: Artificial Sequence
<220> FEATURE:
<223> OTHER INFORMATION: Synthetic

<400> SEQUENCE: 29
acactctttc cctacacgac gctcttccga tctaccctgc ttgcaggatg g                51

<210> SEQ ID NO 30
<211> LENGTH: 56
<212> TYPE: DNA
<213> ORGANISM: Artificial Sequence
<220> FEATURE:
<223> OTHER INFORMATION: Synthetic

<400> SEQUENCE: 30
gtgactggag ttcagacgtg tgctcttccg atctccagtg atgggttgta aacctc           56

<210> SEQ ID NO 31
<211> LENGTH: 55
<212> TYPE: DNA
<213> ORGANISM: Artificial Sequence
<220> FEATURE:
<223> OTHER INFORMATION: Synthetic

<400> SEQUENCE: 31
acactctttc cctacacgac gctcttccga tctattttcg tggaagtggg ttacc            55

<210> SEQ ID NO 32
<211> LENGTH: 52
<212> TYPE: DNA
<213> ORGANISM: Artificial Sequence
<220> FEATURE:
<223> OTHER INFORMATION: Synthetic

<400> SEQUENCE: 32
gtgactggag ttcagacgtg tgctcttccg atctgcttcc cagctgggtc at               52

<210> SEQ ID NO 33
<211> LENGTH: 61
<212> TYPE: DNA
<213> ORGANISM: Artificial Sequence
<220> FEATURE:
<223> OTHER INFORMATION: Synthetic

<400> SEQUENCE: 33
acactctttc cctacacgac gctcttccga tcttgtggtt ttaatttcat catgtttcat       60
a                                                                       61

<210> SEQ ID NO 34
<211> LENGTH: 58
<212> TYPE: DNA
<213> ORGANISM: Artificial Sequence
<220> FEATURE:
<223> OTHER INFORMATION: Synthetic

<400> SEQUENCE: 34
```
gtgactggag ttcagacgtg tgctcttccg atctactgca gcagatatgt aagcaaaa        58

<210> SEQ ID NO 35
<211> LENGTH: 57
<212> TYPE: DNA
<213> ORGANISM: Artificial Sequence
<220> FEATURE:
<223> OTHER INFORMATION: Synthetic

<400> SEQUENCE: 35
acactctttc cctacacgac gctcttccga tctaagtagt gataaggtct atgccca         57

<210> SEQ ID NO 36
<211> LENGTH: 58
<212> TYPE: DNA
<213> ORGANISM: Artificial Sequence
<220> FEATURE:
<223> OTHER INFORMATION: Synthetic

<400> SEQUENCE: 36
gtgactggag ttcagacgtg tgctcttccg atctagacag atatttctag tggcaggg        58

<210> SEQ ID NO 37
<211> LENGTH: 54
<212> TYPE: DNA
<213> ORGANISM: Artificial Sequence
<220> FEATURE:
<223> OTHER INFORMATION: Synthetic

<400> SEQUENCE: 37
acactctttc cctacacgac gctcttccga tctcctgttc acaatgagct tgca            54

<210> SEQ ID NO 38
<211> LENGTH: 62
<212> TYPE: DNA
<213> ORGANISM: Artificial Sequence
<220> FEATURE:
<223> OTHER INFORMATION: Synthetic

<400> SEQUENCE: 38
gtgactggag ttcagacgtg tgctcttccg atcttttcct gtatttagat tgatttagtg      60
gt                                                                    62

<210> SEQ ID NO 39
<211> LENGTH: 53
<212> TYPE: DNA
<213> ORGANISM: Artificial Sequence
<220> FEATURE:
<223> OTHER INFORMATION: Synthetic

<400> SEQUENCE: 39
acactctttc cctacacgac gctcttccga tcttcgacac ccgattcaaa gtg             53

<210> SEQ ID NO 40
<211> LENGTH: 57
<212> TYPE: DNA
<213> ORGANISM: Artificial Sequence
<220> FEATURE:
<223> OTHER INFORMATION: Synthetic

<400> SEQUENCE: 40
gtgactggag ttcagacgtg tgctcttccg atctggtttc ataacccaca gatccat         57

<210> SEQ ID NO 41

<211> LENGTH: 55
<212> TYPE: DNA
<213> ORGANISM: Artificial Sequence
<220> FEATURE:
<223> OTHER INFORMATION: Synthetic

<400> SEQUENCE: 41
acactctttc cctacacgac gctcttccga tcttgcyttc tggctggatt taaat         55

<210> SEQ ID NO 42
<211> LENGTH: 62
<212> TYPE: DNA
<213> ORGANISM: Artificial Sequence
<220> FEATURE:
<223> OTHER INFORMATION: Synthetic

<400> SEQUENCE: 42
gtgactggag ttcagacgtg tgctcttccg atctttttg gtttttaaaa ttaatgttgg     60
ca                                                                  62

<210> SEQ ID NO 43
<211> LENGTH: 55
<212> TYPE: DNA
<213> ORGANISM: Artificial Sequence
<220> FEATURE:
<223> OTHER INFORMATION: Synthetic

<400> SEQUENCE: 43
acactctttc cctacacgac gctcttccga tctgcrtgca gataatgaca aggaa         55

<210> SEQ ID NO 44
<211> LENGTH: 58
<212> TYPE: DNA
<213> ORGANISM: Artificial Sequence
<220> FEATURE:
<223> OTHER INFORMATION: Synthetic

<400> SEQUENCE: 44
gtgactggag ttcagacgtg tgctcttccg atcttgactt gtatgtatgt gatgtgtg     58

<210> SEQ ID NO 45
<211> LENGTH: 54
<212> TYPE: DNA
<213> ORGANISM: Artificial Sequence
<220> FEATURE:
<223> OTHER INFORMATION: Synthetic

<400> SEQUENCE: 45
acactctttc cctacacgac gctcttccga tctcgccaca gagaagttgt tgag          54

<210> SEQ ID NO 46
<211> LENGTH: 52
<212> TYPE: DNA
<213> ORGANISM: Artificial Sequence
<220> FEATURE:
<223> OTHER INFORMATION: Synthetic

<400> SEQUENCE: 46
gtgactggag ttcagacgtg tgctcttccg atctgtgaga gccacgcaca ct            52

<210> SEQ ID NO 47
<211> LENGTH: 51
<212> TYPE: DNA
<213> ORGANISM: Artificial Sequence
<220> FEATURE:
<223> OTHER INFORMATION: Synthetic

<400> SEQUENCE: 47
acactctttc cctacacgac gctcttccga tctgccoctg agcgtcatct g    51

<210> SEQ ID NO 48
<211> LENGTH: 53
<212> TYPE: DNA
<213> ORGANISM: Artificial Sequence
<220> FEATURE:
<223> OTHER INFORMATION: Synthetic

<400> SEQUENCE: 48
gtgactggag ttcagacgtg tgctcttccg atctgagttc cactgcaagg tgt    53

<210> SEQ ID NO 49
<211> LENGTH: 54
<212> TYPE: DNA
<213> ORGANISM: Artificial Sequence
<220> FEATURE:
<223> OTHER INFORMATION: Synthetic

<400> SEQUENCE: 49
acactctttc cctacacgac gctcttccga tctctctgtg ctgcatttca gaga    54

<210> SEQ ID NO 50
<211> LENGTH: 54
<212> TYPE: DNA
<213> ORGANISM: Artificial Sequence
<220> FEATURE:
<223> OTHER INFORMATION: Synthetic

<400> SEQUENCE: 50
gtgactggag ttcagacgtg tgctcttccg atctccaccc acatgtcatc aaat    54

<210> SEQ ID NO 51
<211> LENGTH: 59
<212> TYPE: DNA
<213> ORGANISM: Artificial Sequence
<220> FEATURE:
<223> OTHER INFORMATION: Synthetic

<400> SEQUENCE: 51
acactctttc cctacacgac gctcttccga tctgatgaga aaytctcagg aaactctgt    59

<210> SEQ ID NO 52
<211> LENGTH: 56
<212> TYPE: DNA
<213> ORGANISM: Artificial Sequence
<220> FEATURE:
<223> OTHER INFORMATION: Synthetic

<400> SEQUENCE: 52
gtgactggag ttcagacgtg tgctcttccg atcttcagga agtcactgat gtgaag    56

<210> SEQ ID NO 53
<211> LENGTH: 61
<212> TYPE: DNA
<213> ORGANISM: Artificial Sequence
<220> FEATURE:
<223> OTHER INFORMATION: Synthetic

<400> SEQUENCE: 53
acactctttc cctacacgac gctcttccga tctttccatt cttaccaaac tctaaatttt    60
c    61

<210> SEQ ID NO 54
<211> LENGTH: 58
<212> TYPE: DNA
<213> ORGANISM: Artificial Sequence
<220> FEATURE:
<223> OTHER INFORMATION: Synthetic

<400> SEQUENCE: 54
gtgactggag ttcagacgtg tgctcttccg atctacctaa attgcttcag agatgaaa            58

<210> SEQ ID NO 55
<211> LENGTH: 60
<212> TYPE: DNA
<213> ORGANISM: Artificial Sequence
<220> FEATURE:
<223> OTHER INFORMATION: Synthetic

<400> SEQUENCE: 55
acactctttc cctacacgac gctcttccga tctgcagaaa acagatctgt atttatttca          60

<210> SEQ ID NO 56
<211> LENGTH: 57
<212> TYPE: DNA
<213> ORGANISM: Artificial Sequence
<220> FEATURE:
<223> OTHER INFORMATION: Synthetic

<400> SEQUENCE: 56
gtgactggag ttcagacgtg tgctcttccg atctttccta ctaggaccat aggtaca             57

<210> SEQ ID NO 57
<211> LENGTH: 51
<212> TYPE: DNA
<213> ORGANISM: Artificial Sequence
<220> FEATURE:
<223> OTHER INFORMATION: Synthetic

<400> SEQUENCE: 57
acactctttc cctacacgac gctcttccga tctctgcccg caggtacttc t                   51

<210> SEQ ID NO 58
<211> LENGTH: 56
<212> TYPE: DNA
<213> ORGANISM: Artificial Sequence
<220> FEATURE:
<223> OTHER INFORMATION: Synthetic

<400> SEQUENCE: 58
gtgactggag ttcagacgtg tgctcttccg atctcattgt gcacaaggac atcaag              56

<210> SEQ ID NO 59
<211> LENGTH: 54
<212> TYPE: DNA
<213> ORGANISM: Artificial Sequence
<220> FEATURE:
<223> OTHER INFORMATION: Synthetic

<400> SEQUENCE: 59
acactctttc cctacacgac gctcttccga tcttgggtat ccatccgaga aaca                54

<210> SEQ ID NO 60
<211> LENGTH: 59
<212> TYPE: DNA
<213> ORGANISM: Artificial Sequence
<220> FEATURE:
<223> OTHER INFORMATION: Synthetic

```
<400> SEQUENCE: 60
gtgactggag ttcagacgtg tgctcttccg atcttagaaa agaacgtgtg aaataagct      59

<210> SEQ ID NO 61
<211> LENGTH: 54
<212> TYPE: DNA
<213> ORGANISM: Artificial Sequence
<220> FEATURE:
<223> OTHER INFORMATION: Synthetic

<400> SEQUENCE: 61
acactctttc cctacacgac gctcttccga tctgcaacaa gcccactgtc tatg           54

<210> SEQ ID NO 62
<211> LENGTH: 56
<212> TYPE: DNA
<213> ORGANISM: Artificial Sequence
<220> FEATURE:
<223> OTHER INFORMATION: Synthetic

<400> SEQUENCE: 62
gtgactggag ttcagacgtg tgctcttccg atctgaagaa atacagcctg acgtg          56

<210> SEQ ID NO 63
<211> LENGTH: 54
<212> TYPE: DNA
<213> ORGANISM: Artificial Sequence
<220> FEATURE:
<223> OTHER INFORMATION: Synthetic

<400> SEQUENCE: 63
acactctttc cctacacgac gctcttccga tctcccaggt catcttctgc aatc           54

<210> SEQ ID NO 64
<211> LENGTH: 52
<212> TYPE: DNA
<213> ORGANISM: Artificial Sequence
<220> FEATURE:
<223> OTHER INFORMATION: Synthetic

<400> SEQUENCE: 64
gtgactggag ttcagacgtg tgctcttccg atctcgcatc cacagctacc ga             52

<210> SEQ ID NO 65
<211> LENGTH: 57
<212> TYPE: DNA
<213> ORGANISM: Artificial Sequence
<220> FEATURE:
<223> OTHER INFORMATION: Synthetic

<400> SEQUENCE: 65
acactctttc cctacacgac gctcttccga tctaaagatc accttcagaa gtcacag        57

<210> SEQ ID NO 66
<211> LENGTH: 61
<212> TYPE: DNA
<213> ORGANISM: Artificial Sequence
<220> FEATURE:
<223> OTHER INFORMATION: Synthetic

<400> SEQUENCE: 66
gtgactggag ttcagacgtg tgctcttccg atcttgttac catttctca ttcagtgtca      60 t                                                                     61
```

<210> SEQ ID NO 67
<211> LENGTH: 57
<212> TYPE: DNA
<213> ORGANISM: Artificial Sequence
<220> FEATURE:
<223> OTHER INFORMATION: Synthetic

<400> SEQUENCE: 67
acactctttc cctacacgac gctcttccga tctattttat ttcctccctg gaagtcc    57

<210> SEQ ID NO 68
<211> LENGTH: 61
<212> TYPE: DNA
<213> ORGANISM: Artificial Sequence
<220> FEATURE:
<223> OTHER INFORMATION: Synthetic

<400> SEQUENCE: 68
gtgactggag ttcagacgtg tgctcttccg atctgtcaag agtaaggaaa agattcagac    60
t    61

<210> SEQ ID NO 69
<211> LENGTH: 52
<212> TYPE: DNA
<213> ORGANISM: Artificial Sequence
<220> FEATURE:
<223> OTHER INFORMATION: Synthetic

<400> SEQUENCE: 69
acactctttc cctacacgac gctcttccga tcttcaccat cctgtgtgca gg    52

<210> SEQ ID NO 70
<211> LENGTH: 54
<212> TYPE: DNA
<213> ORGANISM: Artificial Sequence
<220> FEATURE:
<223> OTHER INFORMATION: Synthetic

<400> SEQUENCE: 70
gtgactggag ttcagacgtg tgctcttccg atcttctcca tctctgacac caga    54

<210> SEQ ID NO 71
<211> LENGTH: 56
<212> TYPE: DNA
<213> ORGANISM: Artificial Sequence
<220> FEATURE:
<223> OTHER INFORMATION: Synthetic

<400> SEQUENCE: 71
acactctttc cctacacgac gctcttccga tctcatgtat tggtctctca tggcac    56

<210> SEQ ID NO 72
<211> LENGTH: 61
<212> TYPE: DNA
<213> ORGANISM: Artificial Sequence
<220> FEATURE:
<223> OTHER INFORMATION: Synthetic

<400> SEQUENCE: 72
gtgactggag ttcagacgtg tgctcttccg atctttcaat ttttattaaa aaccacaggg    60
a    61

<210> SEQ ID NO 73
<211> LENGTH: 59

<212> TYPE: DNA
<213> ORGANISM: Artificial Sequence
<220> FEATURE:
<223> OTHER INFORMATION: Synthetic

<400> SEQUENCE: 73
acactctttc cctacacgac gctcttccga tctaccagtg actagaaaga tcaaattcc        59

<210> SEQ ID NO 74
<211> LENGTH: 58
<212> TYPE: DNA
<213> ORGANISM: Artificial Sequence
<220> FEATURE:
<223> OTHER INFORMATION: Synthetic

<400> SEQUENCE: 74
gtgactggag ttcagacgtg tgctcttccg atctagaaac aagactcaga gttagggg         58

<210> SEQ ID NO 75
<211> LENGTH: 61
<212> TYPE: DNA
<213> ORGANISM: Artificial Sequence
<220> FEATURE:
<223> OTHER INFORMATION: Synthetic

<400> SEQUENCE: 75
acactctttc cctacacgac gctcttccga tcttgacatg taaaggataa ttgtcagtga        60
c                                                                       61

<210> SEQ ID NO 76
<211> LENGTH: 62
<212> TYPE: DNA
<213> ORGANISM: Artificial Sequence
<220> FEATURE:
<223> OTHER INFORMATION: Synthetic

<400> SEQUENCE: 76
gtgactggag ttcagacgtg tgctcttccg atctaaagat ctagatgcaa gattatttt        60 gg                                                                      62

<210> SEQ ID NO 77
<211> LENGTH: 57
<212> TYPE: DNA
<213> ORGANISM: Artificial Sequence
<220> FEATURE:
<223> OTHER INFORMATION: Synthetic

<400> SEQUENCE: 77
acactctttc cctacacgac gctcttccga tctgtgcaga acatcaagtt caacagt          57

<210> SEQ ID NO 78
<211> LENGTH: 55
<212> TYPE: DNA
<213> ORGANISM: Artificial Sequence
<220> FEATURE:
<223> OTHER INFORMATION: Synthetic

<400> SEQUENCE: 78
gtgactggag ttcagacgtg tgctcttccg atctcaggac atgcacagct acatc            55

<210> SEQ ID NO 79
<211> LENGTH: 57
<212> TYPE: DNA
<213> ORGANISM: Artificial Sequence
<220> FEATURE:

<223> OTHER INFORMATION: Synthetic

<400> SEQUENCE: 79
acactctttc cctacacgac gctcttccga tcttaggtgg aatgaatggc tgaatta                57

<210> SEQ ID NO 80
<211> LENGTH: 57
<212> TYPE: DNA
<213> ORGANISM: Artificial Sequence
<220> FEATURE:
<223> OTHER INFORMATION: Synthetic

<400> SEQUENCE: 80
gtgactggag ttcagacgtg tgctcttccg atctgaaagg gtgctaaaga ggtaaag                57

<210> SEQ ID NO 81
<211> LENGTH: 60
<212> TYPE: DNA
<213> ORGANISM: Artificial Sequence
<220> FEATURE:
<223> OTHER INFORMATION: Synthetic

<400> SEQUENCE: 81
acactctttc cctacacgac gctcttccga tctttcgtcc acaaaatgat tctgaattag            60

<210> SEQ ID NO 82
<211> LENGTH: 58
<212> TYPE: DNA
<213> ORGANISM: Artificial Sequence
<220> FEATURE:
<223> OTHER INFORMATION: Synthetic

<400> SEQUENCE: 82
gtgactggag ttcagacgtg tgctcttccg atctcagtca ttttcagcag gccttata              58

<210> SEQ ID NO 83
<211> LENGTH: 54
<212> TYPE: DNA
<213> ORGANISM: Artificial Sequence
<220> FEATURE:
<223> OTHER INFORMATION: Synthetic

<400> SEQUENCE: 83
acactctttc cctacacgac gctcttccga tcttggygtt ccattgctta cttt                  54

<210> SEQ ID NO 84
<211> LENGTH: 52
<212> TYPE: DNA
<213> ORGANISM: Artificial Sequence
<220> FEATURE:
<223> OTHER INFORMATION: Synthetic

<400> SEQUENCE: 84
gtgactggag ttcagacgtg tgctcttccg atcttgtcca caggacagaa gc                    52

<210> SEQ ID NO 85
<211> LENGTH: 61
<212> TYPE: DNA
<213> ORGANISM: Artificial Sequence
<220> FEATURE:
<223> OTHER INFORMATION: Synthetic

<400> SEQUENCE: 85
acactctttc cctacacgac gctcttccga tctttccata ctactcatga ggtgtttatt            60
c                                                                            61

<210> SEQ ID NO 86
<211> LENGTH: 58
<212> TYPE: DNA
<213> ORGANISM: Artificial Sequence
<220> FEATURE:
<223> OTHER INFORMATION: Synthetic

<400> SEQUENCE: 86
gtgactggag ttcagacgtg tgctcttccg atcttgaaag acgatggaca agtaatgg    58

<210> SEQ ID NO 87
<211> LENGTH: 57
<212> TYPE: DNA
<213> ORGANISM: Artificial Sequence
<220> FEATURE:
<223> OTHER INFORMATION: Synthetic

<400> SEQUENCE: 87
acactctttc cctacacgac gctcttccga tctagaaggc aacttgacaa gagaaat     57

<210> SEQ ID NO 88
<211> LENGTH: 62
<212> TYPE: DNA
<213> ORGANISM: Artificial Sequence
<220> FEATURE:
<223> OTHER INFORMATION: Synthetic

<400> SEQUENCE: 88
gtgactggag ttcagacgtg tgctcttccg atctaataat tgaagaaatt cattcatgtg  60
ca                                                                 62

<210> SEQ ID NO 89
<211> LENGTH: 54
<212> TYPE: DNA
<213> ORGANISM: Artificial Sequence
<220> FEATURE:
<223> OTHER INFORMATION: Synthetic

<400> SEQUENCE: 89
acactctttc cctacacgac gctcttccga tctttctgct cagagctcaa gttc         54

<210> SEQ ID NO 90
<211> LENGTH: 54
<212> TYPE: DNA
<213> ORGANISM: Artificial Sequence
<220> FEATURE:
<223> OTHER INFORMATION: Synthetic

<400> SEQUENCE: 90
gtgactggag ttcagacgtg tgctcttccg atctcctgag cagctatgtc acag         54

<210> SEQ ID NO 91
<211> LENGTH: 60
<212> TYPE: DNA
<213> ORGANISM: Artificial Sequence
<220> FEATURE:
<223> OTHER INFORMATION: Synthetic

<400> SEQUENCE: 91
acactctttc cctacacgac gctcttccga tctctggtat gtatttaacc atgcagatcc  60

<210> SEQ ID NO 92
<211> LENGTH: 62
<212> TYPE: DNA

<213> ORGANISM: Artificial Sequence
<220> FEATURE:
<223> OTHER INFORMATION: Synthetic

<400> SEQUENCE: 92
gtgactggag ttcagacgtg tgctcttccg atctgtgaag atatattcct ccaattcagg    60
ac                                                                  62

<210> SEQ ID NO 93
<211> LENGTH: 51
<212> TYPE: DNA
<213> ORGANISM: Artificial Sequence
<220> FEATURE:
<223> OTHER INFORMATION: Synthetic

<400> SEQUENCE: 93
acactctttc cctacacgac gctcttccga tcttgttgga agctgcttgg g             51

<210> SEQ ID NO 94
<211> LENGTH: 62
<212> TYPE: DNA
<213> ORGANISM: Artificial Sequence
<220> FEATURE:
<223> OTHER INFORMATION: Synthetic

<400> SEQUENCE: 94
gtgactggag ttcagacgtg tgctcttccg atctgttatt tgaagataaa gaacttcrgt    60
gg                                                                  62

<210> SEQ ID NO 95
<211> LENGTH: 54
<212> TYPE: DNA
<213> ORGANISM: Artificial Sequence
<220> FEATURE:
<223> OTHER INFORMATION: Synthetic

<400> SEQUENCE: 95
acactctttc cctacacgac gctcttccga tctgctgagc attagcttgc aaga          54

<210> SEQ ID NO 96
<211> LENGTH: 58
<212> TYPE: DNA
<213> ORGANISM: Artificial Sequence
<220> FEATURE:
<223> OTHER INFORMATION: Synthetic

<400> SEQUENCE: 96
gtgactggag ttcagacgtg tgctcttccg atctcctctt tcttcctgaa tgctgaaa      58

<210> SEQ ID NO 97
<211> LENGTH: 51
<212> TYPE: DNA
<213> ORGANISM: Artificial Sequence
<220> FEATURE:
<223> OTHER INFORMATION: Synthetic

<400> SEQUENCE: 97
acactctttc cctacacgac gctcttccga tctttcagga cctgcttcgc t             51

<210> SEQ ID NO 98
<211> LENGTH: 58
<212> TYPE: DNA
<213> ORGANISM: Artificial Sequence
<220> FEATURE:
<223> OTHER INFORMATION: Synthetic

<400> SEQUENCE: 98
gtgactggag ttcagacgtg tgctcttccg atctccagta agccaactgt tacctttt         58

<210> SEQ ID NO 99
<211> LENGTH: 57
<212> TYPE: DNA
<213> ORGANISM: Artificial Sequence
<220> FEATURE:
<223> OTHER INFORMATION: Synthetic

<400> SEQUENCE: 99
acactctttc cctacacgac gctcttccga tcttgcacaa taaaacagtt agccaga         57

<210> SEQ ID NO 100
<211> LENGTH: 58
<212> TYPE: DNA
<213> ORGANISM: Artificial Sequence
<220> FEATURE:
<223> OTHER INFORMATION: Synthetic

<400> SEQUENCE: 100
gtgactggag ttcagacgtg tgctcttccg atcttctcaa acaggagaag aaggatga         58

<210> SEQ ID NO 101
<211> LENGTH: 57
<212> TYPE: DNA
<213> ORGANISM: Artificial Sequence
<220> FEATURE:
<223> OTHER INFORMATION: Synthetic

<400> SEQUENCE: 101
acactctttc cctacacgac gctcttccga tcttctgcat tggtgctaaa agtttct         57

<210> SEQ ID NO 102
<211> LENGTH: 62
<212> TYPE: DNA
<213> ORGANISM: Artificial Sequence
<220> FEATURE:
<223> OTHER INFORMATION: Synthetic

<400> SEQUENCE: 102
gtgactggag ttcagacgtg tgctcttccg atcttgtaat aattaaattg gcattcctt         60 gg                                                                      62

<210> SEQ ID NO 103
<211> LENGTH: 52
<212> TYPE: DNA
<213> ORGANISM: Artificial Sequence
<220> FEATURE:
<223> OTHER INFORMATION: Synthetic

<400> SEQUENCE: 103
acactctttc cctacacgac gctcttccga tctcatctag tgctgggcct ca              52

<210> SEQ ID NO 104
<211> LENGTH: 52
<212> TYPE: DNA
<213> ORGANISM: Artificial Sequence
<220> FEATURE:
<223> OTHER INFORMATION: Synthetic

<400> SEQUENCE: 104
gtgactggag ttcagacgtg tgctcttccg atctgaccag gtggagccga ag              52

<210> SEQ ID NO 105
<211> LENGTH: 51
<212> TYPE: DNA
<213> ORGANISM: Artificial Sequence
<220> FEATURE:
<223> OTHER INFORMATION: Synthetic

<400> SEQUENCE: 105
acactctttc cctacacgac gctcttccga tcttgcatag ccagggcatt g    51

<210> SEQ ID NO 106
<211> LENGTH: 52
<212> TYPE: DNA
<213> ORGANISM: Artificial Sequence
<220> FEATURE:
<223> OTHER INFORMATION: Synthetic

<400> SEQUENCE: 106
gtgactggag ttcagacgtg tgctcttccg atctgtaggc acgtgctagg gg    52

<210> SEQ ID NO 107
<211> LENGTH: 57
<212> TYPE: DNA
<213> ORGANISM: Artificial Sequence
<220> FEATURE:
<223> OTHER INFORMATION: Synthetic

<400> SEQUENCE: 107
acactctttc cctacacgac gctcttccga tctctgtttc tttctcctct gaagagg    57

<210> SEQ ID NO 108
<211> LENGTH: 57
<212> TYPE: DNA
<213> ORGANISM: Artificial Sequence
<220> FEATURE:
<223> OTHER INFORMATION: Synthetic

<400> SEQUENCE: 108
gtgactggag ttcagacgtg tgctcttccg atctctagtg cagttccaga tgaacac    57

<210> SEQ ID NO 109
<211> LENGTH: 57
<212> TYPE: DNA
<213> ORGANISM: Artificial Sequence
<220> FEATURE:
<223> OTHER INFORMATION: Synthetic

<400> SEQUENCE: 109
acactctttc cctacacgac gctcttccga tctgaaaatg tttcctgact cagaggg    57

<210> SEQ ID NO 110
<211> LENGTH: 52
<212> TYPE: DNA
<213> ORGANISM: Artificial Sequence
<220> FEATURE:
<223> OTHER INFORMATION: Synthetic

<400> SEQUENCE: 110
gtgactggag ttcagacgtg tgctcttccg atctgtgacc cggaaggcag tc    52

<210> SEQ ID NO 111
<211> LENGTH: 61
<212> TYPE: DNA
<213> ORGANISM: Artificial Sequence
<220> FEATURE:
<223> OTHER INFORMATION: Synthetic

<400> SEQUENCE: 111
acactctttc cctacacgac gctcttccga tcttttcctt tgtagtgtcc ataaattctt    60
t    61

<210> SEQ ID NO 112
<211> LENGTH: 62
<212> TYPE: DNA
<213> ORGANISM: Artificial Sequence
<220> FEATURE:
<223> OTHER INFORMATION: Synthetic

<400> SEQUENCE: 112
gtgactggag ttcagacgtg tgctcttccg atcttgttga agaagtatga tgtattgttt    60
gc    62

<210> SEQ ID NO 113
<211> LENGTH: 56
<212> TYPE: DNA
<213> ORGANISM: Artificial Sequence
<220> FEATURE:
<223> OTHER INFORMATION: Synthetic

<400> SEQUENCE: 113
acactctttc cctacacgac gctcttccga tctcgtcgta atcaccacac tgaaag    56

<210> SEQ ID NO 114
<211> LENGTH: 58
<212> TYPE: DNA
<213> ORGANISM: Artificial Sequence
<220> FEATURE:
<223> OTHER INFORMATION: Synthetic

<400> SEQUENCE: 114
gtgactggag ttcagacgtg tgctcttccg atctgggagg ctgtatacac catattga    58

<210> SEQ ID NO 115
<211> LENGTH: 52
<212> TYPE: DNA
<213> ORGANISM: Artificial Sequence
<220> FEATURE:
<223> OTHER INFORMATION: Synthetic

<400> SEQUENCE: 115
acactctttc cctacacgac gctcttccga tcttcacatt gccctgaca ac    52

<210> SEQ ID NO 116
<211> LENGTH: 53
<212> TYPE: DNA
<213> ORGANISM: Artificial Sequence
<220> FEATURE:
<223> OTHER INFORMATION: Synthetic

<400> SEQUENCE: 116
gtgactggag ttcagacgtg tgctcttccg atctcttcac cactttcccg tgg    53

<210> SEQ ID NO 117
<211> LENGTH: 57
<212> TYPE: DNA
<213> ORGANISM: Artificial Sequence
<220> FEATURE:
<223> OTHER INFORMATION: Synthetic

<400> SEQUENCE: 117
acactctttc cctacacgac gctcttccga tcttcctgag tcatttcttc cttttcc    57

<210> SEQ ID NO 118
<211> LENGTH: 57
<212> TYPE: DNA
<213> ORGANISM: Artificial Sequence
<220> FEATURE:
<223> OTHER INFORMATION: Synthetic

<400> SEQUENCE: 118
gtgactggag ttcagacgtg tgctcttccg atctactatg tgtcgaaagg cagtgta    57

<210> SEQ ID NO 119
<211> LENGTH: 54
<212> TYPE: DNA
<213> ORGANISM: Artificial Sequence
<220> FEATURE:
<223> OTHER INFORMATION: Synthetic

<400> SEQUENCE: 119
acactctttc cctacacgac gctcttccga tctatgagct accaaccaag aagg    54

<210> SEQ ID NO 120
<211> LENGTH: 55
<212> TYPE: DNA
<213> ORGANISM: Artificial Sequence
<220> FEATURE:
<223> OTHER INFORMATION: Synthetic

<400> SEQUENCE: 120
gtgactggag ttcagacgtg tgctcttccg atctcagatc ctgttccagg cctat    55

<210> SEQ ID NO 121
<211> LENGTH: 56
<212> TYPE: DNA
<213> ORGANISM: Artificial Sequence
<220> FEATURE:
<223> OTHER INFORMATION: Synthetic

<400> SEQUENCE: 121
acactctttc cctacacgac gctcttccga tctattttgg tcttgccaga gacatg    56

<210> SEQ ID NO 122
<211> LENGTH: 58
<212> TYPE: DNA
<213> ORGANISM: Artificial Sequence
<220> FEATURE:
<223> OTHER INFORMATION: Synthetic

<400> SEQUENCE: 122
gtgactggag ttcagacgtg tgctcttccg atctgctttg gaaagtctgc aaactcaa    58

<210> SEQ ID NO 123
<211> LENGTH: 53
<212> TYPE: DNA
<213> ORGANISM: Artificial Sequence
<220> FEATURE:
<223> OTHER INFORMATION: Synthetic

<400> SEQUENCE: 123
acactctttc cctacacgac gctcttccga tctttccctg caacagctga atc    53

<210> SEQ ID NO 124
<211> LENGTH: 57
<212> TYPE: DNA
<213> ORGANISM: Artificial Sequence

```
<220> FEATURE:
<223> OTHER INFORMATION: Synthetic

<400> SEQUENCE: 124
gtgactggag ttcagacgtg tgctcttccg atcttctcaa tgggcaatga aaatgta          57

<210> SEQ ID NO 125
<211> LENGTH: 56
<212> TYPE: DNA
<213> ORGANISM: Artificial Sequence
<220> FEATURE:
<223> OTHER INFORMATION: Synthetic

<400> SEQUENCE: 125
acactctttc cctacacgac gctcttccga tctgcagtgc taaccaagtt cttttct           56

<210> SEQ ID NO 126
<211> LENGTH: 59
<212> TYPE: DNA
<213> ORGANISM: Artificial Sequence
<220> FEATURE:
<223> OTHER INFORMATION: Synthetic

<400> SEQUENCE: 126
gtgactggag ttcagacgtg tgctcttccg atctcatgga gtatactttt gtggtttgc         59

<210> SEQ ID NO 127
<211> LENGTH: 55
<212> TYPE: DNA
<213> ORGANISM: Artificial Sequence
<220> FEATURE:
<223> OTHER INFORMATION: Synthetic

<400> SEQUENCE: 127
acactctttc cctacacgac gctcttccga tctacratga cttccttctt gagga             55

<210> SEQ ID NO 128
<211> LENGTH: 53
<212> TYPE: DNA
<213> ORGANISM: Artificial Sequence
<220> FEATURE:
<223> OTHER INFORMATION: Synthetic

<400> SEQUENCE: 128
gtgactggag ttcagacgtg tgctcttccg atctccagga tcaccttgcc gaa               53

<210> SEQ ID NO 129
<211> LENGTH: 54
<212> TYPE: DNA
<213> ORGANISM: Artificial Sequence
<220> FEATURE:
<223> OTHER INFORMATION: Synthetic

<400> SEQUENCE: 129
acactctttc cctacacgac gctcttccga tctctgtgtc ctttcaggat ggtg              54

<210> SEQ ID NO 130
<211> LENGTH: 55
<212> TYPE: DNA
<213> ORGANISM: Artificial Sequence
<220> FEATURE:
<223> OTHER INFORMATION: Synthetic

<400> SEQUENCE: 130
gtgactggag ttcagacgtg tgctcttccg atctccactg ctttgagaac gtgac             55
```

<210> SEQ ID NO 131
<211> LENGTH: 51
<212> TYPE: DNA
<213> ORGANISM: Artificial Sequence
<220> FEATURE:
<223> OTHER INFORMATION: Synthetic

<400> SEQUENCE: 131
acactctttc cctacacgac gctcttccga tctcyccacc agcatgtttg a    51

<210> SEQ ID NO 132
<211> LENGTH: 56
<212> TYPE: DNA
<213> ORGANISM: Artificial Sequence
<220> FEATURE:
<223> OTHER INFORMATION: Synthetic

<400> SEQUENCE: 132
gtgactggag ttcagacgtg tgctcttccg atctctttgc ttctgtgttg ttaggg    56

<210> SEQ ID NO 133
<211> LENGTH: 57
<212> TYPE: DNA
<213> ORGANISM: Artificial Sequence
<220> FEATURE:
<223> OTHER INFORMATION: Synthetic

<400> SEQUENCE: 133
acactctttc cctacacgac gctcttccga tctttctagt gcattcaagc acaatgg    57

<210> SEQ ID NO 134
<211> LENGTH: 58
<212> TYPE: DNA
<213> ORGANISM: Artificial Sequence
<220> FEATURE:
<223> OTHER INFORMATION: Synthetic

<400> SEQUENCE: 134
gtgactggag ttcagacgtg tgctcttccg atctccaatt taaggggatg tttaggct    58

<210> SEQ ID NO 135
<211> LENGTH: 60
<212> TYPE: DNA
<213> ORGANISM: Artificial Sequence
<220> FEATURE:
<223> OTHER INFORMATION: Synthetic

<400> SEQUENCE: 135
acactctttc cctacacgac gctcttccga tctccaatgg actattttag aagaaatgga    60

<210> SEQ ID NO 136
<211> LENGTH: 58
<212> TYPE: DNA
<213> ORGANISM: Artificial Sequence
<220> FEATURE:
<223> OTHER INFORMATION: Synthetic

<400> SEQUENCE: 136
gtgactggag ttcagacgtg tgctcttccg atctgggcaa ttaaaagaga agaatgga    58

<210> SEQ ID NO 137
<211> LENGTH: 53
<212> TYPE: DNA
<213> ORGANISM: Artificial Sequence
<220> FEATURE:
<223> OTHER INFORMATION: Synthetic

<400> SEQUENCE: 137
acactctttc cctacacgac gctcttccga tctgtctctc ggaggaagga ctt            53

<210> SEQ ID NO 138
<211> LENGTH: 58
<212> TYPE: DNA
<213> ORGANISM: Artificial Sequence
<220> FEATURE:
<223> OTHER INFORMATION: Synthetic

<400> SEQUENCE: 138
gtgactggag ttcagacgtg tgctcttccg atctgcagag agggatgtaa ccaaaatt      58

<210> SEQ ID NO 139
<211> LENGTH: 53
<212> TYPE: DNA
<213> ORGANISM: Artificial Sequence
<220> FEATURE:
<223> OTHER INFORMATION: Synthetic

<400> SEQUENCE: 139
acactctttc cctacacgac gctcttccga tcttgacctt agcaggatcc agg            53

<210> SEQ ID NO 140
<211> LENGTH: 52
<212> TYPE: DNA
<213> ORGANISM: Artificial Sequence
<220> FEATURE:
<223> OTHER INFORMATION: Synthetic

<400> SEQUENCE: 140
gtgactggag ttcagacgtg tgctcttccg atctcctgtc ggtgagcact ga             52

<210> SEQ ID NO 141
<211> LENGTH: 56
<212> TYPE: DNA
<213> ORGANISM: Artificial Sequence
<220> FEATURE:
<223> OTHER INFORMATION: Synthetic

<400> SEQUENCE: 141
acactctttc cctacacgac gctcttccga tcttgaaagc tgtaccatac ctgtct         56

<210> SEQ ID NO 142
<211> LENGTH: 52
<212> TYPE: DNA
<213> ORGANISM: Artificial Sequence
<220> FEATURE:
<223> OTHER INFORMATION: Synthetic

<400> SEQUENCE: 142
gtgactggag ttcagacgtg tgctcttccg atctccagtt cgtgggcttg tt             52

<210> SEQ ID NO 143
<211> LENGTH: 59
<212> TYPE: DNA
<213> ORGANISM: Artificial Sequence
<220> FEATURE:
<223> OTHER INFORMATION: Synthetic

<400> SEQUENCE: 143
acactctttc cctacacgac gctcttccga tctgtcacaa tgtcaccaca ttacatact     59

<210> SEQ ID NO 144

<210> SEQ ID NO 144
<211> LENGTH: 61
<212> TYPE: DNA
<213> ORGANISM: Artificial Sequence
<220> FEATURE:
<223> OTHER INFORMATION: Synthetic

<400> SEQUENCE: 144
gtgactggag ttcagacgtg tgctcttccg atcttctacc aagtgttttc ttgataaaaa    60
c                                                                   61

<210> SEQ ID NO 145
<211> LENGTH: 57
<212> TYPE: DNA
<213> ORGANISM: Artificial Sequence
<220> FEATURE:
<223> OTHER INFORMATION: Synthetic

<400> SEQUENCE: 145
acactctttc cctacacgac gctcttccga tctatttgac cgtggagaag tagaatc       57

<210> SEQ ID NO 146
<211> LENGTH: 58
<212> TYPE: DNA
<213> ORGANISM: Artificial Sequence
<220> FEATURE:
<223> OTHER INFORMATION: Synthetic

<400> SEQUENCE: 146
gtgactggag ttcagacgtg tgctcttccg atctgagaga gccaaagtac cataggta      58

<210> SEQ ID NO 147
<211> LENGTH: 55
<212> TYPE: DNA
<213> ORGANISM: Artificial Sequence
<220> FEATURE:
<223> OTHER INFORMATION: Synthetic

<400> SEQUENCE: 147
acactctttc cctacacgac gctcttccga tcttcatgta ctggtccctc attgc         55

<210> SEQ ID NO 148
<211> LENGTH: 57
<212> TYPE: DNA
<213> ORGANISM: Artificial Sequence
<220> FEATURE:
<223> OTHER INFORMATION: Synthetic

<400> SEQUENCE: 148
gtgactggag ttcagacgtg tgctcttccg atctccaaga dacaggtttc tccatca       57

<210> SEQ ID NO 149
<211> LENGTH: 57
<212> TYPE: DNA
<213> ORGANISM: Artificial Sequence
<220> FEATURE:
<223> OTHER INFORMATION: Synthetic

<400> SEQUENCE: 149
acactctttc cctacacgac gctcttccga tctatgatag ccgtctttaa caagctc       57

<210> SEQ ID NO 150
<211> LENGTH: 59
<212> TYPE: DNA
<213> ORGANISM: Artificial Sequence
<220> FEATURE:
<223> OTHER INFORMATION: Synthetic

<400> SEQUENCE: 150
gtgactggag ttcagacgtg tgctcttccg atctcagaaa tggtttcaaa tgaatctgt    59

<210> SEQ ID NO 151
<211> LENGTH: 55
<212> TYPE: DNA
<213> ORGANISM: Artificial Sequence
<220> FEATURE:
<223> OTHER INFORMATION: Synthetic

<400> SEQUENCE: 151
acactctttc cctacacgac gctcttccga tctccaggaa cgtactggtg aaaac    55

<210> SEQ ID NO 152
<211> LENGTH: 55
<212> TYPE: DNA
<213> ORGANISM: Artificial Sequence
<220> FEATURE:
<223> OTHER INFORMATION: Synthetic

<400> SEQUENCE: 152
gtgactggag ttcagacgtg tgctcttccg atctcatttt cctgacacca gggac    55

<210> SEQ ID NO 153
<211> LENGTH: 53
<212> TYPE: DNA
<213> ORGANISM: Artificial Sequence
<220> FEATURE:
<223> OTHER INFORMATION: Synthetic

<400> SEQUENCE: 153
acactctttc cctacacgac gctcttccga tcttgtccca gaatgcaaga agc    53

<210> SEQ ID NO 154
<211> LENGTH: 52
<212> TYPE: DNA
<213> ORGANISM: Artificial Sequence
<220> FEATURE:
<223> OTHER INFORMATION: Synthetic

<400> SEQUENCE: 154
gtgactggag ttcagacgtg tgctcttccg atctggagca gcctctggca tt    52

<210> SEQ ID NO 155
<211> LENGTH: 55
<212> TYPE: DNA
<213> ORGANISM: Artificial Sequence
<220> FEATURE:
<223> OTHER INFORMATION: Synthetic

<400> SEQUENCE: 155
acactctttc cctacacgac gctcttccga tcttgttttg tgggctacaa gaact    55

<210> SEQ ID NO 156
<211> LENGTH: 52
<212> TYPE: DNA
<213> ORGANISM: Artificial Sequence
<220> FEATURE:
<223> OTHER INFORMATION: Synthetic

<400> SEQUENCE: 156
gtgactggag ttcagacgtg tgctcttccg atctgggcac ttgctgccag ta    52

<210> SEQ ID NO 157

```
<211> LENGTH: 57
<212> TYPE: DNA
<213> ORGANISM: Artificial Sequence
<220> FEATURE:
<223> OTHER INFORMATION: Synthetic

<400> SEQUENCE: 157
acactctttc cctacacgac gctcttccga tcttaaactt actttgcctg tgactgc        57

<210> SEQ ID NO 158
<211> LENGTH: 58
<212> TYPE: DNA
<213> ORGANISM: Artificial Sequence
<220> FEATURE:
<223> OTHER INFORMATION: Synthetic

<400> SEQUENCE: 158
gtgactggag ttcagacgtg tgctcttccg atctgcacct ataagaaaga tgtgcaga       58

<210> SEQ ID NO 159
<211> LENGTH: 56
<212> TYPE: DNA
<213> ORGANISM: Artificial Sequence
<220> FEATURE:
<223> OTHER INFORMATION: Synthetic

<400> SEQUENCE: 159
acactctttc cctacacgac gctcttccga tctgtggaga agatcaacct gtttgc         56

<210> SEQ ID NO 160
<211> LENGTH: 52
<212> TYPE: DNA
<213> ORGANISM: Artificial Sequence
<220> FEATURE:
<223> OTHER INFORMATION: Synthetic

<400> SEQUENCE: 160
gtgactggag ttcagacgtg tgctcttccg atctctcacc ctcagccttg gg             52

<210> SEQ ID NO 161
<211> LENGTH: 57
<212> TYPE: DNA
<213> ORGANISM: Artificial Sequence
<220> FEATURE:
<223> OTHER INFORMATION: Synthetic

<400> SEQUENCE: 161
acactctttc cctacacgac gctcttccga tctgcctgaa tgatgacatt cttttcg        57

<210> SEQ ID NO 162
<211> LENGTH: 59
<212> TYPE: DNA
<213> ORGANISM: Artificial Sequence
<220> FEATURE:
<223> OTHER INFORMATION: Synthetic

<400> SEQUENCE: 162
gtgactggag ttcagacgtg tgctcttccg atctgtcaac aaaaacaatg tgagatgtc      59

<210> SEQ ID NO 163
<211> LENGTH: 57
<212> TYPE: DNA
<213> ORGANISM: Artificial Sequence
<220> FEATURE:
<223> OTHER INFORMATION: Synthetic

<400> SEQUENCE: 163
```
acactctttc cctacacgac gctcttccga tctaccagag tttcaacaaa gtagctg    57

<210> SEQ ID NO 164
<211> LENGTH: 54
<212> TYPE: DNA
<213> ORGANISM: Artificial Sequence
<220> FEATURE:
<223> OTHER INFORMATION: Synthetic

<400> SEQUENCE: 164
gtgactggag ttcagacgtg tgctcttccg atctgagtgg aagaaggcac tgtg    54

<210> SEQ ID NO 165
<211> LENGTH: 53
<212> TYPE: DNA
<213> ORGANISM: Artificial Sequence
<220> FEATURE:
<223> OTHER INFORMATION: Synthetic

<400> SEQUENCE: 165
acactctttc cctacacgac gctcttccga tctcggcaya ggatgactgt tac    53

<210> SEQ ID NO 166
<211> LENGTH: 54
<212> TYPE: DNA
<213> ORGANISM: Artificial Sequence
<220> FEATURE:
<223> OTHER INFORMATION: Synthetic

<400> SEQUENCE: 166
gtgactggag ttcagacgtg tgctcttccg atctagagtt agcacaccag actg    54

<210> SEQ ID NO 167
<211> LENGTH: 55
<212> TYPE: DNA
<213> ORGANISM: Artificial Sequence
<220> FEATURE:
<223> OTHER INFORMATION: Synthetic

<400> SEQUENCE: 167
acactctttc cctacacgac gctcttccga tctatttcca tcctgcagaa gaagc    55

<210> SEQ ID NO 168
<211> LENGTH: 58
<212> TYPE: DNA
<213> ORGANISM: Artificial Sequence
<220> FEATURE:
<223> OTHER INFORMATION: Synthetic

<400> SEQUENCE: 168
gtgactggag ttcagacgtg tgctcttccg atctaggatg gattcgactt agacttga    58

<210> SEQ ID NO 169
<211> LENGTH: 57
<212> TYPE: DNA
<213> ORGANISM: Artificial Sequence
<220> FEATURE:
<223> OTHER INFORMATION: Synthetic

<400> SEQUENCE: 169
acactctttc cctacacgac gctcttccga tctgctcttt aacaaccttt gcttgtc    57

<210> SEQ ID NO 170
<211> LENGTH: 57
<212> TYPE: DNA

```
<213> ORGANISM: Artificial Sequence
<220> FEATURE:
<223> OTHER INFORMATION: Synthetic

<400> SEQUENCE: 170
gtgactggag ttcagacgtg tgctcttccg atctcaatat cacactgcca ggtactg        57

<210> SEQ ID NO 171
<211> LENGTH: 57
<212> TYPE: DNA
<213> ORGANISM: Artificial Sequence
<220> FEATURE:
<223> OTHER INFORMATION: Synthetic

<400> SEQUENCE: 171
acactctttc cctacacgac gctcttccga tcttctcttc cattgtagag caaatcc        57

<210> SEQ ID NO 172
<211> LENGTH: 58
<212> TYPE: DNA
<213> ORGANISM: Artificial Sequence
<220> FEATURE:
<223> OTHER INFORMATION: Synthetic

<400> SEQUENCE: 172
gtgactggag ttcagacgtg tgctcttccg atctgttctc tctccagagt gctctaat       58

<210> SEQ ID NO 173
<211> LENGTH: 61
<212> TYPE: DNA
<213> ORGANISM: Artificial Sequence
<220> FEATURE:
<223> OTHER INFORMATION: Synthetic

<400> SEQUENCE: 173
acactctttc cctacacgac gctcttccga tcttattcaa ataacaccca atgaagaatg     60
t                                                                     61

<210> SEQ ID NO 174
<211> LENGTH: 59
<212> TYPE: DNA
<213> ORGANISM: Artificial Sequence
<220> FEATURE:
<223> OTHER INFORMATION: Synthetic

<400> SEQUENCE: 174
gtgactggag ttcagacgtg tgctcttccg atctggttca caactatcaa tgagttcat      59

<210> SEQ ID NO 175
<211> LENGTH: 52
<212> TYPE: DNA
<213> ORGANISM: Artificial Sequence
<220> FEATURE:
<223> OTHER INFORMATION: Synthetic

<400> SEQUENCE: 175
acactctttc cctacacgac gctcttccga tctctcatca cgcagctcat gc             52

<210> SEQ ID NO 176
<211> LENGTH: 56
<212> TYPE: DNA
<213> ORGANISM: Artificial Sequence
<220> FEATURE:
<223> OTHER INFORMATION: Synthetic

<400> SEQUENCE: 176
```

```
gtgactggag ttcagacgtg tgctcttccg atctgagata aggagccagg atcctc        56
```

<210> SEQ ID NO 177
<211> LENGTH: 53
<212> TYPE: DNA
<213> ORGANISM: Artificial Sequence
<220> FEATURE:
<223> OTHER INFORMATION: Synthetic

<400> SEQUENCE: 177

```
acactctttc cctacacgac gctcttccga tctcccagca tgtcaccaag atg        53
```

<210> SEQ ID NO 178
<211> LENGTH: 55
<212> TYPE: DNA
<213> ORGANISM: Artificial Sequence
<220> FEATURE:
<223> OTHER INFORMATION: Synthetic

<400> SEQUENCE: 178

```
gtgactggag ttcagacgtg tgctcttccg atctgcttct gggactggag tacag        55
```

<210> SEQ ID NO 179
<211> LENGTH: 57
<212> TYPE: DNA
<213> ORGANISM: Artificial Sequence
<220> FEATURE:
<223> OTHER INFORMATION: Synthetic

<400> SEQUENCE: 179

```
acactctttc cctacacgac gctcttccga tctaagtccc aaccatgaca agatttt        57
```

<210> SEQ ID NO 180
<211> LENGTH: 58
<212> TYPE: DNA
<213> ORGANISM: Artificial Sequence
<220> FEATURE:
<223> OTHER INFORMATION: Synthetic

<400> SEQUENCE: 180

```
gtgactggag ttcagacgtg tgctcttccg atctgtgtcc gatctgtaga tccactaa        58
```

<210> SEQ ID NO 181
<211> LENGTH: 53
<212> TYPE: DNA
<213> ORGANISM: Artificial Sequence
<220> FEATURE:
<223> OTHER INFORMATION: Synthetic

<400> SEQUENCE: 181

```
acactctttc cctacacgac gctcttccga tcttgccagc taaaggtgaa gat        53
```

<210> SEQ ID NO 182
<211> LENGTH: 59
<212> TYPE: DNA
<213> ORGANISM: Artificial Sequence
<220> FEATURE:
<223> OTHER INFORMATION: Synthetic

<400> SEQUENCE: 182

```
gtgactggag ttcagacgtg tgctcttccg atcttttgta ctttactttc attgggaga        59
```

<210> SEQ ID NO 183
<211> LENGTH: 57
<212> TYPE: DNA

<213> ORGANISM: Artificial Sequence
<220> FEATURE:
<223> OTHER INFORMATION: Synthetic

<400> SEQUENCE: 183
acactctttc cctacacgac gctcttccga tctctccatc aagtatgatg gtgaagg    57

<210> SEQ ID NO 184
<211> LENGTH: 56
<212> TYPE: DNA
<213> ORGANISM: Artificial Sequence
<220> FEATURE:
<223> OTHER INFORMATION: Synthetic

<400> SEQUENCE: 184
gtgactggag ttcagacgtg tgctcttccg atctcatcca gcatccacca agtaat    56

<210> SEQ ID NO 185
<211> LENGTH: 57
<212> TYPE: DNA
<213> ORGANISM: Artificial Sequence
<220> FEATURE:
<223> OTHER INFORMATION: Synthetic

<400> SEQUENCE: 185
acactctttc cctacacgac gctcttccga tcttcttcca cacaattaaa cagcatg    57

<210> SEQ ID NO 186
<211> LENGTH: 57
<212> TYPE: DNA
<213> ORGANISM: Artificial Sequence
<220> FEATURE:
<223> OTHER INFORMATION: Synthetic

<400> SEQUENCE: 186
gtgactggag ttcagacgtg tgctcttccg atctgaattg cacaatccat gaacagc    57

<210> SEQ ID NO 187
<211> LENGTH: 57
<212> TYPE: DNA
<213> ORGANISM: Artificial Sequence
<220> FEATURE:
<223> OTHER INFORMATION: Synthetic

<400> SEQUENCE: 187
acactctttc cctacacgac gctcttccga tcttagtgta ttcacagaga cttggca    57

<210> SEQ ID NO 188
<211> LENGTH: 57
<212> TYPE: DNA
<213> ORGANISM: Artificial Sequence
<220> FEATURE:
<223> OTHER INFORMATION: Synthetic

<400> SEQUENCE: 188
gtgactggag ttcagacgtg tgctcttccg atctgaaacg tgagtaccca ttctctg    57

<210> SEQ ID NO 189
<211> LENGTH: 57
<212> TYPE: DNA
<213> ORGANISM: Artificial Sequence
<220> FEATURE:
<223> OTHER INFORMATION: Synthetic

<400> SEQUENCE: 189
acactctttc cctacacgac gctcttccga tctcatgttt ccaattttag cgagtgc    57

<210> SEQ ID NO 190
<211> LENGTH: 57
<212> TYPE: DNA
<213> ORGANISM: Artificial Sequence
<220> FEATURE:
<223> OTHER INFORMATION: Synthetic

<400> SEQUENCE: 190
gtgactggag ttcagacgtg tgctcttccg atcttgtcca agctgccttt tattgtc    57

<210> SEQ ID NO 191
<211> LENGTH: 59
<212> TYPE: DNA
<213> ORGANISM: Artificial Sequence
<220> FEATURE:
<223> OTHER INFORMATION: Synthetic

<400> SEQUENCE: 191
acactctttc cctacacgac gctcttccga tcttgtgtag gaaaggtaca atgatttcc    59

<210> SEQ ID NO 192
<211> LENGTH: 61
<212> TYPE: DNA
<213> ORGANISM: Artificial Sequence
<220> FEATURE:
<223> OTHER INFORMATION: Synthetic

<400> SEQUENCE: 192
gtgactggag ttcagacgtg tgctcttccg atctgtggat tcctctaagt gaaaatcatg    60
a                                                                   61

<210> SEQ ID NO 193
<211> LENGTH: 56
<212> TYPE: DNA
<213> ORGANISM: Artificial Sequence
<220> FEATURE:
<223> OTHER INFORMATION: Synthetic

<400> SEQUENCE: 193
acactctttc cctacacgac gctcttccga tctgaaggac tgttgcagat agcatc    56

<210> SEQ ID NO 194
<211> LENGTH: 59
<212> TYPE: DNA
<213> ORGANISM: Artificial Sequence
<220> FEATURE:
<223> OTHER INFORMATION: Synthetic

<400> SEQUENCE: 194
gtgactggag ttcagacgtg tgctcttccg atctaaagta ggcagccttt ataaaagca    59

<210> SEQ ID NO 195
<211> LENGTH: 54
<212> TYPE: DNA
<213> ORGANISM: Artificial Sequence
<220> FEATURE:
<223> OTHER INFORMATION: Synthetic

<400> SEQUENCE: 195
acactctttc cctacacgac gctcttccga tctgggtgag gcagtctttta ctca    54

<210> SEQ ID NO 196
<211> LENGTH: 58
<212> TYPE: DNA

```
<213> ORGANISM: Artificial Sequence
<220> FEATURE:
<223> OTHER INFORMATION: Synthetic

<400> SEQUENCE: 196
gtgactggag ttcagacgtg tgctcttccg atctgggaag aaaggaaatg catttcct        58

<210> SEQ ID NO 197
<211> LENGTH: 51
<212> TYPE: DNA
<213> ORGANISM: Artificial Sequence
<220> FEATURE:
<223> OTHER INFORMATION: Synthetic

<400> SEQUENCE: 197
acactctttc cctacacgac gctcttccga tctgcgaagc cacactgacg t               51

<210> SEQ ID NO 198
<211> LENGTH: 54
<212> TYPE: DNA
<213> ORGANISM: Artificial Sequence
<220> FEATURE:
<223> OTHER INFORMATION: Synthetic

<400> SEQUENCE: 198
gtgactggag ttcagacgtg tgctcttccg atctgctgcc tcctggacta tgtc            54

<210> SEQ ID NO 199
<211> LENGTH: 57
<212> TYPE: DNA
<213> ORGANISM: Artificial Sequence
<220> FEATURE:
<223> OTHER INFORMATION: Synthetic

<400> SEQUENCE: 199
acactctttc cctacacgac gctcttccga tctttaccat ccacaaaatg gatccag         57

<210> SEQ ID NO 200
<211> LENGTH: 61
<212> TYPE: DNA
<213> ORGANISM: Artificial Sequence
<220> FEATURE:
<223> OTHER INFORMATION: Synthetic

<400> SEQUENCE: 200
gtgactggag ttcagacgtg tgctcttccg atctgtaagt aaaggaaaac agtagatctc      60
a                                                                     61

<210> SEQ ID NO 201
<211> LENGTH: 51
<212> TYPE: DNA
<213> ORGANISM: Artificial Sequence
<220> FEATURE:
<223> OTHER INFORMATION: Synthetic

<400> SEQUENCE: 201
acactctttc cctacacgac gctcttccga tctcgaaact gcctggtagg g               51

<210> SEQ ID NO 202
<211> LENGTH: 52
<212> TYPE: DNA
<213> ORGANISM: Artificial Sequence
<220> FEATURE:
<223> OTHER INFORMATION: Synthetic

<400> SEQUENCE: 202
```

```
gtgactggag ttcagacgtg tgctcttccg atctggagcc aagttcccca tc         52
```

<210> SEQ ID NO 203
<211> LENGTH: 57
<212> TYPE: DNA
<213> ORGANISM: Artificial Sequence
<220> FEATURE:
<223> OTHER INFORMATION: Synthetic

<400> SEQUENCE: 203

```
acactctttc cctacacgac gctcttccga tctacttacg tggacatttc ttgacac    57
```

<210> SEQ ID NO 204
<211> LENGTH: 58
<212> TYPE: DNA
<213> ORGANISM: Artificial Sequence
<220> FEATURE:
<223> OTHER INFORMATION: Synthetic

<400> SEQUENCE: 204

```
gtgactggag ttcagacgtg tgctcttccg atcttccact gtcattgaaa ttcatgca   58
```

<210> SEQ ID NO 205
<211> LENGTH: 57
<212> TYPE: DNA
<213> ORGANISM: Artificial Sequence
<220> FEATURE:
<223> OTHER INFORMATION: Synthetic

<400> SEQUENCE: 205

```
acactctttc cctacacgac gctcttccga tctcagactg cagggttcta gtttatc    57
```

<210> SEQ ID NO 206
<211> LENGTH: 58
<212> TYPE: DNA
<213> ORGANISM: Artificial Sequence
<220> FEATURE:
<223> OTHER INFORMATION: Synthetic

<400> SEQUENCE: 206

```
gtgactggag ttcagacgtg tgctcttccg atctcccact catgtttagc agatgtac   58
```

<210> SEQ ID NO 207
<211> LENGTH: 51
<212> TYPE: DNA
<213> ORGANISM: Artificial Sequence
<220> FEATURE:
<223> OTHER INFORMATION: Synthetic

<400> SEQUENCE: 207

```
acactctttc cctacacgac gctcttccga tctcagtccg gcttggagga t          51
```

<210> SEQ ID NO 208
<211> LENGTH: 52
<212> TYPE: DNA
<213> ORGANISM: Artificial Sequence
<220> FEATURE:
<223> OTHER INFORMATION: Synthetic

<400> SEQUENCE: 208

```
gtgactggag ttcagacgtg tgctcttccg atctggagtg gggatgggag aa         52
```

<210> SEQ ID NO 209
<211> LENGTH: 57
<212> TYPE: DNA

```
<213> ORGANISM: Artificial Sequence
<220> FEATURE:
<223> OTHER INFORMATION: Synthetic

<400> SEQUENCE: 209
acactctttc cctacacgac gctcttccga tctaccacag ctagaactta tcaaacc        57

<210> SEQ ID NO 210
<211> LENGTH: 58
<212> TYPE: DNA
<213> ORGANISM: Artificial Sequence
<220> FEATURE:
<223> OTHER INFORMATION: Synthetic

<400> SEQUENCE: 210
gtgactggag ttcagacgtg tgctcttccg atcttgtgca tatttattac atcggggc       58

<210> SEQ ID NO 211
<211> LENGTH: 51
<212> TYPE: DNA
<213> ORGANISM: Artificial Sequence
<220> FEATURE:
<223> OTHER INFORMATION: Synthetic

<400> SEQUENCE: 211
acactctttc cctacacgac gctcttccga tctggctatg gcacctgcaa c              51

<210> SEQ ID NO 212
<211> LENGTH: 52
<212> TYPE: DNA
<213> ORGANISM: Artificial Sequence
<220> FEATURE:
<223> OTHER INFORMATION: Synthetic

<400> SEQUENCE: 212
gtgactggag ttcagacgtg tgctcttccg atctcagccc cacagaggtc tc             52

<210> SEQ ID NO 213
<211> LENGTH: 57
<212> TYPE: DNA
<213> ORGANISM: Artificial Sequence
<220> FEATURE:
<223> OTHER INFORMATION: Synthetic

<400> SEQUENCE: 213
acactctttc cctacacgac gctcttccga tctttgcagt cttacatttg accatga        57

<210> SEQ ID NO 214
<211> LENGTH: 58
<212> TYPE: DNA
<213> ORGANISM: Artificial Sequence
<220> FEATURE:
<223> OTHER INFORMATION: Synthetic

<400> SEQUENCE: 214
gtgactggag ttcagacgtg tgctcttccg atcttttttcc tccaaaggtc atcagttc      58

<210> SEQ ID NO 215
<211> LENGTH: 56
<212> TYPE: DNA
<213> ORGANISM: Artificial Sequence
<220> FEATURE:
<223> OTHER INFORMATION: Synthetic

<400> SEQUENCE: 215
acactctttc cctacacgac gctcttccga tcttagctga tttgatggag ttggac         56
```

<210> SEQ ID NO 216
<211> LENGTH: 57
<212> TYPE: DNA
<213> ORGANISM: Artificial Sequence
<220> FEATURE:
<223> OTHER INFORMATION: Synthetic

<400> SEQUENCE: 216
gtgactggag ttcagacgtg tgctcttccg atctgtaaag gcaatcctga ggaagag    57

<210> SEQ ID NO 217
<211> LENGTH: 51
<212> TYPE: DNA
<213> ORGANISM: Artificial Sequence
<220> FEATURE:
<223> OTHER INFORMATION: Synthetic

<400> SEQUENCE: 217
acactctttc cctacacgac gctcttccga tctctgggct ccaacctcgt c    51

<210> SEQ ID NO 218
<211> LENGTH: 52
<212> TYPE: DNA
<213> ORGANISM: Artificial Sequence
<220> FEATURE:
<223> OTHER INFORMATION: Synthetic

<400> SEQUENCE: 218
gtgactggag ttcagacgtg tgctcttccg atctcacaag ctggccatgg ac    52

<210> SEQ ID NO 219
<211> LENGTH: 57
<212> TYPE: DNA
<213> ORGANISM: Artificial Sequence
<220> FEATURE:
<223> OTHER INFORMATION: Synthetic

<400> SEQUENCE: 219
acactctttc cctacacgac gctcttccga tctttggtaa ttcaccagtt acctgtc    57

<210> SEQ ID NO 220
<211> LENGTH: 58
<212> TYPE: DNA
<213> ORGANISM: Artificial Sequence
<220> FEATURE:
<223> OTHER INFORMATION: Synthetic

<400> SEQUENCE: 220
gtgactggag ttcagacgtg tgctcttccg atctgcctta tgactcaaga tgggagtt    58

<210> SEQ ID NO 221
<211> LENGTH: 54
<212> TYPE: DNA
<213> ORGANISM: Artificial Sequence
<220> FEATURE:
<223> OTHER INFORMATION: Synthetic

<400> SEQUENCE: 221
acactctttc cctacacgac gctcttccga tctgtgggta tggacacgtt catc    54

<210> SEQ ID NO 222
<211> LENGTH: 52
<212> TYPE: DNA
<213> ORGANISM: Artificial Sequence
<220> FEATURE:

```
<223> OTHER INFORMATION: Synthetic

<400> SEQUENCE: 222
gtgactggag ttcagacgtg tgctcttccg atctgcaagg tgaaggaggt gc      52

<210> SEQ ID NO 223
<211> LENGTH: 57
<212> TYPE: DNA
<213> ORGANISM: Artificial Sequence
<220> FEATURE:
<223> OTHER INFORMATION: Synthetic

<400> SEQUENCE: 223
acactctttc cctacacgac gctcttccga tctgctgttc tcagtttgt cactaaa    57

<210> SEQ ID NO 224
<211> LENGTH: 61
<212> TYPE: DNA
<213> ORGANISM: Artificial Sequence
<220> FEATURE:
<223> OTHER INFORMATION: Synthetic

<400> SEQUENCE: 224
gtgactggag ttcagacgtg tgctcttccg atctaaggta atttgcaatt aactcttgat   60
t                                                                   61

<210> SEQ ID NO 225
<211> LENGTH: 57
<212> TYPE: DNA
<213> ORGANISM: Artificial Sequence
<220> FEATURE:
<223> OTHER INFORMATION: Synthetic

<400> SEQUENCE: 225
acactctttc cctacacgac gctcttccga tctaacaaca cttgaaaatc tgagcag     57

<210> SEQ ID NO 226
<211> LENGTH: 58
<212> TYPE: DNA
<213> ORGANISM: Artificial Sequence
<220> FEATURE:
<223> OTHER INFORMATION: Synthetic

<400> SEQUENCE: 226
gtgactggag ttcagacgtg tgctcttccg atctggtttg cactccaatc tctatcag    58

<210> SEQ ID NO 227
<211> LENGTH: 54
<212> TYPE: DNA
<213> ORGANISM: Artificial Sequence
<220> FEATURE:
<223> OTHER INFORMATION: Synthetic

<400> SEQUENCE: 227
acactctttc cctacacgac gctcttccga tctaattcca gtggccatca aagt         54

<210> SEQ ID NO 228
<211> LENGTH: 52
<212> TYPE: DNA
<213> ORGANISM: Artificial Sequence
<220> FEATURE:
<223> OTHER INFORMATION: Synthetic

<400> SEQUENCE: 228
gtgactggag ttcagacgtg tgctcttccg atctcaccct ctcctgctag ga           52
```

<210> SEQ ID NO 229
<211> LENGTH: 57
<212> TYPE: DNA
<213> ORGANISM: Artificial Sequence
<220> FEATURE:
<223> OTHER INFORMATION: Synthetic

<400> SEQUENCE: 229
acactctttc cctacacgac gctcttccga tctaccytgc aatgtttgta aacactg    57

<210> SEQ ID NO 230
<211> LENGTH: 55
<212> TYPE: DNA
<213> ORGANISM: Artificial Sequence
<220> FEATURE:
<223> OTHER INFORMATION: Synthetic

<400> SEQUENCE: 230
gtgactggag ttcagacgtg tgctcttccg atctgtgtga atgcaattcc ctgtc    55

<210> SEQ ID NO 231
<211> LENGTH: 57
<212> TYPE: DNA
<213> ORGANISM: Artificial Sequence
<220> FEATURE:
<223> OTHER INFORMATION: Synthetic

<400> SEQUENCE: 231
acactctttc cctacacgac gctcttccga tcttctgatg tcttccaaat cttttct    57

<210> SEQ ID NO 232
<211> LENGTH: 54
<212> TYPE: DNA
<213> ORGANISM: Artificial Sequence
<220> FEATURE:
<223> OTHER INFORMATION: Synthetic

<400> SEQUENCE: 232
gtgactggag ttcagacgtg tgctcttccg atctaaattc acttacaccg ggcc    54

<210> SEQ ID NO 233
<211> LENGTH: 54
<212> TYPE: DNA
<213> ORGANISM: Artificial Sequence
<220> FEATURE:
<223> OTHER INFORMATION: Synthetic

<400> SEQUENCE: 233
acactctttc cctacacgac gctcttccga tcttttgatt tgcgtcagtg tcat    54

<210> SEQ ID NO 234
<211> LENGTH: 54
<212> TYPE: DNA
<213> ORGANISM: Artificial Sequence
<220> FEATURE:
<223> OTHER INFORMATION: Synthetic

<400> SEQUENCE: 234
gtgactggag ttcagacgtg tgctcttccg atctgtaggt ggaatagctc cagc    54

<210> SEQ ID NO 235
<211> LENGTH: 57
<212> TYPE: DNA
<213> ORGANISM: Artificial Sequence
<220> FEATURE:

```
<223> OTHER INFORMATION: Synthetic

<400> SEQUENCE: 235
acactctttc cctacacgac gctcttccga tctttaacgt cttccttctc tctctgt        57

<210> SEQ ID NO 236
<211> LENGTH: 56
<212> TYPE: DNA
<213> ORGANISM: Artificial Sequence
<220> FEATURE:
<223> OTHER INFORMATION: Synthetic

<400> SEQUENCE: 236
gtgactggag ttcagacgtg tgctcttccg atcttgagtt tctgctttgc tgtgtg         56

<210> SEQ ID NO 237
<211> LENGTH: 52
<212> TYPE: DNA
<213> ORGANISM: Artificial Sequence
<220> FEATURE:
<223> OTHER INFORMATION: Synthetic

<400> SEQUENCE: 237
acactctttc cctacacgac gctcttccga tctctcactg tctccagcca tg             52

<210> SEQ ID NO 238
<211> LENGTH: 56
<212> TYPE: DNA
<213> ORGANISM: Artificial Sequence
<220> FEATURE:
<223> OTHER INFORMATION: Synthetic

<400> SEQUENCE: 238
gtgactggag ttcagacgtg tgctcttccg atctcaaatt ttgtgctcac agacct         56

<210> SEQ ID NO 239
<211> LENGTH: 57
<212> TYPE: DNA
<213> ORGANISM: Artificial Sequence
<220> FEATURE:
<223> OTHER INFORMATION: Synthetic

<400> SEQUENCE: 239
acactctttc cctacacgac gctcttccga tctttgccaa catgacttac ttgatcc        57

<210> SEQ ID NO 240
<211> LENGTH: 58
<212> TYPE: DNA
<213> ORGANISM: Artificial Sequence
<220> FEATURE:
<223> OTHER INFORMATION: Synthetic

<400> SEQUENCE: 240
gtgactggag ttcagacgtg tgctcttccg atctccagaa tatttcgtat ggtgccat      58

<210> SEQ ID NO 241
<211> LENGTH: 54
<212> TYPE: DNA
<213> ORGANISM: Artificial Sequence
<220> FEATURE:
<223> OTHER INFORMATION: Synthetic

<400> SEQUENCE: 241
acactctttc cctacacgac gctcttccga tctatgcctc cagttcagga aaat           54
```

```
<210> SEQ ID NO 242
<211> LENGTH: 54
<212> TYPE: DNA
<213> ORGANISM: Artificial Sequence
<220> FEATURE:
<223> OTHER INFORMATION: Synthetic

<400> SEQUENCE: 242
gtgactggag ttcagacgtg tgctcttccg atctttattt ctgccatgcc aaca      54

<210> SEQ ID NO 243
<211> LENGTH: 53
<212> TYPE: DNA
<213> ORGANISM: Artificial Sequence
<220> FEATURE:
<223> OTHER INFORMATION: Synthetic

<400> SEQUENCE: 243
acactctttc cctacacgac gctcttccga tctaagtcct caccttgaga acc       53

<210> SEQ ID NO 244
<211> LENGTH: 52
<212> TYPE: DNA
<213> ORGANISM: Artificial Sequence
<220> FEATURE:
<223> OTHER INFORMATION: Synthetic

<400> SEQUENCE: 244
gtgactggag ttcagacgtg tgctcttccg atctgggctg ggcatcactg ta        52

<210> SEQ ID NO 245
<211> LENGTH: 53
<212> TYPE: DNA
<213> ORGANISM: Artificial Sequence
<220> FEATURE:
<223> OTHER INFORMATION: Synthetic

<400> SEQUENCE: 245
acactctttc cctacacgac gctcttccga tctaggacca gaggaaacct cag       53

<210> SEQ ID NO 246
<211> LENGTH: 62
<212> TYPE: DNA
<213> ORGANISM: Artificial Sequence
<220> FEATURE:
<223> OTHER INFORMATION: Synthetic

<400> SEQUENCE: 246
gtgactggag ttcagacgtg tgctcttccg atctaaatga tcttgacaaa gcaaataaag    60
ac                                                                   62

<210> SEQ ID NO 247
<211> LENGTH: 54
<212> TYPE: DNA
<213> ORGANISM: Artificial Sequence
<220> FEATURE:
<223> OTHER INFORMATION: Synthetic

<400> SEQUENCE: 247
acactctttc cctacacgac gctcttccga tctgtgatct atgcccgtct ctgg       54

<210> SEQ ID NO 248
<211> LENGTH: 58
<212> TYPE: DNA
<213> ORGANISM: Artificial Sequence
<220> FEATURE:
```

<223> OTHER INFORMATION: Synthetic

<400> SEQUENCE: 248
gtgactggag ttcagacgtg tgctcttccg atctgagttg tatcacctgg aattggta        58

<210> SEQ ID NO 249
<211> LENGTH: 57
<212> TYPE: DNA
<213> ORGANISM: Artificial Sequence
<220> FEATURE:
<223> OTHER INFORMATION: Synthetic

<400> SEQUENCE: 249
acactctttc cctacacgac gctcttccga tctactgaga gcactgatga taaacac         57

<210> SEQ ID NO 250
<211> LENGTH: 58
<212> TYPE: DNA
<213> ORGANISM: Artificial Sequence
<220> FEATURE:
<223> OTHER INFORMATION: Synthetic

<400> SEQUENCE: 250
gtgactggag ttcagacgtg tgctcttccg atctaaatgt aagccagtct ttgtgtca        58

<210> SEQ ID NO 251
<211> LENGTH: 53
<212> TYPE: DNA
<213> ORGANISM: Artificial Sequence
<220> FEATURE:
<223> OTHER INFORMATION: Synthetic

<400> SEQUENCE: 251
acactctttc cctacacgac gctcttccga tctttgtcct gcttgcttac ctc             53

<210> SEQ ID NO 252
<211> LENGTH: 58
<212> TYPE: DNA
<213> ORGANISM: Artificial Sequence
<220> FEATURE:
<223> OTHER INFORMATION: Synthetic

<400> SEQUENCE: 252
gtgactggag ttcagacgtg tgctcttccg atctactact caggatagga aaagagaa        58

<210> SEQ ID NO 253
<211> LENGTH: 56
<212> TYPE: DNA
<213> ORGANISM: Artificial Sequence
<220> FEATURE:
<223> OTHER INFORMATION: Synthetic

<400> SEQUENCE: 253
acactctttc cctacacgac gctcttccga tcttgtggat aacacatacc aggtga          56

<210> SEQ ID NO 254
<211> LENGTH: 58
<212> TYPE: DNA
<213> ORGANISM: Artificial Sequence
<220> FEATURE:
<223> OTHER INFORMATION: Synthetic

<400> SEQUENCE: 254
gtgactggag ttcagacgtg tgctcttccg atctctggac attttccac acagtttg         58

```
<210> SEQ ID NO 255
<211> LENGTH: 61
<212> TYPE: DNA
<213> ORGANISM: Artificial Sequence
<220> FEATURE:
<223> OTHER INFORMATION: Synthetic

<400> SEQUENCE: 255
acactctttc cctacacgac gctcttccga tctgtgattt tctaaaatag caggctctta    60
t                                                                   61

<210> SEQ ID NO 256
<211> LENGTH: 52
<212> TYPE: DNA
<213> ORGANISM: Artificial Sequence
<220> FEATURE:
<223> OTHER INFORMATION: Synthetic

<400> SEQUENCE: 256
gtgactggag ttcagacgtg tgctcttccg atctaaaatt tcagccgggc gc            52

<210> SEQ ID NO 257
<211> LENGTH: 56
<212> TYPE: DNA
<213> ORGANISM: Artificial Sequence
<220> FEATURE:
<223> OTHER INFORMATION: Synthetic

<400> SEQUENCE: 257
acactctttc cctacacgac gctcttccga tcttgcttaa ttattctgaa gggccg        56

<210> SEQ ID NO 258
<211> LENGTH: 60
<212> TYPE: DNA
<213> ORGANISM: Artificial Sequence
<220> FEATURE:
<223> OTHER INFORMATION: Synthetic

<400> SEQUENCE: 258
gtgactggag ttcagacgtg tgctcttccg atctcaggtc ttccagatgt gtaatacatt    60

<210> SEQ ID NO 259
<211> LENGTH: 51
<212> TYPE: DNA
<213> ORGANISM: Artificial Sequence
<220> FEATURE:
<223> OTHER INFORMATION: Synthetic

<400> SEQUENCE: 259
acactctttc cctacacgac gctcttccga tctcggtgcg catgtactgg t             51

<210> SEQ ID NO 260
<211> LENGTH: 52
<212> TYPE: DNA
<213> ORGANISM: Artificial Sequence
<220> FEATURE:
<223> OTHER INFORMATION: Synthetic

<400> SEQUENCE: 260
gtgactggag ttcagacgtg tgctcttccg atcttccaac aggcacgtct cc            52

<210> SEQ ID NO 261
<211> LENGTH: 57
<212> TYPE: DNA
<213> ORGANISM: Artificial Sequence
<220> FEATURE:
```

<223> OTHER INFORMATION: Synthetic

<400> SEQUENCE: 261
acactctttc cctacacgac gctcttccga tcttcttcat gatgtttcct tcgtagg     57

<210> SEQ ID NO 262
<211> LENGTH: 55
<212> TYPE: DNA
<213> ORGANISM: Artificial Sequence
<220> FEATURE:
<223> OTHER INFORMATION: Synthetic

<400> SEQUENCE: 262
gtgactggag ttcagacgtg tgctcttccg atctattgaa acactacagc gcagg       55

<210> SEQ ID NO 263
<211> LENGTH: 55
<212> TYPE: DNA
<213> ORGANISM: Artificial Sequence
<220> FEATURE:
<223> OTHER INFORMATION: Synthetic

<400> SEQUENCE: 263
acactctttc cctacacgac gctcttccga tctctccaat gagactctgt cctgc       55

<210> SEQ ID NO 264
<211> LENGTH: 53
<212> TYPE: DNA
<213> ORGANISM: Artificial Sequence
<220> FEATURE:
<223> OTHER INFORMATION: Synthetic

<400> SEQUENCE: 264
gtgactggag ttcagacgtg tgctcttccg atctcgggca agacctccta ctt         53

<210> SEQ ID NO 265
<211> LENGTH: 54
<212> TYPE: DNA
<213> ORGANISM: Artificial Sequence
<220> FEATURE:
<223> OTHER INFORMATION: Synthetic

<400> SEQUENCE: 265
acactctttc cctacacgac gctcttccga tcttctcaac catctgtgag tcca        54

<210> SEQ ID NO 266
<211> LENGTH: 58
<212> TYPE: DNA
<213> ORGANISM: Artificial Sequence
<220> FEATURE:
<223> OTHER INFORMATION: Synthetic

<400> SEQUENCE: 266
gtgactggag ttcagacgtg tgctcttccg atcttggact tttgagatcc tggatgaa    58

<210> SEQ ID NO 267
<211> LENGTH: 60
<212> TYPE: DNA
<213> ORGANISM: Artificial Sequence
<220> FEATURE:
<223> OTHER INFORMATION: Synthetic

<400> SEQUENCE: 267
acactctttc cctacacgac gctcttccga tctcagctgt tacctgtttg aaaaacattt  60

<210> SEQ ID NO 268
<211> LENGTH: 52
<212> TYPE: DNA
<213> ORGANISM: Artificial Sequence
<220> FEATURE:
<223> OTHER INFORMATION: Synthetic

<400> SEQUENCE: 268
gtgactggag ttcagacgtg tgctcttccg atctagatcc aatgctggcc ta    52

<210> SEQ ID NO 269
<211> LENGTH: 51
<212> TYPE: DNA
<213> ORGANISM: Artificial Sequence
<220> FEATURE:
<223> OTHER INFORMATION: Synthetic

<400> SEQUENCE: 269
acactctttc cctacacgac gctcttccga tctccactac attgacggcc c    51

<210> SEQ ID NO 270
<211> LENGTH: 58
<212> TYPE: DNA
<213> ORGANISM: Artificial Sequence
<220> FEATURE:
<223> OTHER INFORMATION: Synthetic

<400> SEQUENCE: 270
gtgactggag ttcagacgtg tgctcttccg atctgtggaa agtgaaggag aacagaac    58

<210> SEQ ID NO 271
<211> LENGTH: 51
<212> TYPE: DNA
<213> ORGANISM: Artificial Sequence
<220> FEATURE:
<223> OTHER INFORMATION: Synthetic

<400> SEQUENCE: 271
acactctttc cctacacgac gctcttccga tctgaccagc gaggatggca g    51

<210> SEQ ID NO 272
<211> LENGTH: 52
<212> TYPE: DNA
<213> ORGANISM: Artificial Sequence
<220> FEATURE:
<223> OTHER INFORMATION: Synthetic

<400> SEQUENCE: 272
gtgactggag ttcagacgtg tgctcttccg atctcactca ggaagctccg gc    52

<210> SEQ ID NO 273
<211> LENGTH: 52
<212> TYPE: DNA
<213> ORGANISM: Artificial Sequence
<220> FEATURE:
<223> OTHER INFORMATION: Synthetic

<400> SEQUENCE: 273
acactctttc cctacacgac gctcttccga tctcaatgtg ctggtgaccg ag    52

<210> SEQ ID NO 274
<211> LENGTH: 53
<212> TYPE: DNA
<213> ORGANISM: Artificial Sequence
<220> FEATURE:
<223> OTHER INFORMATION: Synthetic

<400> SEQUENCE: 274
gtgactggag ttcagacgtg tgctcttccg atctgggtca tgccagtagg acg    53

<210> SEQ ID NO 275
<211> LENGTH: 51
<212> TYPE: DNA
<213> ORGANISM: Artificial Sequence
<220> FEATURE:
<223> OTHER INFORMATION: Synthetic

<400> SEQUENCE: 275
acactctttc cctacacgac gctcttccga tctgggacga ctccgtgttt g    51

<210> SEQ ID NO 276
<211> LENGTH: 52
<212> TYPE: DNA
<213> ORGANISM: Artificial Sequence
<220> FEATURE:
<223> OTHER INFORMATION: Synthetic

<400> SEQUENCE: 276
gtgactggag ttcagacgtg tgctcttccg atctgtgagg ggtccctagc ag    52

<210> SEQ ID NO 277
<211> LENGTH: 51
<212> TYPE: DNA
<213> ORGANISM: Artificial Sequence
<220> FEATURE:
<223> OTHER INFORMATION: Synthetic

<400> SEQUENCE: 277
acactctttc cctacacgac gctcttccga tctcccactg gatgctgcac a    51

<210> SEQ ID NO 278
<211> LENGTH: 56
<212> TYPE: DNA
<213> ORGANISM: Artificial Sequence
<220> FEATURE:
<223> OTHER INFORMATION: Synthetic

<400> SEQUENCE: 278
gtgactggag ttcagacgtg tgctcttccg atctgttgac tgaacttcca aagcac    56

<210> SEQ ID NO 279
<211> LENGTH: 51
<212> TYPE: DNA
<213> ORGANISM: Artificial Sequence
<220> FEATURE:
<223> OTHER INFORMATION: Synthetic

<400> SEQUENCE: 279
acactctttc cctacacgac gctcttccga tctgtcttgt tggcaggggt c    51

<210> SEQ ID NO 280
<211> LENGTH: 52
<212> TYPE: DNA
<213> ORGANISM: Artificial Sequence
<220> FEATURE:
<223> OTHER INFORMATION: Synthetic

<400> SEQUENCE: 280
gtgactggag ttcagacgtg tgctcttccg atcttcatcc acaggtaggg gc    52

<210> SEQ ID NO 281
<211> LENGTH: 61

<212> TYPE: DNA
<213> ORGANISM: Artificial Sequence
<220> FEATURE:
<223> OTHER INFORMATION: Synthetic

<400> SEQUENCE: 281
acactctttc cctacacgac gctcttccga tctcatcagc tgaagatgaa ataggatgta    60
a                                                                   61

<210> SEQ ID NO 282
<211> LENGTH: 54
<212> TYPE: DNA
<213> ORGANISM: Artificial Sequence
<220> FEATURE:
<223> OTHER INFORMATION: Synthetic

<400> SEQUENCE: 282
gtgactggag ttcagacgtg tgctcttccg atctagcacc ctagaaccaa atcc          54

<210> SEQ ID NO 283
<211> LENGTH: 51
<212> TYPE: DNA
<213> ORGANISM: Artificial Sequence
<220> FEATURE:
<223> OTHER INFORMATION: Synthetic

<400> SEQUENCE: 283
acactctttc cctacacgac gctcttccga tctsccagtt gcaaaccaga c             51

<210> SEQ ID NO 284
<211> LENGTH: 54
<212> TYPE: DNA
<213> ORGANISM: Artificial Sequence
<220> FEATURE:
<223> OTHER INFORMATION: Synthetic

<400> SEQUENCE: 284
gtgactggag ttcagacgtg tgctcttccg atctatcagt gaggaatcag aggc          54

<210> SEQ ID NO 285
<211> LENGTH: 52
<212> TYPE: DNA
<213> ORGANISM: Artificial Sequence
<220> FEATURE:
<223> OTHER INFORMATION: Synthetic

<400> SEQUENCE: 285
acactctttc cctacacgac gctcttccga tctgtgtctg tcctgggagt ct            52

<210> SEQ ID NO 286
<211> LENGTH: 52
<212> TYPE: DNA
<213> ORGANISM: Artificial Sequence
<220> FEATURE:
<223> OTHER INFORMATION: Synthetic

<400> SEQUENCE: 286
gtgactggag ttcagacgtg tgctcttccg atctcatccc tgtggaggag ct            52

<210> SEQ ID NO 287
<211> LENGTH: 57
<212> TYPE: DNA
<213> ORGANISM: Artificial Sequence
<220> FEATURE:
<223> OTHER INFORMATION: Synthetic

<400> SEQUENCE: 287
acactctttc cctacacgac gctcttccga tctctgttgt gcttctatta caggctc    57

<210> SEQ ID NO 288
<211> LENGTH: 57
<212> TYPE: DNA
<213> ORGANISM: Artificial Sequence
<220> FEATURE:
<223> OTHER INFORMATION: Synthetic

<400> SEQUENCE: 288
gtgactggag ttcagacgtg tgctcttccg atctaatgat ccttgccaaa gacaact    57

<210> SEQ ID NO 289
<211> LENGTH: 57
<212> TYPE: DNA
<213> ORGANISM: Artificial Sequence
<220> FEATURE:
<223> OTHER INFORMATION: Synthetic

<400> SEQUENCE: 289
acactctttc cctacacgac gctcttccga tctctggctt tgaatcatta gcgttac    57

<210> SEQ ID NO 290
<211> LENGTH: 58
<212> TYPE: DNA
<213> ORGANISM: Artificial Sequence
<220> FEATURE:
<223> OTHER INFORMATION: Synthetic

<400> SEQUENCE: 290
gtgactggag ttcagacgtg tgctcttccg atctcggact cagaaccaca tcataaat    58

<210> SEQ ID NO 291
<211> LENGTH: 60
<212> TYPE: DNA
<213> ORGANISM: Artificial Sequence
<220> FEATURE:
<223> OTHER INFORMATION: Synthetic

<400> SEQUENCE: 291
acactctttc cctacacgac gctcttccga tctaaggttt acacatttta atcccatttt    60

<210> SEQ ID NO 292
<211> LENGTH: 58
<212> TYPE: DNA
<213> ORGANISM: Artificial Sequence
<220> FEATURE:
<223> OTHER INFORMATION: Synthetic

<400> SEQUENCE: 292
gtgactggag ttcagacgtg tgctcttccg atctacattc agcaaacaag ctcaaaac    58

<210> SEQ ID NO 293
<211> LENGTH: 53
<212> TYPE: DNA
<213> ORGANISM: Artificial Sequence
<220> FEATURE:
<223> OTHER INFORMATION: Synthetic

<400> SEQUENCE: 293
acactctttc cctacacgac gctcttccga tctattaggt ggaccacaca gga    53

<210> SEQ ID NO 294
<211> LENGTH: 53

```
<212> TYPE: DNA
<213> ORGANISM: Artificial Sequence
<220> FEATURE:
<223> OTHER INFORMATION: Synthetic

<400> SEQUENCE: 294
gtgactggag ttcagacgtg tgctcttccg atcttaaggt gagccttccc ttc      53

<210> SEQ ID NO 295
<211> LENGTH: 56
<212> TYPE: DNA
<213> ORGANISM: Artificial Sequence
<220> FEATURE:
<223> OTHER INFORMATION: Synthetic

<400> SEQUENCE: 295
acactctttc cctacacgac gctcttccga tctactcgtg ctattttcc tcacag      56

<210> SEQ ID NO 296
<211> LENGTH: 52
<212> TYPE: DNA
<213> ORGANISM: Artificial Sequence
<220> FEATURE:
<223> OTHER INFORMATION: Synthetic

<400> SEQUENCE: 296
gtgactggag ttcagacgtg tgctcttccg atcttacgtg aagaggagcc ag       52

<210> SEQ ID NO 297
<211> LENGTH: 51
<212> TYPE: DNA
<213> ORGANISM: Artificial Sequence
<220> FEATURE:
<223> OTHER INFORMATION: Synthetic

<400> SEQUENCE: 297
acactctttc cctacacgac gctcttccga tctgcctacc tggtcgccat g        51

<210> SEQ ID NO 298
<211> LENGTH: 58
<212> TYPE: DNA
<213> ORGANISM: Artificial Sequence
<220> FEATURE:
<223> OTHER INFORMATION: Synthetic

<400> SEQUENCE: 298
gtgactggag ttcagacgtg tgctcttccg atctcattgg gacttttcca catcttct   58

<210> SEQ ID NO 299
<211> LENGTH: 57
<212> TYPE: DNA
<213> ORGANISM: Artificial Sequence
<220> FEATURE:
<223> OTHER INFORMATION: Synthetic

<400> SEQUENCE: 299
acactctttc cctacacgac gctcttccga tctgacatgt ctttccccac aatcata    57

<210> SEQ ID NO 300
<211> LENGTH: 58
<212> TYPE: DNA
<213> ORGANISM: Artificial Sequence
<220> FEATURE:
<223> OTHER INFORMATION: Synthetic

<400> SEQUENCE: 300
```

```
gtgactggag ttcagacgtg tgctcttccg atctctttca tctgtaaagg accggttc      58
```

<210> SEQ ID NO 301
<211> LENGTH: 57
<212> TYPE: DNA
<213> ORGANISM: Artificial Sequence
<220> FEATURE:
<223> OTHER INFORMATION: Synthetic

<400> SEQUENCE: 301

```
acactctttc cctacacgac gctcttccga tcttactcat aggtgggaaa ctacctc       57
```

<210> SEQ ID NO 302
<211> LENGTH: 53
<212> TYPE: DNA
<213> ORGANISM: Artificial Sequence
<220> FEATURE:
<223> OTHER INFORMATION: Synthetic

<400> SEQUENCE: 302

```
gtgactggag ttcagacgtg tgctcttccg atctcctaac actaagggtg cgt           53
```

<210> SEQ ID NO 303
<211> LENGTH: 55
<212> TYPE: DNA
<213> ORGANISM: Artificial Sequence
<220> FEATURE:
<223> OTHER INFORMATION: Synthetic

<400> SEQUENCE: 303

```
acactctttc cctacacgac gctcttccga tctcttcctg gaggactact tcacg         55
```

<210> SEQ ID NO 304
<211> LENGTH: 52
<212> TYPE: DNA
<213> ORGANISM: Artificial Sequence
<220> FEATURE:
<223> OTHER INFORMATION: Synthetic

<400> SEQUENCE: 304

```
gtgactggag ttcagacgtg tgctcttccg atctctctgc ctgcctgctg tt            52
```

<210> SEQ ID NO 305
<211> LENGTH: 61
<212> TYPE: DNA
<213> ORGANISM: Artificial Sequence
<220> FEATURE:
<223> OTHER INFORMATION: Synthetic

<400> SEQUENCE: 305

```
acactctttc cctacacgac gctcttccga tctatctagg atccaaattt tagaagtcaa    60
g                                                                    61
```

<210> SEQ ID NO 306
<211> LENGTH: 62
<212> TYPE: DNA
<213> ORGANISM: Artificial Sequence
<220> FEATURE:
<223> OTHER INFORMATION: Synthetic

<400> SEQUENCE: 306

```
gtgactggag ttcagacgtg tgctcttccg atcttcatct tgtactggag aaaattcttg    60
tg                                                                   62
```

<210> SEQ ID NO 307
<211> LENGTH: 53
<212> TYPE: DNA
<213> ORGANISM: Artificial Sequence
<220> FEATURE:
<223> OTHER INFORMATION: Synthetic

<400> SEQUENCE: 307
acactctttc cctacacgac gctcttccga tctcactgcc ggttgtcaat ctc    53

<210> SEQ ID NO 308
<211> LENGTH: 52
<212> TYPE: DNA
<213> ORGANISM: Artificial Sequence
<220> FEATURE:
<223> OTHER INFORMATION: Synthetic

<400> SEQUENCE: 308
gtgactggag ttcagacgtg tgctcttccg atcttgacgc cacagtcagg ac    52

<210> SEQ ID NO 309
<211> LENGTH: 61
<212> TYPE: DNA
<213> ORGANISM: Artificial Sequence
<220> FEATURE:
<223> OTHER INFORMATION: Synthetic

<400> SEQUENCE: 309
acactctttc cctacacgac gctcttccga tcttcacctt ctttctaacc ttttcttatg    60
t    61

<210> SEQ ID NO 310
<211> LENGTH: 62
<212> TYPE: DNA
<213> ORGANISM: Artificial Sequence
<220> FEATURE:
<223> OTHER INFORMATION: Synthetic

<400> SEQUENCE: 310
gtgactggag ttcagacgtg tgctcttccg atctaaacgt gattcattta tttgttcaaa    60
gc    62

<210> SEQ ID NO 311
<211> LENGTH: 53
<212> TYPE: DNA
<213> ORGANISM: Artificial Sequence
<220> FEATURE:
<223> OTHER INFORMATION: Synthetic

<400> SEQUENCE: 311
acactctttc cctacacgac gctcttccga tctgatgctc actgtgtgtt gct    53

<210> SEQ ID NO 312
<211> LENGTH: 54
<212> TYPE: DNA
<213> ORGANISM: Artificial Sequence
<220> FEATURE:
<223> OTHER INFORMATION: Synthetic

<400> SEQUENCE: 312
gtgactggag ttcagacgtg tgctcttccg atctaataat tggggtccct ccct    54

<210> SEQ ID NO 313
<211> LENGTH: 51
<212> TYPE: DNA

```
<213> ORGANISM: Artificial Sequence
<220> FEATURE:
<223> OTHER INFORMATION: Synthetic

<400> SEQUENCE: 313
acactctttc cctacacgac gctcttccga tctcgcagcc tgtacccagt g          51

<210> SEQ ID NO 314
<211> LENGTH: 53
<212> TYPE: DNA
<213> ORGANISM: Artificial Sequence
<220> FEATURE:
<223> OTHER INFORMATION: Synthetic

<400> SEQUENCE: 314
gtgactggag ttcagacgtg tgctcttccg atcttgctac cacaagtttg ccc        53

<210> SEQ ID NO 315
<211> LENGTH: 55
<212> TYPE: DNA
<213> ORGANISM: Artificial Sequence
<220> FEATURE:
<223> OTHER INFORMATION: Synthetic

<400> SEQUENCE: 315
acactctttc cctacacgac gctcttccga tctgctacga cccagttacc atagc      55

<210> SEQ ID NO 316
<211> LENGTH: 60
<212> TYPE: DNA
<213> ORGANISM: Artificial Sequence
<220> FEATURE:
<223> OTHER INFORMATION: Synthetic

<400> SEQUENCE: 316
gtgactggag ttcagacgtg tgctcttccg atctagctac ctgttaaaga atcatctgga 60

<210> SEQ ID NO 317
<211> LENGTH: 56
<212> TYPE: DNA
<213> ORGANISM: Artificial Sequence
<220> FEATURE:
<223> OTHER INFORMATION: Synthetic

<400> SEQUENCE: 317
acactctttc cctacacgac gctcttccga tctgaggtga cattttcaaa gcagtg     56

<210> SEQ ID NO 318
<211> LENGTH: 62
<212> TYPE: DNA
<213> ORGANISM: Artificial Sequence
<220> FEATURE:
<223> OTHER INFORMATION: Synthetic

<400> SEQUENCE: 318
gtgactggag ttcagacgtg tgctcttccg atctaaatat agcactactt acaaacttag 60
gg                                                                62

<210> SEQ ID NO 319
<211> LENGTH: 59
<212> TYPE: DNA
<213> ORGANISM: Artificial Sequence
<220> FEATURE:
<223> OTHER INFORMATION: Synthetic

<400> SEQUENCE: 319
```

```
acactctttc cctacacgac gctcttccga tctaaagtgg ctaaagttga tctgattgt        59

<210> SEQ ID NO 320
<211> LENGTH: 52
<212> TYPE: DNA
<213> ORGANISM: Artificial Sequence
<220> FEATURE:
<223> OTHER INFORMATION: Synthetic

<400> SEQUENCE: 320
gtgactggag ttcagacgtg tgctcttccg atctgtcctg agcagcmtcc ag              52

<210> SEQ ID NO 321
<211> LENGTH: 57
<212> TYPE: DNA
<213> ORGANISM: Artificial Sequence
<220> FEATURE:
<223> OTHER INFORMATION: Synthetic

<400> SEQUENCE: 321
acactctttc cctacacgac gctcttccga tctccttagt ctttctttga agcagca         57

<210> SEQ ID NO 322
<211> LENGTH: 58
<212> TYPE: DNA
<213> ORGANISM: Artificial Sequence
<220> FEATURE:
<223> OTHER INFORMATION: Synthetic

<400> SEQUENCE: 322
gtgactggag ttcagacgtg tgctcttccg atctcctttc tcagagcatc tgtttttg       58

<210> SEQ ID NO 323
<211> LENGTH: 57
<212> TYPE: DNA
<213> ORGANISM: Artificial Sequence
<220> FEATURE:
<223> OTHER INFORMATION: Synthetic

<400> SEQUENCE: 323
acactctttc cctacacgac gctcttccga tctataactc attcatcgcc acatagg         57

<210> SEQ ID NO 324
<211> LENGTH: 58
<212> TYPE: DNA
<213> ORGANISM: Artificial Sequence
<220> FEATURE:
<223> OTHER INFORMATION: Synthetic

<400> SEQUENCE: 324
gtgactggag ttcagacgtg tgctcttccg atcttgaatg gtgtctgcat aacaaagg       58

<210> SEQ ID NO 325
<211> LENGTH: 53
<212> TYPE: DNA
<213> ORGANISM: Artificial Sequence
<220> FEATURE:
<223> OTHER INFORMATION: Synthetic

<400> SEQUENCE: 325
acactctttc cctacacgac gctcttccga tctgtctctg tgttcttgtc ccc             53

<210> SEQ ID NO 326
<211> LENGTH: 55
<212> TYPE: DNA
```

```
<213> ORGANISM: Artificial Sequence
<220> FEATURE:
<223> OTHER INFORMATION: Synthetic

<400> SEQUENCE: 326
gtgactggag ttcagacgtg tgctcttccg atcttgtata aggtaaggtc cctgg        55

<210> SEQ ID NO 327
<211> LENGTH: 56
<212> TYPE: DNA
<213> ORGANISM: Artificial Sequence
<220> FEATURE:
<223> OTHER INFORMATION: Synthetic

<400> SEQUENCE: 327
acactctttc cctacacgac gctcttccga tctcatccat ggaggagttg aagttt       56

<210> SEQ ID NO 328
<211> LENGTH: 54
<212> TYPE: DNA
<213> ORGANISM: Artificial Sequence
<220> FEATURE:
<223> OTHER INFORMATION: Synthetic

<400> SEQUENCE: 328
gtgactggag ttcagacgtg tgctcttccg atcttcaggt gctcactaga gctc         54

<210> SEQ ID NO 329
<211> LENGTH: 57
<212> TYPE: DNA
<213> ORGANISM: Artificial Sequence
<220> FEATURE:
<223> OTHER INFORMATION: Synthetic

<400> SEQUENCE: 329
acactctttc cctacacgac gctcttccga tctctcttgt tcgttccttg tactgag      57

<210> SEQ ID NO 330
<211> LENGTH: 54
<212> TYPE: DNA
<213> ORGANISM: Artificial Sequence
<220> FEATURE:
<223> OTHER INFORMATION: Synthetic

<400> SEQUENCE: 330
gtgactggag ttcagacgtg tgctcttccg atctaggaga ctggacatcg tcag         54

<210> SEQ ID NO 331
<211> LENGTH: 53
<212> TYPE: DNA
<213> ORGANISM: Artificial Sequence
<220> FEATURE:
<223> OTHER INFORMATION: Synthetic

<400> SEQUENCE: 331
acactctttc cctacacgac gctcttccga tctaggcycc atttacatca tca          53

<210> SEQ ID NO 332
<211> LENGTH: 56
<212> TYPE: DNA
<213> ORGANISM: Artificial Sequence
<220> FEATURE:
<223> OTHER INFORMATION: Synthetic

<400> SEQUENCE: 332
gtgactggag ttcagacgtg tgctcttccg atctcaccca gagaagccaa agaaag       56
```

<210> SEQ ID NO 333
<211> LENGTH: 61
<212> TYPE: DNA
<213> ORGANISM: Artificial Sequence
<220> FEATURE:
<223> OTHER INFORMATION: Synthetic

<400> SEQUENCE: 333
acactctttc cctacacgac gctcttccga tctataggaa gtagaggaaa gtattcttca    60
g    61

<210> SEQ ID NO 334
<211> LENGTH: 58
<212> TYPE: DNA
<213> ORGANISM: Artificial Sequence
<220> FEATURE:
<223> OTHER INFORMATION: Synthetic

<400> SEQUENCE: 334
gtgactggag ttcagacgtg tgctcttccg atctccaggt acagtaagta ggtcatgt    58

<210> SEQ ID NO 335
<211> LENGTH: 51
<212> TYPE: DNA
<213> ORGANISM: Artificial Sequence
<220> FEATURE:
<223> OTHER INFORMATION: Synthetic

<400> SEQUENCE: 335
acactctttc cctacacgac gctcttccga tctcacccct acacttggct g    51

<210> SEQ ID NO 336
<211> LENGTH: 53
<212> TYPE: DNA
<213> ORGANISM: Artificial Sequence
<220> FEATURE:
<223> OTHER INFORMATION: Synthetic

<400> SEQUENCE: 336
gtgactggag ttcagacgtg tgctcttccg atctctggta accagcccat cag    53

<210> SEQ ID NO 337
<211> LENGTH: 53
<212> TYPE: DNA
<213> ORGANISM: Artificial Sequence
<220> FEATURE:
<223> OTHER INFORMATION: Synthetic

<400> SEQUENCE: 337
acactctttc cctacacgac gctcttccga tctctcccct cgaaatgaag cta    53

<210> SEQ ID NO 338
<211> LENGTH: 52
<212> TYPE: DNA
<213> ORGANISM: Artificial Sequence
<220> FEATURE:
<223> OTHER INFORMATION: Synthetic

<400> SEQUENCE: 338
gtgactggag ttcagacgtg tgctcttccg atctgggagc ctcatccctc tg    52

<210> SEQ ID NO 339
<211> LENGTH: 54
<212> TYPE: DNA

<213> ORGANISM: Artificial Sequence
<220> FEATURE:
<223> OTHER INFORMATION: Synthetic

<400> SEQUENCE: 339
acactctttc cctacacgac gctcttccga tctccaggct cacctctata gtgg    54

<210> SEQ ID NO 340
<211> LENGTH: 55
<212> TYPE: DNA
<213> ORGANISM: Artificial Sequence
<220> FEATURE:
<223> OTHER INFORMATION: Synthetic

<400> SEQUENCE: 340
gtgactggag ttcagacgtg tgctcttccg atctcaccac cagcttatat tccgt    55

<210> SEQ ID NO 341
<211> LENGTH: 52
<212> TYPE: DNA
<213> ORGANISM: Artificial Sequence
<220> FEATURE:
<223> OTHER INFORMATION: Synthetic

<400> SEQUENCE: 341
acactctttc cctacacgac gctcttccga tctcctctca gcgtacccett gt    52

<210> SEQ ID NO 342
<211> LENGTH: 52
<212> TYPE: DNA
<213> ORGANISM: Artificial Sequence
<220> FEATURE:
<223> OTHER INFORMATION: Synthetic

<400> SEQUENCE: 342
gtgactggag ttcagacgtg tgctcttccg atctggtgca gctggtgaca ca    52

<210> SEQ ID NO 343
<211> LENGTH: 56
<212> TYPE: DNA
<213> ORGANISM: Artificial Sequence
<220> FEATURE:
<223> OTHER INFORMATION: Synthetic

<400> SEQUENCE: 343
acactctttc cctacacgac gctcttccga tctatacaat gccacctgaa tacagg    56

<210> SEQ ID NO 344
<211> LENGTH: 55
<212> TYPE: DNA
<213> ORGANISM: Artificial Sequence
<220> FEATURE:
<223> OTHER INFORMATION: Synthetic

<400> SEQUENCE: 344
gtgactggag ttcagacgtg tgctcttccg atctgtgcca gcaatagatg ctaga    55

<210> SEQ ID NO 345
<211> LENGTH: 57
<212> TYPE: DNA
<213> ORGANISM: Artificial Sequence
<220> FEATURE:
<223> OTHER INFORMATION: Synthetic

<400> SEQUENCE: 345
acactctttc cctacacgac gctcttccga tctctcctgc catcatattg aacacag    57

<210> SEQ ID NO 346
<211> LENGTH: 57
<212> TYPE: DNA
<213> ORGANISM: Artificial Sequence
<220> FEATURE:
<223> OTHER INFORMATION: Synthetic

<400> SEQUENCE: 346
gtgactggag ttcagacgtg tgctcttccg atcttgcaga gggagaaaca gaaaaac    57

<210> SEQ ID NO 347
<211> LENGTH: 54
<212> TYPE: DNA
<213> ORGANISM: Artificial Sequence
<220> FEATURE:
<223> OTHER INFORMATION: Synthetic

<400> SEQUENCE: 347
acactctttc cctacacgac gctcttccga tctgtagagc atgacccatg agtg    54

<210> SEQ ID NO 348
<211> LENGTH: 55
<212> TYPE: DNA
<213> ORGANISM: Artificial Sequence
<220> FEATURE:
<223> OTHER INFORMATION: Synthetic

<400> SEQUENCE: 348
gtgactggag ttcagacgtg tgctcttccg atctatggac atgaaacctg gagtt    55

<210> SEQ ID NO 349
<211> LENGTH: 57
<212> TYPE: DNA
<213> ORGANISM: Artificial Sequence
<220> FEATURE:
<223> OTHER INFORMATION: Synthetic

<400> SEQUENCE: 349
acactctttc cctacacgac gctcttccga tctgttcttc ctcagacatt caaacgt    57

<210> SEQ ID NO 350
<211> LENGTH: 58
<212> TYPE: DNA
<213> ORGANISM: Artificial Sequence
<220> FEATURE:
<223> OTHER INFORMATION: Synthetic

<400> SEQUENCE: 350
gtgactggag ttcagacgtg tgctcttccg atctccaggg taggtcaaaa gtatcctt    58

<210> SEQ ID NO 351
<211> LENGTH: 54
<212> TYPE: DNA
<213> ORGANISM: Artificial Sequence
<220> FEATURE:
<223> OTHER INFORMATION: Synthetic

<400> SEQUENCE: 351
acactctttc cctacacgac gctcttccga tcttaccaga tggatgtgaa cccc    54

<210> SEQ ID NO 352
<211> LENGTH: 57
<212> TYPE: DNA
<213> ORGANISM: Artificial Sequence
<220> FEATURE:

<223> OTHER INFORMATION: Synthetic

<400> SEQUENCE: 352
gtgactggag ttcagacgtg tgctcttccg atctggagta tcccatcttg gagagtc      57

<210> SEQ ID NO 353
<211> LENGTH: 60
<212> TYPE: DNA
<213> ORGANISM: Artificial Sequence
<220> FEATURE:
<223> OTHER INFORMATION: Synthetic

<400> SEQUENCE: 353
acactctttc cctacacgac gctcttccga tctttgccat tttggatata ttccttacct   60

<210> SEQ ID NO 354
<211> LENGTH: 58
<212> TYPE: DNA
<213> ORGANISM: Artificial Sequence
<220> FEATURE:
<223> OTHER INFORMATION: Synthetic

<400> SEQUENCE: 354
gtgactggag ttcagacgtg tgctcttccg atctttgtcc cacgaataat gcgtaaat     58

<210> SEQ ID NO 355
<211> LENGTH: 55
<212> TYPE: DNA
<213> ORGANISM: Artificial Sequence
<220> FEATURE:
<223> OTHER INFORMATION: Synthetic

<400> SEQUENCE: 355
acactctttc cctacacgac gctcttccga tctacttggt tgtgtcgatc tctct        55

<210> SEQ ID NO 356
<211> LENGTH: 56
<212> TYPE: DNA
<213> ORGANISM: Artificial Sequence
<220> FEATURE:
<223> OTHER INFORMATION: Synthetic

<400> SEQUENCE: 356
gtgactggag ttcagacgtg tgctcttccg atcttcttca atcccaccac ggtaat       56

<210> SEQ ID NO 357
<211> LENGTH: 51
<212> TYPE: DNA
<213> ORGANISM: Artificial Sequence
<220> FEATURE:
<223> OTHER INFORMATION: Synthetic

<400> SEQUENCE: 357
acactctttc cctacacgac gctcttccga tctagacacc aaggaccggt g            51

<210> SEQ ID NO 358
<211> LENGTH: 58
<212> TYPE: DNA
<213> ORGANISM: Artificial Sequence
<220> FEATURE:
<223> OTHER INFORMATION: Synthetic

<400> SEQUENCE: 358
gtgactggag ttcagacgtg tgctcttccg atctacatcg aggatgacat catctaca     58

```
<210> SEQ ID NO 359
<211> LENGTH: 57
<212> TYPE: DNA
<213> ORGANISM: Artificial Sequence
<220> FEATURE:
<223> OTHER INFORMATION: Synthetic

<400> SEQUENCE: 359
acactctttc cctacacgac gctcttccga tcttcaagta cttacccact gaaaagc      57

<210> SEQ ID NO 360
<211> LENGTH: 54
<212> TYPE: DNA
<213> ORGANISM: Artificial Sequence
<220> FEATURE:
<223> OTHER INFORMATION: Synthetic

<400> SEQUENCE: 360
gtgactggag ttcagacgtg tgctcttccg atcttgcagc tccttggtga gtaa         54

<210> SEQ ID NO 361
<211> LENGTH: 57
<212> TYPE: DNA
<213> ORGANISM: Artificial Sequence
<220> FEATURE:
<223> OTHER INFORMATION: Synthetic

<400> SEQUENCE: 361
acactctttc cctacacgac gctcttccga tctagctcat ttttgttaat ggtggct      57

<210> SEQ ID NO 362
<211> LENGTH: 62
<212> TYPE: DNA
<213> ORGANISM: Artificial Sequence
<220> FEATURE:
<223> OTHER INFORMATION: Synthetic

<400> SEQUENCE: 362
gtgactggag ttcagacgtg tgctcttccg atcttgcttg caaatatctt ctaaaacaac   60
ta                                                                  62

<210> SEQ ID NO 363
<211> LENGTH: 56
<212> TYPE: DNA
<213> ORGANISM: Artificial Sequence
<220> FEATURE:
<223> OTHER INFORMATION: Synthetic

<400> SEQUENCE: 363
acactctttc cctacacgac gctcttccga tcttgataaa tkagcagtca gcagaa       56

<210> SEQ ID NO 364
<211> LENGTH: 56
<212> TYPE: DNA
<213> ORGANISM: Artificial Sequence
<220> FEATURE:
<223> OTHER INFORMATION: Synthetic

<400> SEQUENCE: 364
gtgactggag ttcagacgtg tgctcttccg atctcatgga atgttgtttg cctacc       56

<210> SEQ ID NO 365
<211> LENGTH: 57
<212> TYPE: DNA
<213> ORGANISM: Artificial Sequence
<220> FEATURE:
```

<223> OTHER INFORMATION: Synthetic

<400> SEQUENCE: 365
acactctttc cctacacgac gctcttccga tctttctta ttcccacagt gtatcgg          57

<210> SEQ ID NO 366
<211> LENGTH: 58
<212> TYPE: DNA
<213> ORGANISM: Artificial Sequence
<220> FEATURE:
<223> OTHER INFORMATION: Synthetic

<400> SEQUENCE: 366
gtgactggag ttcagacgtg tgctcttccg atctcctgca gaatgagtat gaactcat       58

<210> SEQ ID NO 367
<211> LENGTH: 57
<212> TYPE: DNA
<213> ORGANISM: Artificial Sequence
<220> FEATURE:
<223> OTHER INFORMATION: Synthetic

<400> SEQUENCE: 367
acactctttc cctacacgac gctcttccga tctagcttta aaagttctgc ttcctca         57

<210> SEQ ID NO 368
<211> LENGTH: 57
<212> TYPE: DNA
<213> ORGANISM: Artificial Sequence
<220> FEATURE:
<223> OTHER INFORMATION: Synthetic

<400> SEQUENCE: 368
gtgactggag ttcagacgtg tgctcttccg atctcaccat tccactgcag aagaaat        57

<210> SEQ ID NO 369
<211> LENGTH: 57
<212> TYPE: DNA
<213> ORGANISM: Artificial Sequence
<220> FEATURE:
<223> OTHER INFORMATION: Synthetic

<400> SEQUENCE: 369
acactctttc cctacacgac gctcttccga tctttcctca aaagagaaat cacgcat         57

<210> SEQ ID NO 370
<211> LENGTH: 62
<212> TYPE: DNA
<213> ORGANISM: Artificial Sequence
<220> FEATURE:
<223> OTHER INFORMATION: Synthetic

<400> SEQUENCE: 370
gtgactggag ttcagacgtg tgctcttccg atctaaatat gtactacgaa aattcctatg    60
cc                                                                     62

<210> SEQ ID NO 371
<211> LENGTH: 52
<212> TYPE: DNA
<213> ORGANISM: Artificial Sequence
<220> FEATURE:
<223> OTHER INFORMATION: Synthetic

<400> SEQUENCE: 371
acactctttc cctacacgac gctcttccga tctaagatca tctgctggcc gt              52

<210> SEQ ID NO 372
<211> LENGTH: 52
<212> TYPE: DNA
<213> ORGANISM: Artificial Sequence
<220> FEATURE:
<223> OTHER INFORMATION: Synthetic

<400> SEQUENCE: 372
gtgactggag ttcagacgtg tgctcttccg atctccagcc tctcgggtac at    52

<210> SEQ ID NO 373
<211> LENGTH: 51
<212> TYPE: DNA
<213> ORGANISM: Artificial Sequence
<220> FEATURE:
<223> OTHER INFORMATION: Synthetic

<400> SEQUENCE: 373
acactctttc cctacacgac gctcttccga tctagaggca agcagaggct g    51

<210> SEQ ID NO 374
<211> LENGTH: 55
<212> TYPE: DNA
<213> ORGANISM: Artificial Sequence
<220> FEATURE:
<223> OTHER INFORMATION: Synthetic

<400> SEQUENCE: 374
gtgactggag ttcagacgtg tgctcttccg atctacctag gagataacac aggcc    55

<210> SEQ ID NO 375
<211> LENGTH: 53
<212> TYPE: DNA
<213> ORGANISM: Artificial Sequence
<220> FEATURE:
<223> OTHER INFORMATION: Synthetic

<400> SEQUENCE: 375
acactctttc cctacacgac gctcttccga tctagagaac gcggaattgg tct    53

<210> SEQ ID NO 376
<211> LENGTH: 56
<212> TYPE: DNA
<213> ORGANISM: Artificial Sequence
<220> FEATURE:
<223> OTHER INFORMATION: Synthetic

<400> SEQUENCE: 376
gtgactggag ttcagacgtg tgctcttccg atctagccat tcatacctct caggaa    56

<210> SEQ ID NO 377
<211> LENGTH: 57
<212> TYPE: DNA
<213> ORGANISM: Artificial Sequence
<220> FEATURE:
<223> OTHER INFORMATION: Synthetic

<400> SEQUENCE: 377
acactctttc cctacacgac gctcttccga tctcttttty cttcctaagg ttgcaca    57

<210> SEQ ID NO 378
<211> LENGTH: 52
<212> TYPE: DNA
<213> ORGANISM: Artificial Sequence
<220> FEATURE:

<223> OTHER INFORMATION: Synthetic

<400> SEQUENCE: 378
gtgactggag ttcagacgtg tgctcttccg atctcgtgca cctggagatg ct    52

<210> SEQ ID NO 379
<211> LENGTH: 56
<212> TYPE: DNA
<213> ORGANISM: Artificial Sequence
<220> FEATURE:
<223> OTHER INFORMATION: Synthetic

<400> SEQUENCE: 379
acactctttc cctacacgac gctcttccga tcttcttgta tctcctcagg gaacag    56

<210> SEQ ID NO 380
<211> LENGTH: 56
<212> TYPE: DNA
<213> ORGANISM: Artificial Sequence
<220> FEATURE:
<223> OTHER INFORMATION: Synthetic

<400> SEQUENCE: 380
gtgactggag ttcagacgtg tgctcttccg atctagacaa gaagagaacc ttcccc    56

<210> SEQ ID NO 381
<211> LENGTH: 53
<212> TYPE: DNA
<213> ORGANISM: Artificial Sequence
<220> FEATURE:
<223> OTHER INFORMATION: Synthetic

<400> SEQUENCE: 381
acactctttc cctacacgac gctcttccga tcttacatgg gtgcttccca ttc    53

<210> SEQ ID NO 382
<211> LENGTH: 53
<212> TYPE: DNA
<213> ORGANISM: Artificial Sequence
<220> FEATURE:
<223> OTHER INFORMATION: Synthetic

<400> SEQUENCE: 382
gtgactggag ttcagacgtg tgctcttccg atctggggca aggttaggtg aag    53

<210> SEQ ID NO 383
<211> LENGTH: 57
<212> TYPE: DNA
<213> ORGANISM: Artificial Sequence
<220> FEATURE:
<223> OTHER INFORMATION: Synthetic

<400> SEQUENCE: 383
acactctttc cctacacgac gctcttccga tcttacaaag tggttctgga ttagctg    57

<210> SEQ ID NO 384
<211> LENGTH: 58
<212> TYPE: DNA
<213> ORGANISM: Artificial Sequence
<220> FEATURE:
<223> OTHER INFORMATION: Synthetic

<400> SEQUENCE: 384
gtgactggag ttcagacgtg tgctcttccg atctgcgagc cacatctaca gtacttta    58

```
<210> SEQ ID NO 385
<211> LENGTH: 52
<212> TYPE: DNA
<213> ORGANISM: Artificial Sequence
<220> FEATURE:
<223> OTHER INFORMATION: Synthetic

<400> SEQUENCE: 385
acactctttc cctacacgac gctcttccga tctcatgtct ttgcagccga gg          52

<210> SEQ ID NO 386
<211> LENGTH: 52
<212> TYPE: DNA
<213> ORGANISM: Artificial Sequence
<220> FEATURE:
<223> OTHER INFORMATION: Synthetic

<400> SEQUENCE: 386
gtgactggag ttcagacgtg tgctcttccg atctccaaga aaggcctggg ct          52

<210> SEQ ID NO 387
<211> LENGTH: 58
<212> TYPE: DNA
<213> ORGANISM: Artificial Sequence
<220> FEATURE:
<223> OTHER INFORMATION: Synthetic

<400> SEQUENCE: 387
acactctttc cctacacgac gctcttccga tctggtgatc tattttttccc tttctccc          58

<210> SEQ ID NO 388
<211> LENGTH: 56
<212> TYPE: DNA
<213> ORGANISM: Artificial Sequence
<220> FEATURE:
<223> OTHER INFORMATION: Synthetic

<400> SEQUENCE: 388
gtgactggag ttcagacgtg tgctcttccg atctagaaac aggctgagtt ttggtc      56

<210> SEQ ID NO 389
<211> LENGTH: 56
<212> TYPE: DNA
<213> ORGANISM: Artificial Sequence
<220> FEATURE:
<223> OTHER INFORMATION: Synthetic

<400> SEQUENCE: 389
acactctttc cctacacgac gctcttccga tcttagacaa ggtcttcctt ccactt      56

<210> SEQ ID NO 390
<211> LENGTH: 56
<212> TYPE: DNA
<213> ORGANISM: Artificial Sequence
<220> FEATURE:
<223> OTHER INFORMATION: Synthetic

<400> SEQUENCE: 390
gtgactggag ttcagacgtg tgctcttccg atcttcctcc tccatacagg aaacag      56

<210> SEQ ID NO 391
<211> LENGTH: 53
<212> TYPE: DNA
<213> ORGANISM: Artificial Sequence
<220> FEATURE:
<223> OTHER INFORMATION: Synthetic
```

```
<400> SEQUENCE: 391
acactctttc cctacacgac gctcttccga tctttctcaa tgatgcttgg ctc              53

<210> SEQ ID NO 392
<211> LENGTH: 55
<212> TYPE: DNA
<213> ORGANISM: Artificial Sequence
<220> FEATURE:
<223> OTHER INFORMATION: Synthetic

<400> SEQUENCE: 392
gtgactggag ttcagacgtg tgctcttccg atcttggctg gacaacaaaa atgga           55

<210> SEQ ID NO 393
<211> LENGTH: 55
<212> TYPE: DNA
<213> ORGANISM: Artificial Sequence
<220> FEATURE:
<223> OTHER INFORMATION: Synthetic

<400> SEQUENCE: 393
caagcagaag acggcatacg agatcgcgac tgaagtgact ggagttcaga cgtgt           55

<210> SEQ ID NO 394
<211> LENGTH: 55
<212> TYPE: DNA
<213> ORGANISM: Artificial Sequence
<220> FEATURE:
<223> OTHER INFORMATION: Synthetic

<400> SEQUENCE: 394
caagcagaag acggcatacg agatagcatc gatagtgact ggagttcaga cgtgt           55

<210> SEQ ID NO 395
<211> LENGTH: 55
<212> TYPE: DNA
<213> ORGANISM: Artificial Sequence
<220> FEATURE:
<223> OTHER INFORMATION: Synthetic

<400> SEQUENCE: 395
caagcagaag acggcatacg agatcgacac atgggtgact ggagttcaga cgtgt           55

<210> SEQ ID NO 396
<211> LENGTH: 55
<212> TYPE: DNA
<213> ORGANISM: Artificial Sequence
<220> FEATURE:
<223> OTHER INFORMATION: Synthetic

<400> SEQUENCE: 396
caagcagaag acggcatacg agatcgacta cgcagtgact ggagttcaga cgtgt           55

<210> SEQ ID NO 397
<211> LENGTH: 55
<212> TYPE: DNA
<213> ORGANISM: Artificial Sequence
<220> FEATURE:
<223> OTHER INFORMATION: Synthetic

<400> SEQUENCE: 397
caagcagaag acggcatacg agatcactgc tgaggtgact ggagttcaga cgtgt           55

<210> SEQ ID NO 398
<211> LENGTH: 55
```

```
<212> TYPE: DNA
<213> ORGANISM: Artificial Sequence
<220> FEATURE:
<223> OTHER INFORMATION: Synthetic

<400> SEQUENCE: 398
caagcagaag acggcatacg agattcgctg tacagtgact ggagttcaga cgtgt       55

<210> SEQ ID NO 399
<211> LENGTH: 55
<212> TYPE: DNA
<213> ORGANISM: Artificial Sequence
<220> FEATURE:
<223> OTHER INFORMATION: Synthetic

<400> SEQUENCE: 399
caagcagaag acggcatacg agatcgctgc agtagtgact ggagttcaga cgtgt       55

<210> SEQ ID NO 400
<211> LENGTH: 55
<212> TYPE: DNA
<213> ORGANISM: Artificial Sequence
<220> FEATURE:
<223> OTHER INFORMATION: Synthetic

<400> SEQUENCE: 400
caagcagaag acggcatacg agatagactt gcaggtgact ggagttcaga cgtgt       55

<210> SEQ ID NO 401
<211> LENGTH: 45
<212> TYPE: DNA
<213> ORGANISM: Artificial Sequence
<220> FEATURE:
<223> OTHER INFORMATION: Synthetic

<400> SEQUENCE: 401
aatgatacgg cgaccaccga gatctacact ctttccctac acgac                 45

<210> SEQ ID NO 402
<211> LENGTH: 40
<212> TYPE: DNA
<213> ORGANISM: Artificial Sequence
<220> FEATURE:
<223> OTHER INFORMATION: Synthetic

<400> SEQUENCE: 402
caggaaacag ctatgaccgt ggagaagctc ccaaccaagc                        40

<210> SEQ ID NO 403
<211> LENGTH: 34
<212> TYPE: DNA
<213> ORGANISM: Artificial Sequence
<220> FEATURE:
<223> OTHER INFORMATION: Synthetic

<400> SEQUENCE: 403
tgtaaaacga cggccagtcg aacgcaccgg agct                              34

<210> SEQ ID NO 404
<211> LENGTH: 46
<212> TYPE: DNA
<213> ORGANISM: Artificial Sequence
<220> FEATURE:
<223> OTHER INFORMATION: Synthetic

<400> SEQUENCE: 404
```

```
tgtaaaacga cggccagtga aagttaaaat tcccgtcgct atcaaa               46

<210> SEQ ID NO 405
<211> LENGTH: 39
<212> TYPE: DNA
<213> ORGANISM: Artificial Sequence
<220> FEATURE:
<223> OTHER INFORMATION: Synthetic

<400> SEQUENCE: 405
caggaaacag ctatgaccgg cctgaggttc agagccatg                      39

<210> SEQ ID NO 406
<211> LENGTH: 40
<212> TYPE: DNA
<213> ORGANISM: Artificial Sequence
<220> FEATURE:
<223> OTHER INFORMATION: Synthetic

<400> SEQUENCE: 406
caggaaacag ctatgaccga agccacactg acgtgcctct                     40

<210> SEQ ID NO 407
<211> LENGTH: 40
<212> TYPE: DNA
<213> ORGANISM: Artificial Sequence
<220> FEATURE:
<223> OTHER INFORMATION: Synthetic

<400> SEQUENCE: 407
tgtaaaacga cggccagtgg cacgtggggg ttgtccacga                     40

<210> SEQ ID NO 408
<211> LENGTH: 40
<212> TYPE: DNA
<213> ORGANISM: Artificial Sequence
<220> FEATURE:
<223> OTHER INFORMATION: Synthetic

<400> SEQUENCE: 408
caggaaacag ctatgaccca gccaggaacg tactggtgaa                     40

<210> SEQ ID NO 409
<211> LENGTH: 37
<212> TYPE: DNA
<213> ORGANISM: Artificial Sequence
<220> FEATURE:
<223> OTHER INFORMATION: Synthetic

<400> SEQUENCE: 409
tgtaaaacga cggccagtgc acccagcagt ttggccc                        37

<210> SEQ ID NO 410
<211> LENGTH: 40
<212> TYPE: DNA
<213> ORGANISM: Artificial Sequence
<220> FEATURE:
<223> OTHER INFORMATION: Synthetic

<400> SEQUENCE: 410
caggaaacag ctatgaccgt ggagaagctc ccaaccaagc                     40

<210> SEQ ID NO 411
<211> LENGTH: 37
<212> TYPE: DNA
<213> ORGANISM: Artificial Sequence
```

```
<220> FEATURE:
<223> OTHER INFORMATION: Synthetic

<400> SEQUENCE: 411
tgtaaaacga cggccagttg ccgaacgcac cggagca                    37

<210> SEQ ID NO 412
<211> LENGTH: 47
<212> TYPE: DNA
<213> ORGANISM: Artificial Sequence
<220> FEATURE:
<223> OTHER INFORMATION: Synthetic

<400> SEQUENCE: 412
tgtaaaacga cggccagtga aagttaaaat tcccgtcgct atcaaga         47

<210> SEQ ID NO 413
<211> LENGTH: 39
<212> TYPE: DNA
<213> ORGANISM: Artificial Sequence
<220> FEATURE:
<223> OTHER INFORMATION: Synthetic

<400> SEQUENCE: 413
caggaaacag ctatgaccgg cctgaggttc agagccatg                  39

<210> SEQ ID NO 414
<211> LENGTH: 36
<212> TYPE: DNA
<213> ORGANISM: Artificial Sequence
<220> FEATURE:
<223> OTHER INFORMATION: Synthetic

<400> SEQUENCE: 414
tgtaaaacga cggccagtca ccgtgcagct catcat                     36

<210> SEQ ID NO 415
<211> LENGTH: 40
<212> TYPE: DNA
<213> ORGANISM: Artificial Sequence
<220> FEATURE:
<223> OTHER INFORMATION: Synthetic

<400> SEQUENCE: 415
caggaaacag ctatgaccgt tgagcaggta ctgggagcca                 40

<210> SEQ ID NO 416
<211> LENGTH: 40
<212> TYPE: DNA
<213> ORGANISM: Artificial Sequence
<220> FEATURE:
<223> OTHER INFORMATION: Synthetic

<400> SEQUENCE: 416
caggaaacag ctatgaccca gccaggaacg tactggtgaa                 40

<210> SEQ ID NO 417
<211> LENGTH: 39
<212> TYPE: DNA
<213> ORGANISM: Artificial Sequence
<220> FEATURE:
<223> OTHER INFORMATION: Synthetic

<400> SEQUENCE: 417
tgtaaaacga cggccagtct ttctcttccg cacccagct                  39
```

```
<210> SEQ ID NO 418
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Dideoxynucleotide

<400> SEQUENCE: 418
ctccaccgtg cagctcatca t                                              21

<210> SEQ ID NO 419
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Dideoxynucleotide

<400> SEQUENCE: 419
ctccaccgtg cagctcatga t                                              21

<210> SEQ ID NO 420
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Dideoxynucleotide

<400> SEQUENCE: 420
ctccaccgtg cagctgatca t                                              21

<210> SEQ ID NO 421
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Dideoxynucleotide

<400> SEQUENCE: 421
ctccaccgtg cacctcatca t                                              21

<210> SEQ ID NO 422
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Dideoxynucleotide

<400> SEQUENCE: 422
ctccaccgtc cagctcatca t                                              21
```

```
<210> SEQ ID NO 423
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Dideoxynucleotide

<400> SEQUENCE: 423
ctccacggtg cagctcatca t                                          21

<210> SEQ ID NO 424
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: Dideoxynucleotide

<400> SEQUENCE: 424
gttgagcagg tactgggagc ca                                         22

<210> SEQ ID NO 425
<211> LENGTH: 60
<212> TYPE: DNA
<213> ORGANISM: Homo sapiens

<400> SEQUENCE: 425
gaggtggcac gtcgagtagt gcgtcgagta cgggaagccg acggaggacc tgatacaggc    60

<210> SEQ ID NO 426
<211> LENGTH: 60
<212> TYPE: DNA
<213> ORGANISM: Homo sapiens

<400> SEQUENCE: 426
gaggtggcac gtcgagtagt acgtcgagta cgggaagccg acggaggacc tgatacaggc    60

<210> SEQ ID NO 427
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Dideoxynucleotide

<400> SEQUENCE: 427
ctccaccgtg cagctcatca t                                          21

<210> SEQ ID NO 428
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
```

```
<223> OTHER INFORMATION: Dideoxynucleotide

<400> SEQUENCE: 428
ctccaccgtg cagctcatga t                                              21

<210> SEQ ID NO 429
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Dideoxynucleotide

<400> SEQUENCE: 429
ctccaccgtg cagctgatca t                                              21

<210> SEQ ID NO 430
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Dideoxynucleotide

<400> SEQUENCE: 430
ctccaccgtg cacctcatca t                                              21

<210> SEQ ID NO 431
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Dideoxynucleotide

<400> SEQUENCE: 431
ctccaccgtc cagctcatca t                                              21

<210> SEQ ID NO 432
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: Dideoxynucleotide

<400> SEQUENCE: 432
ctccacggtg cagctcatca t                                              21

<210> SEQ ID NO 433
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (22)..(22)
<223> OTHER INFORMATION: Dideoxynucleotide

<400> SEQUENCE: 433
gttgagcagg tactgggagc ca                                              22

<210> SEQ ID NO 434
<211> LENGTH: 60
<212> TYPE: DNA
<213> ORGANISM: Homo sapiens

<400> SEQUENCE: 434
gaggtggcac gtcgagtagt gcgtcgagta cgggaagccg acggaggacc tgatacaggc     60

<210> SEQ ID NO 435
<211> LENGTH: 60
<212> TYPE: DNA
<213> ORGANISM: Homo sapiens

<400> SEQUENCE: 435
gaggtggcac gtcgagtagt acgtcgagta cgggaagccg acggaggacc tgatacaggc     60

<210> SEQ ID NO 436
<211> LENGTH: 33
<212> TYPE: DNA
<213> ORGANISM: Artificial Sequence
<220> FEATURE:
<223> OTHER INFORMATION: Synthesis

<400> SEQUENCE: 436
acactctttc cctacacgac gctcttccga tct                                  33

<210> SEQ ID NO 437
<211> LENGTH: 34
<212> TYPE: DNA
<213> ORGANISM: Artificial Sequence
<220> FEATURE:
<223> OTHER INFORMATION: Synthesis

<400> SEQUENCE: 437
gtgactggag ttcagacgtg tgctcttccg atct                                 34
```

METHOD OF AMPLIFYING A TARGET NUCLEIC ACID

BACKGROUND OF THE INVENTION

Human genetic mutations whether it is de novo or somatic are critical information to understand human genetic disease (Ku, C. S. et al, A new era in the discovery of de novo mutations underlying human genetic disease, Hum Genomics 6, 27, 2012), cancer biology (Helleday, T. et al, Mechanisms underlying mutational signatures in human cancers, Nat Rev Genet 15, 585-598, 2014) and potential anticancer therapies. de novo mutation has long been known to cause genetic disease and it also plays an important role in rare and common forms of neurodevelopmental diseases, including intellectual disability, autism and schizophrenia (Veltman, J. A. et al, De novo mutations in human genetic disease, Nat Rev Genet 13, 565-575, 2012). Somatic mutation in cancer genome has been extensively studied and believed to hold the key to understand cancer origin, risk and potential biomarker discovery for therapeutic use. Detection of those genetic mutations is critical for diagnosis of disease and patient treatment.

Studies of de novo or somatic mutations in the human genome have been very challenging in the past because of genomic sequencing technology limitations. However, the development of high-throughput next-generation sequencing (NGS) technologies has greatly facilitated the study of such mutations. Whole-genome sequencing (WGS) and whole-exome sequencing (WES) can now be performed on parent offspring trios to identify de novo point mutations in the entire genome or within protein-coding regions, respectively.

WGS and WES are great tools for genetic mutation study, but they are still cost prohibitive for routine clinical use. In some cases, if only a set of genetic mutations are known to be related with certain disease or particular drug response, it would be efficient and cost effective to do genetic analysis for those genes. In order to do a limited resequencing of panel of genes, those genes need to be captured before carrying out NGS. The capture process could be achieved using either hybridization or amplicon approach. For hybridization capture approach, gDNA was first physically fragmented or enzymatically digested, then synthetic oligonucleotides are hybridized to regions of interest in solution to capture the intended sequences. For amplicon based approach, the intended regions are directly captured by amplification of PCR primers. Hybridization capture approach is scalable to large number of genes, but hybridization step usually takes overnight and the total process takes multiple days. It also requires at least 1 to 2 µg of gDNA material input. Amplicon based approach takes less time and only require 10 to 50 ng gDNA input, so it is suitable if quantities of DNA input from clinical samples are limited. However, multiplex PCR primers also generate nonspecific amplification products especially when the number of PCR primers increase. In fact, majority of PCR products are nonspecific amplicons when the number of primers approaches hundreds. Therefore, amplicon based approach usually uses an enzyme digestion step to reduce nonspecific amplification product followed by additional ligation step or use a multiple steps of cleaning up to reduce those nonspecific products. Those nonspecific amplification products not only require multiple steps during sequencing library generation but also can introduce sequencing data errors.

Recently detection of low frequency mutation has been a rapidly growing area of interest because of its important applications in basic and clinical research. One kind of rare mutations, circulating cell-free DNA (cfDNA) from human plasma are used for prenatal screening (Chiu, R. W. et al, Noninvasive prenatal diagnosis empowered by high-throughput sequencing, Prenat Diagn 32, 401-406, 2012), while circulating tumor DNA (ctDNA) has been confirmed to contain the hallmark mutations of cancerous cells. ctDNA has the potential to be a novel, non-invasive biomarker that promotes early cancer detection at a surgically curable stage, reduces the necessity of repeat tissue biopsies, and detects the early relapse of the disease, thereby increasing the efficacy of targeted therapy. For cancers that are often detected at a late stage, including lung, pancreatic, and ovarian etc., a high-sensitivity ctDNA assay could be used as an important screening test to detect typically terminal metastatic stage cancer at an earlier, potentially curable stage. With continuous ctDNA monitoring from patient blood, change of ctDNA composition and quantitation could be used to monitor cancer progression in real time, improving patient safety and eliminating the cost related to repeat tissue biopsies.

Unfortunately, detection of ctDNA remains challenging by its presence in relatively low quantities especially in early-stage cancer patients. There are several available techniques developed so far to detect ctDNA including BEAMing, digital PCR, and next generation sequencing. All those methods can detect low frequency mutations by assessing individual molecules one-by-one. NGS has the advantage over traditional methods in that large amount of sequencing information can be obtained easily in an automated fashion. However, NGS cannot generally be used to detect rare mutations because of its high error rate associated with NGS library generation and the sequencing process. Some of these errors presumably result from mutations introduced during template preparation, during the pre-amplification steps required for library preparation and during further solid-phase amplification on the instrument itself. Other errors are due to base mis-incorporation during sequencing and base-calling errors.

Therefore, there remains a continuing need for a novel approach to eliminate nonspecific amplification products during multiplex PCR reaction so that the sequencing library could be directly generated without additional digestion and ligation steps, and a novel approach to reduce error rate so that rare mutation could be reliably detected using current NGS instrument.

BRIEF SUMMARY OF THE INVENTION

One aspect of the present disclosure provides a method of amplifying a target nucleic acid, wherein the method comprises: (a) providing a reaction mixture comprising: (i) a nucleic acid sample comprising or suspected of comprising the target nucleic acid, (ii) at least 20 different types of primer pairs, wherein at least one primer of each type of primer pairs is complementary to a portion of the target nucleic acid, and each primer pair has at least one blocking primer comprising a blocking group capable of blocking polymerase extension, (iii) nucleic acid polymerase, and (iv) de-blocking agent capable of enabling polymerization of the target nucleic acid by said nucleic acid polymerase using the blocking primers; and (b) incubating the reaction mixture under a condition for amplification of the target nucleic acid.

In some embodiments, the blocking group is at or near 3' terminal of each blocking primer. In some embodiments, the blocking group is 2', 3'-dideoxynucleotide, ribonucleotide residue, 2', 3'SH nucleotide, or 2'-O—PO₃ nucleotide.

In some embodiments, the blocking primer is complementary to a portion of the target nucleic acid. In some embodiments, the blocking primer is further modified to decrease the amplification of undesired nucleic acid. In some embodiments, the modification is introduction of at least one mismatched nucleotide in the primer. In some embodiments, the mismatched nucleotide is 2-18 bp away from the nucleotide with the blocking group. In some embodiments, wherein the mismatched nucleotide is 3, 4, 5, 6, 7, 8, 9, 10, 11, 12, 13, 14, 15, 16 or 17 bp away from the nucleotide with the blocking group. In some embodiments, the mismatched nucleotide base is located on the 5' side of the nucleotide with the blocking group. In some embodiments, the modification is a modification to decrease the Tm between the blocking primer and the undesired nucleic acid. In some embodiments, the modification is a modification to increase the Tm between the blocking primer and the target nucleic acid. In some embodiments, wherein the modification is a modification to form an extra bridge connecting the 2' oxygen and 4' carbon of at least one nucleotide of the blocking primer.

In some embodiments, there are no more than 20 complementary nucleotide pairings and no more than 50% sequence complementarity between any two primers. In some embodiments, there are no more than 19, 18, 17, 16, 15, 14, 13, 12, 11, 10, 9, 8, 7, 6 or 5 complementary nucleotide pairings between any two primers.

In some embodiments, the reaction mixture comprises at least 30, 40, 50, 60, 70, 80, 90, 100, 120, 140, 160, 180, 200, 250, 300, 400, 500, 600, 700, 800, 900 or 1000 different types of primer pairs.

In some embodiments, each of the primers is 8 to 100 nucleotides in length.

In some embodiments, the different types of primer pairs can complementarily bind to different target nucleic acids or different sequences in the same target nucleic acid.

In some embodiments, wherein the de-blocking agent is CS5 DNA polymerase with the mutations selected from G46E, L329A, Q601R, D640G, I669F, S671F, E678G or the combination of such mutations, ampliTaq or KlenTaq polymerase with F667Y mutation, pyrophosphate or RNase H2.

In some embodiments, the target nucleic acid is single stranded or double stranded DNA.

In some embodiments, the target nucleic acid is double stranded DNA ligated with single or double adaptor tags or single stranded DNA ligated with single adaptor tag.

In some embodiments, the reaction mixture further comprises at least one primer complementary in whole or in part with the adaptor tag.

In some embodiments, the target nucleic acid is double stranded DNA comprising single or double molecular index tag or single stranded DNA comprising single molecular index tag. In some embodiments, the molecular index tag comprises unique identifier nucleic acid sequence and an adaptor tag.

In some embodiments, the primers have common tailing sequence at or near 5' terminal of the primers. In some embodiments, the common tailing sequence can be used as molecular index tag, sample index tag or adaptor tag or combinations of all three tags.

In some embodiments, the reaction mixture further comprises high fidelity polymerase. In some embodiments, the high fidelity polymerase is PFU DNA Polymerase.

In some embodiments, the step (b) "incubating the reaction mixture under a condition for amplification of the target nucleic acid" comprises the steps of denaturing the target nucleic acid; annealing the primers with the target nucleic acid to allow the formation of a nucleic acid-primer hybrid; and incubating the nucleic acid-primer hybrid to allow the nucleic acid polymerase to amplify the target nucleic acid.

In some embodiments, the formation of a nucleic acid-primer hybrid results in de-blocking the block group in the primer through de-blocking agent.

In some embodiments, the steps of "denaturing the target nucleic acid; annealing the primers with the target nucleic acid to allow the formation of a nucleic acid-primer hybrid; and incubating the nucleic acid-primer hybrid to allow the nucleic acid polymerase to amplify the target nucleic acid" is repeated at least 1 time, 5 times, 10 times, 15 times, 20 times, 25 times, 30 times, 35 times, 40 times or 50 times. In some embodiments, the step (b) is repeated from about 20 times to about 50 times.

In some embodiments, the nucleic acid sample comprises the target nucleic acid. In some embodiments, the target nucleic acids in the nucleic acid sample is no more than 1 copy, 2 copies, 5 copies, 8 copies, 10 copies, 20 copies, 30 copies, 50 copies, 80 copies or 100 copies. In some embodiments, the molar percentage of target nucleic acid in the nucleic acid sample is less than 50%, 20%, 10%, 5%, 3%, 1%, 0.5%, 0.1%, 0.05%, 0.01%, 0.005%, or 0.001%.

In some embodiments, the nucleic acid other than the target nucleic acid is not amplified in step (b) substantially. In some embodiments, the molar percentage of undesired nucleic acid in the reaction products obtained from step (b) is less than 20%, 15%, 10%, 5%, 3%, 2% or 1%.

In some embodiments, the method is used for selective enrichment of mutant nucleic acid in a sample comprising wildtype nucleic acid. In some embodiments, wherein at least one blocking primer is complementary to the mutant nucleic acid at the mutant residues and the nucleotide of the blocking primer corresponding to a mutant residue has the blocking group.

Another aspect of the present disclosure provides a method of sequencing a target nucleic acid, wherein the method comprises: (a) providing a reaction mixture comprising: (i) a nucleic acid sample comprising or suspected of comprising the target nucleic acid, (ii) at least 20 different types of primer pairs, wherein at least one primer of each type of primer pairs is complementary to a portion of the target nucleic acid, and each primer pair has at least one blocking primer comprising a blocking group capable of blocking polymerase extension, (iii) nucleic acid polymerase, and (iv) de-blocking agent capable of enabling polymerization of the target nucleic acid by said nucleic acid polymerase using the blocking primers; (b) incubating the reaction mixture under a condition for amplification of the target nucleic acid; and (c) determining the sequence of the reaction products obtained from step (b).

In some embodiments, the method is used for sequencing by capillary electrophoresis, PCR or high throughput sequencing. In some embodiments, the blocking primer is further modified to decrease the amplification of undesired nucleic acid.

In some embodiments, the reaction mixture further comprises high fidelity polymerase.

Yet another aspect of the present disclosure provides a method of sequencing a target nucleic acid, wherein the method comprises: (a) providing a reaction mixture comprising: (i) a nucleic acid sample comprising or suspected of comprising the target nucleic acid, (ii) at least 20 different types of primer pairs, wherein at least one primer of each type of primer pairs is complementary to a portion of the target nucleic acid, and each primer pair has at least one blocking primer comprising a blocking group capable of blocking polymerase extension, (iii) nucleic acid polymerase, and (iv) de-blocking agent capable of enabling polymerization of the target nucleic acid by said nucleic acid polymerase using the blocking primers; (b) incubating the reaction mixture under a condition for amplification of the target nucleic acid; (c) adding adaptor tag, molecular index tag and/or sample index tag to the reaction products obtained from step (b); and (d) determining the sequence of the reaction products obtained from step (c).

In some embodiments, the method is used for sequencing by capillary electrophoresis, PCR or high throughput sequencing.

In some embodiments, wherein the blocking primer is modified to decrease the amplification of undesired nucleic acid.

In some embodiments, wherein the reaction mixture further comprises high fidelity polymerase.

Yet another aspect of the present disclosure provides a kit for amplifying a target nucleic acid, wherein the kit comprises: (i) at least 20 different types of primer pairs, wherein at least one primer of each type of primer pairs is complementary to a portion of the target nucleic acid, and each primer pair has at least one blocking primer comprising a blocking group capable of blocking polymerase extension, (ii) nucleic acid polymerase, and (iii) de-blocking agent capable of enabling polymerization of the target nucleic acid by said nucleic acid polymerase using the blocking primer.

In some embodiments, the blocking primer is modified to decrease the amplification of undesired nucleic acid.

In some embodiments, the reaction mixture further comprises high fidelity polymerase.

Yet another aspect of the present disclosure provides a method of amplifying a target nucleic acid, wherein the method comprises: (a) providing a reaction mixture comprising: (i) a nucleic acid sample comprising or suspected of comprising the target nucleic acid, (ii) at least one type of primers that is complementary to a portion of the target nucleic acid, and each type of primers has at least one blocking primer comprising a blocking group capable of blocking polymerase extension, wherein the blocking primer is modified to decrease the amplification of undesired nucleic acid, (iii) nucleic acid polymerase, and (iv) de-blocking agent capable of enabling polymerization of the target nucleic acid by said nucleic acid polymerase using the blocking primer; and (b) incubating the reaction mixture under a condition for amplification of the target nucleic acid.

In some embodiments, the modification is introduction of at least one mismatched nucleotide in the primer.

In some embodiments, the mismatched nucleotide is 2-18 bp away from the nucleotide with the blocking group.

In some embodiments, the mismatched nucleotide is 3, 4, 5, 6, 7, 8, 9, 10, 11, 12, 13, 14, 15, 16 or 17 bp away from the nucleotide with blocking group.

In some embodiments, the mismatched nucleotide is located on the 5' side of the blocking group.

In some embodiments, the modification is a modification to decrease the affinity between the blocking primer and the target nucleic acid.

In some embodiments, the modification is a modification to form an extra bridge connecting the 2' oxygen and 4' carbon of at least one nucleotide of the blocking primer.

In some embodiments, the method is used for selective enrichment of mutant nucleic acid in a sample comprising wild type nucleic acid.

In some embodiments, a blocking primer is complementary to a portion of the target nucleic acid. In some embodiments, the blocking primer is complementary to the mutant nucleic acid at the mutant residue and the nucleotide of the blocking primer corresponding to a mutant residue has the blocking group.

Yet another aspect of the present disclosure provides a kit for amplifying a target nucleic acid, wherein the kit comprises: (i) at least one type of primers that is complementary to a portion of the target nucleic acid, and each type of primers have at least one blocking primer comprising a blocking group capable of blocking polymerase extension, wherein the blocking primer is modified to decrease the amplification of undesired nucleic acid, (ii) nucleic acid polymerase, and (iii) de-blocking agent capable of enabling polymerization of the target nucleic acid by said nucleic acid polymerase using the blocking primer.

In some embodiments, the blocking primer is modified to decrease the affinity between the blocking primer and the target nucleic acid.

DETAILED DESCRIPTION OF THE INVENTION

Figure 1:
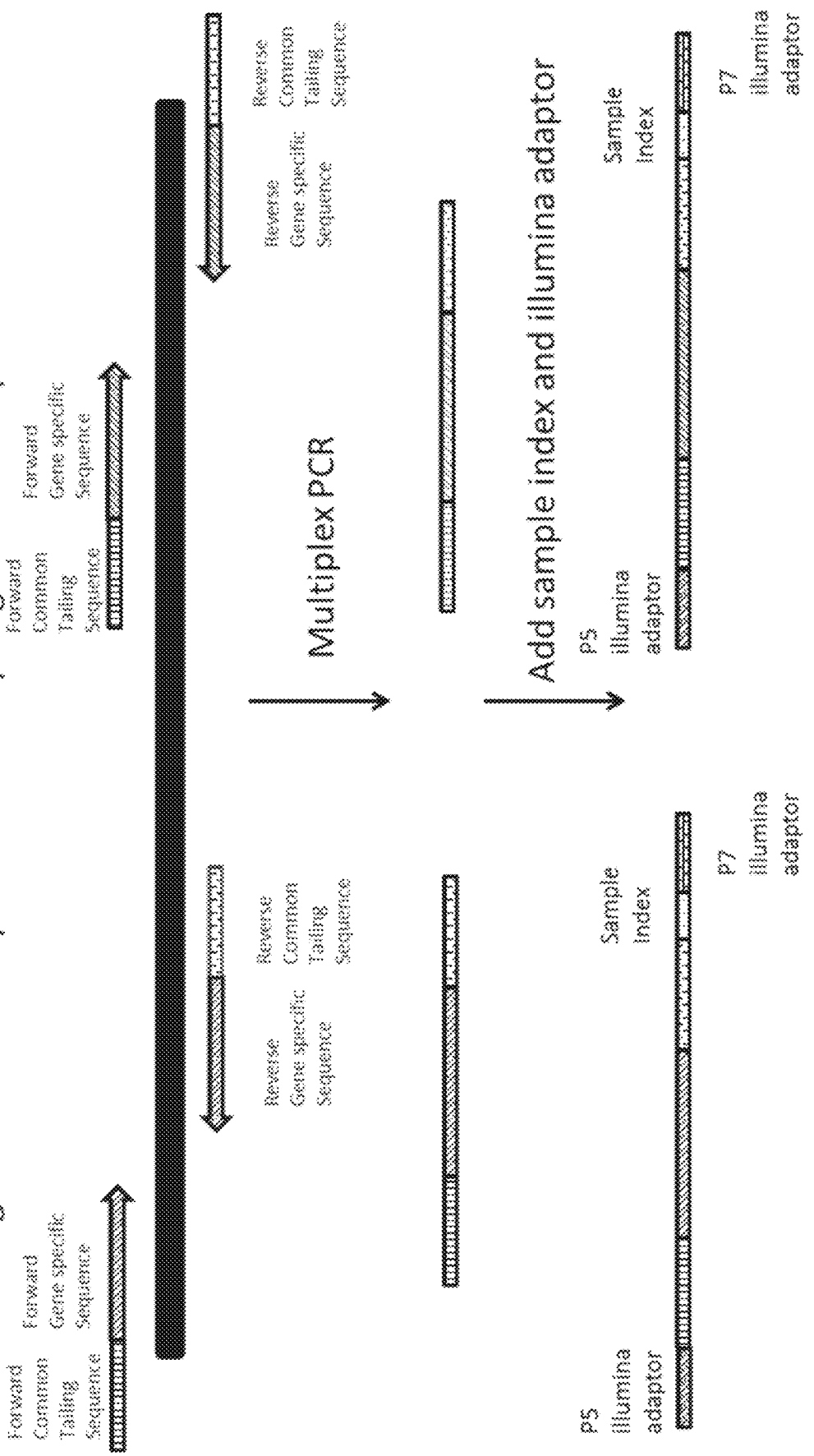
FIG. 1: NGS library construction for genomic DNA by multiplex PCR.
Figure 2:
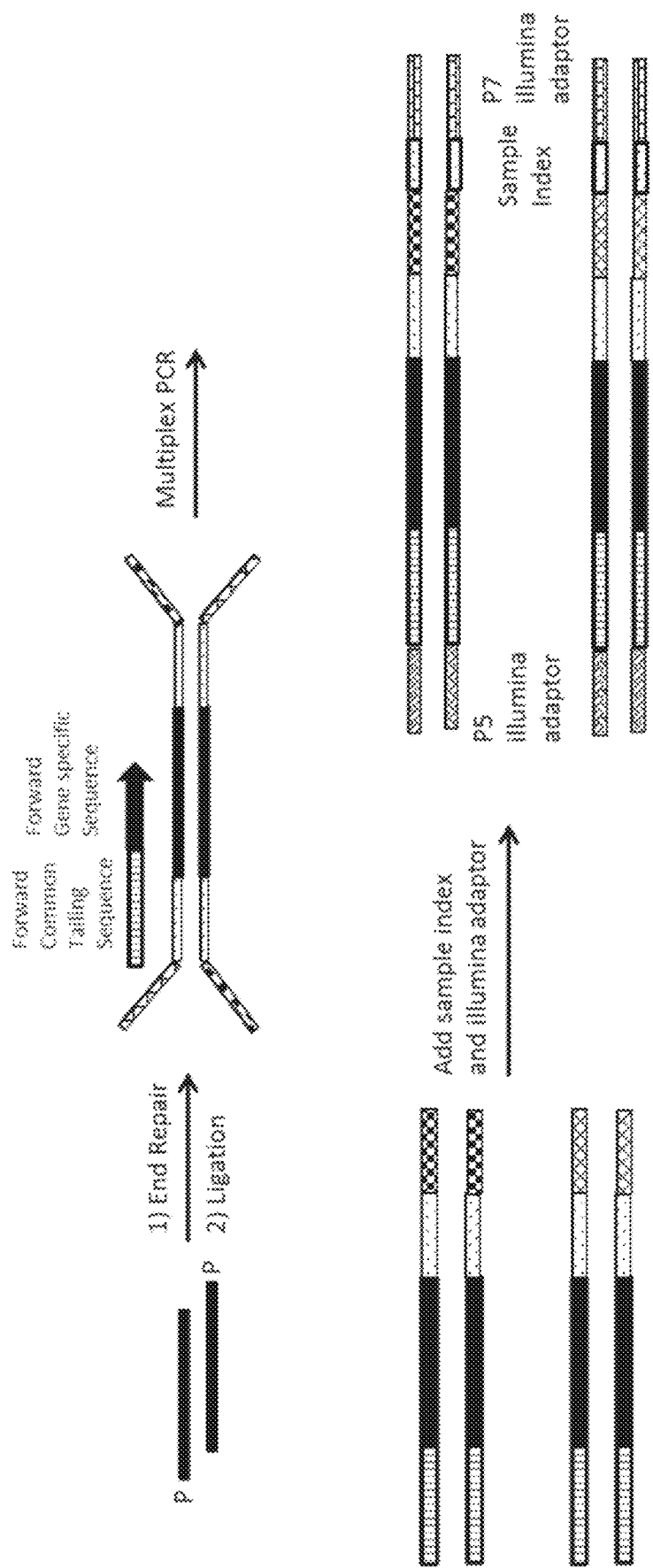
FIG. 2: NGS library construction for fragmented DNA by multiplex PCR.
Figure 3:
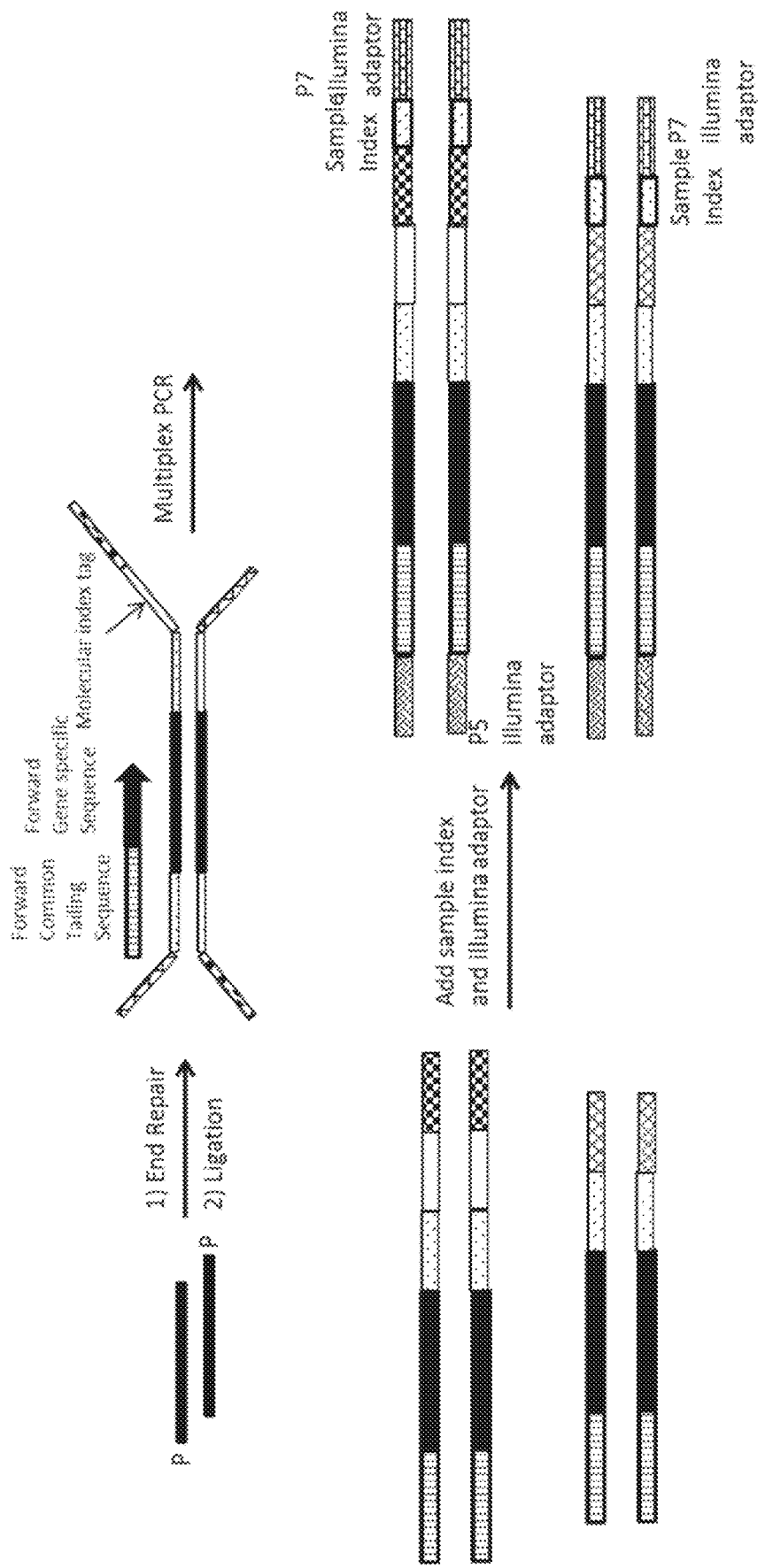
FIG. 3: NGS library construction for fragmented DNA with single stranded molecular index tag by multiplex PCR.
Figure 4:
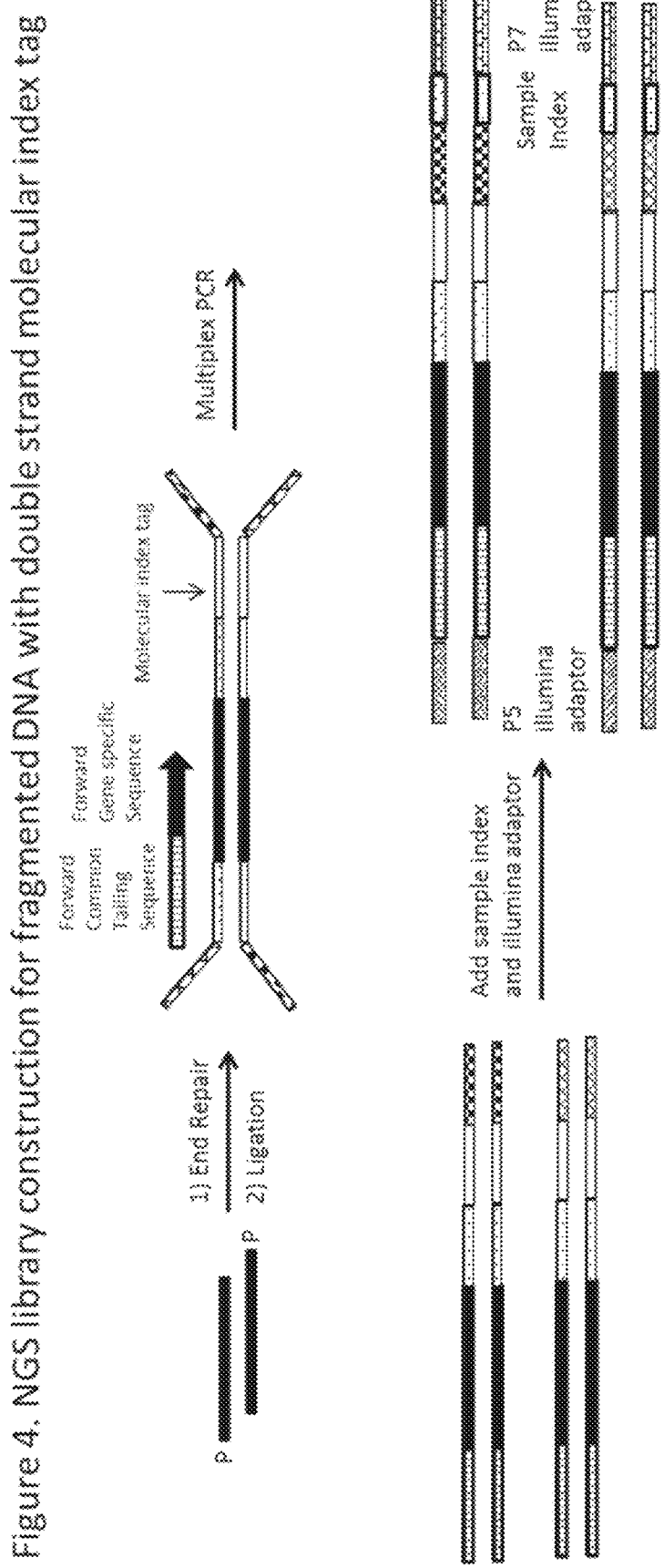
FIG. 4: NGS library construction for fragmented DNA with double stranded molecular index tags by multiplex PCR.

One aspect of the present disclosure provides a method of amplifying a target nucleic acid, wherein the method comprises: (a) providing a reaction mixture; and (b) incubating the reaction mixture under a condition for amplification of the target nucleic acid.

Providing a Reaction Mixture

In some embodiments, a reaction mixture for detecting a target nucleic acid of the present disclosure comprises: (i) a nucleic acid sample comprising or suspected of comprising the target nucleic acid, (ii) at least 20 different types of primer pairs, wherein at least one primer of each type of primer pairs is complementary to a portion of the target nucleic acid, and each primer pair has at least one blocking primer comprising a blocking group capable of blocking polymerase extension, (iii) nucleic acid polymerase, and (iv) de-blocking agent capable of enabling polymerization of the target nucleic acid by said nucleic acid polymerase using the blocking primers.

Nucleic Acid Sample

The term "nucleic acid" as used in the present disclosure refers to a biological polymer of nucleotide bases, and may include but is not limited to deoxyribonucleic acid (DNA), ribonucleic acid (RNA), micro RNA (miRNA), and peptide nucleic acid (PNA), modified oligonucleotides (e.g., oligonucleotides comprising nucleotides that are not conventional to biological RNA or DNA, such as 2'-O-methylated oligonucleotides), and the like. The nucleotides of the present disclosure can be natural or unnatural, substituted or unsubstituted, modified or unmodified. The nucleotides can be linked by phosphodiester bonds, or by phosphorothioate linkages, methylphosphonate linkages, boranophosphate linkages, or the like. The polynucleotides can additionally comprise non-nucleotide elements such as labels, quenchers, blocking groups, or the like. The nucleic acid can be, e.g., single-stranded or double-stranded.

The term "DNA" as used in the present disclosure refers to deoxyribonucleic acid, a long chain polymer biological macromolecule which forms genetic instructions. The subunit of DNA is nucleotide. Each nucleotide in DNA consists of a nitrogenous base, a five-carbon sugar (2-deoxyribose) and phosphate groups. Neighboring nucleotides are linked via diester bonds formed by deoxyribose and phosphoric acid, thereby forming a long chain framework. Generally, there are four types of nitrogenous bases in DNA nucleotides, namely adenine (A), guanine (G), and cytosine (C), thymine (T). The bases on the two DNA long chains pair via hydrogen bonds, wherein adenine (A) pairs with thymine (T), and guanine (G) pairs with cytosine (C).

The term "nucleic acid sample" as used in the present disclosure refers to any sample containing nucleic acid, including but not limited to cells, tissues, and body fluids, etc. In some embodiments, the nucleic acid sample is a tissue, e.g., biopsy tissue or paraffin embedded tissue. In some embodiments, the nucleic acid sample is bacteria or animal or plant cells. In some other embodiments, the nucleic acid sample is a body fluid, e.g., blood, plasma, serum, saliva, amniocentesis fluid, pleural effusion, seroperitoneum, etc. In some embodiments, the nucleic acid sample is blood, serum or plasma.

In some embodiments, the nucleic acid sample comprises or is suspected of comprising the target nucleic acid.

The term "target nucleic acid" or "target region" as used in the present disclosure refers to any region or sequence of a nucleic acid which is to be amplified intentionally.

In some specific embodiments, the target nucleic acid is DNA, RNA or a hybrid or a mixture thereof. In some specific embodiments, the target nucleic acid is genomic DNA. In some specific embodiments, the target nucleic acid is cell-free DNA (cfDNA). In some specific embodiments, the target nucleic acid is circulating tumor DNA (ctDNA).

"Cell-free DNA" as used in the present disclosure refers to DNA released from cells and found in circulatory system (e.g., blood), the source of which is generally believed to be genomic DNA released during apoptosis.

"Circulating tumor DNA" as used in the present disclosure refers to the cell-free DNA originated from tumor cells. In human body, a tumor cell may release its genomic DNA into the blood due to causes such as apoptosis and immune responses. Since a normal cell may also release its genomic DNA into the blood, circulating tumor DNA usually constitutes only a very small part of cell-free DNA.

In some embodiments, the target nucleic acid is single stranded or double stranded DNA. In some embodiments, the target nucleic acid is the whole or a portion of one or more genes selected from ABL1, AKT1, ALK, APC, ATM, BRAF, CDH1, CDKN2A, CSF1R, CTNNB1, EGFR, ERBB2, ERBB4, EZH2, FBXW7, FGFR1, FGFR2, FGFR3, FLT3, GNA11, GNAQ, GNAS, HNF1A, HRAS, IDH1, IDH2, JAK2, JAK3, KDR, KIT, KRAS, MET, MLH1, MPL, NOTCH1, NPM1, NRAS, PDGFRA, PIK3CA, PTEN, PTPN11, RB1, RET, SMAD4, SMARCB1, SMO, SRC, STK11, TP53 and VHL.

In some embodiments, the amount of target nucleic acid in the nucleic acid sample is no more than 1 copy, 2 copies, 3 copy, 4 copies, 5 copies, 6 copies, 7 copies, 8 copies, 9 copies, 10 copies, 12 copies, 15 copies, 18 copies, 20 copies, 30 copies, 50 copies, 80 copies or 100 copies. In some embodiments, the molar percentage (molar/molar) of target nucleic acid in the nucleic acid sample is less than 50%, 20%, 10%, 8%, 6%, 5%, 3%, 1%, 0.5%, 0.1%, 0.05%, 0.01%, 0.005%, or 0.001%. In some embodiments, the ratio of molar of target nucleic acid and the molar of un-target nucleic acid in the nucleic acid sample is less than 50%, 20%, 10%, 8%, 6%, 5%, 3%, 1%, 0.5%, 0.1%, 0.05%, 0.01%, 0.005%, or 0.001%.

In some embodiments, the target nucleic acid is DNA fragment. In some embodiments, the size of the target nucleic acid is 0.01-5 kb, 0.1-5 kb, 0.1-1 kb, 1-2 kb, 2-3 kb, 3-4 kb, 4-5 kb, 0.2-0.4 kb, 0.5-1 kb, 0.1-0.5 kb, 0.01-0.5 kb, 0.01-0.4 kb, 0.01-0.3 kb, 0.01-0.25 kb, 0.02-0.25 kb, 0.05-0.3 kb or 0.05-0.25 kb. The DNA fragment can be obtained through common technology in the art (e.g., physical breaking, cleavage using specific restriction endonuclease, etc.).

In some embodiments, the target nucleic acid is double stranded DNA ligated with single or double adaptor tags or single stranded DNA ligated with single adaptor tag.

The term "adaptor tag" as used in the present disclosure refers to a specific DNA sequence attached to one or two ends of a nucleic acid (single stranded or double stranded) according to needs, and the length of the adaptor is usually within 5-50 bp. The adaptor tag can be used to facilitate amplifying the target nucleic acid and/or sequencing the amplified target nucleic acid. In some embodiments, the adaptor tag is used to facilitate the ligation of tags for sequencing (e.g., the ligation of P5 and P7 tag for Illumina MiSeq sequencer). In some embodiments, the adaptor tag is attached to only one end of a single stranded nucleic acid at 3' terminal or 5' terminal. In some embodiments, the adaptor tag is attached to two ends of a single stranded nucleic acid. In some embodiments, one adaptor tag is attached to each strand in double stranded nucleic acid at 3' terminal or 5' terminal. For example, one adaptor tag is attached to one strand in double stranded nucleic acid at its 3' terminal and one adaptor tag is attached to the other strand in double stranded nucleic acid at its 5' terminal, and the two adaptor tags are identical or complementary to each other. In some embodiments, two adaptor tags are attached to two ends of each strand in double stranded nucleic acid.

The adaptor tag can be attached to the nucleic acid through common technologies in the art. In some embodiments, where the target nucleic acid is double stranded DNA, the adaptor tag can be attached to the nucleic acid through the following steps: (a) providing an adaptor ligation nucleic acid designed to contain sequences to ligate with an end of one strand of the DNA (for example, the adaptor ligation nucleic acid contains a hybridization complementary region, or a random hybridization short sequence, e.g., poly-T); (b) hybridization of the adaptor ligation nucleic acid and the strand of the DNA; and (c) adding polymerase (e.g., reverse transcriptase) after the hybridization to extend the adaptor ligation nucleic acid, thereby the adaptor tag is ligated to the end of the target DNA fragment. For attaching another adaptor to the other end of the same strand or to the other strand of the DNA, an adaptor ligation nucleic acid can be designed according to the needs and steps (b)-(c) can be repeated. In some other embodiments, where the DNA fragment is double stranded and the end of the DNA fragment is a sticky end, the adaptor tag can be attached to the nucleic acid through the following steps: (a) designing the adaptor ligation nucleic acid to contain sequences to ligate with the sticky end; (b) complementarily annealing the adaptor ligation nucleic acid with the sticky end; and (c) ligating the adaptor ligation nucleic acid to the double stranded of the target DNA using a ligase, thereby achieving the purpose of attaching the adapter to the end of the DNA fragment.

In some embodiments, the target nucleic acid is double stranded DNA comprising single or double molecular index tags or single stranded DNA comprising single molecular index tag. In some embodiments, the molecular index tag comprises unique identifier nucleic acid sequence and an adaptor tag. In some embodiments, the adaptor tag is at one end of the target nucleic acid.

The term "molecular index tag" as used in the present disclosure refers to a nucleic acid sequence used as a tag, which can be ligated to or existing at the 5' end, the 3' end or both ends of a DNA fragment. In DNA sequencing, especially in high throughout sequencing technology, a molecular index tag therein is used to mark particular DNA molecule. After amplification and sequencing, the count of the molecular index sequence therein is used to mark particular DNA molecule and can be the basis for determining the quantity of expression of the marked gene, or be used to trace the information of the amplified DNA molecules from the same original molecules and thereby correcting the random errors of DNA sequences during amplification and sequencing.

In some embodiments, the molecular index tag is exogenous, which is attached to the target nucleic acid through PCR (e.g., as described in MoCloskey M. L. et al, Encoding PCR products with batch-stamps and barcodes. Biochem Genet 45:761-767, 2014 or Parameswaran P, et al., A pyrosequencing-tailored nucleotide barcode design unveils opportunities for large-scale sample multiplexing. Nucleic Acids Res 35:e130, 2017) or ligation (e.g., as described in Craig D W, et al., Identification of genetic variants using bar-coded multiplexed sequencing. Nat Methods 5:887-893, 2008 or Miner B E, et al., Molecular barcodes detect redundancy and contamination in hairpin-bisulfite PCR. Nucleic Acids Res 32:e135, 2004). In some embodiments, the molecular index tag or the unique identifier nucleic acid sequence therein can be a random sequence (i.e., formed with randomly arranged A/T/C/G).

In some embodiments, the molecular index tag or the unique identifier nucleic acid sequence therein is endogenous, which are the sequences of the two ends of randomly sheared fragment.

More information for molecular index tag can be found in U.S. 20140227705 and U.S. 20150044687.

Primer

The term "primer" as used in the present disclosure refers to an oligonucleotide that is capable of acting as a point of initiation of synthesis when placed under conditions in which primer extension is initiated. Primer may comprise natural ribonucleic acid, deoxyribonucleic acid, or other forms of natural nucleic acid. Primer may also comprise un-natural nucleic acid (e.g., LNA, ZNA etc.).

Primers may be prepared using any suitable method, such as, for example, the phosphotriester and phosphodiester methods or automated embodiments thereof. In one such automated embodiment, diethylophosphoramidites are used as starting materials and may be synthesized as described by Beaucage et al., Tetrahedron Letters, 22:1859-1862 (1981). One method for synthesizing primer on a modified solid support is described in U.S. Pat. No. 4,458,006. It is also possible to use a primer which has been isolated from a biological source, such as a restriction endonuclease digest. In some embodiments, the primer with blocking nucleotide at the 3' end, can be synthesized with terminal transferase (Gibco BRL) (Nuc Aci Res 2002, 30(2)).

The term "primer pair" as used in the present disclosure refers to a pair of primers consisting of a forward primer and a reverse primer which complement with a portion of a sequence to be amplified, respectively, wherein the forward primer defines a point of initiation of the amplified sequence and the reverse primer defines a point of termination of the amplified sequence. The term "complimentary", when it is used to describe the relationship between primer and the sequence to be amplified, refers to that the primer is complimentary to the sequence to be amplified or is complimentary to a complementary sequence of the sequence to be amplified.

The pair of primers can be designed based on the sequence of the target nucleic acid. In some embodiments, at least one primer of each type of primer pairs is complementary to a portion of the target nucleic acid. In some embodiments, when the target sequence (assuming it is a double stranded DNA) has an adaptor tag, one primer of a primer pair may be complementary to a portion of the target sequence (on one strand) and the other primer may be complementary to the adaptor tag (on the other strand).

In some embodiments, each primer pair has at least one blocking primer comprising a blocking group capable of blocking polymerase extension. In some embodiments, both primers in each primer pair are blocking primers comprising a blocking group capable of blocking polymerase extension.

The term "blocking primer" as used in the present disclosure refers to a primer having a blocking group.

The term "blocking group" as used in the present disclosure refers to any chemical group covalently linked in a nucleic acid chain and capable of blocking polymerase extension. In some embodiments, the nucleotide with blocking group is a modified nucleotide at or near the 3' terminal of each blocking primer. In some embodiments, the nucleotide with blocking group is no more than 6 bp, 5 bp, 4 bp, 3 bp, 2 bp or 1 bp away from the 3' terminal of each blocking primer. In some embodiments, when the method of the present disclosure is used for selective enrichment of mutant nucleic acid in a sample comprising wildtype nucleic acid, the blocking group is at the nucleotide that is complementary with the corresponding mutated nucleotide of the mutant nucleic acid but is not complementary with the corresponding nucleotide of wildtype nucleic acid.

In some embodiments, the blocking group is 2', 3'-dideoxynucleotide, ribonucleotide residue, 2', 3'SH nucleotide, or 2'-O—PO$_3$ nucleotide. When the blocking group is a ribonucleotide residue, the blocking primer is a primer that has one ribonucleotide residue and other residues are all deoxyribonucleotide residues.

More information for blocking group and blocking primer can be found in U.S. Pat. Nos. 9,133,491, 6,534,269 and Joseph R. D. et al., RNase H-dependent PCR (rhPCR): improved specificity and single nucleotide polymorphism detection using blocked cleavable primers, BMC Biotechnology 11:80, 2011.

In some embodiments, the blocking primer is complementary to a portion of the target nucleic acid.

In some embodiments, the primers are 5 to 100 nucleotides in length. In some embodiments, the primers are at least 5, 6, 7, 8, 9, 10, 15, 20, 25, 30, 35 or 40 nucleotides in length. In some embodiments, the primers are no more than 100, 90, 80, 70, 60, 50, 40, 35, 30, 25 or 20 nucleotides in length.

In some embodiments, a primer comprises a complementary region that is complementary to the target sequence and a common tailing sequence at or near the 5' terminal of the primer. In some embodiments, the common tailing sequence can be used as molecular index tag, adaptor tag or sample index tag or combinations of all the three tags.

The term "sample index tag" as used in the present disclosure refers to a series of unique nucleotides (i.e., each sample index tag is unique), and can be used to allow for multiplexing of samples such that each sample can be identified based on its sample index tag. In some embodiments, there is a unique sample index tag for each sample in a set of samples, and the samples are pooled during sequencing. For example, if twelve samples are pooled into a single sequencing reaction, there are at least twelve unique sample index tags such that each sample is labeled uniquely.

In some embodiments, the blocking primer is modified so as to further decrease the amplification of undesired nucleic acid.

In some embodiments, the modification is introduction of at least one mismatched nucleotide in the primer. In some embodiments, the mismatched nucleotide base is located on the 5' side of the nucleotide with the blocking group.

The term "mismatched nucleotide" as used in the present disclosure refers to a nucleotide of a first nucleic acid (e.g., primer) that is not capable of pairing with a nucleotide at a corresponding position of a second nucleic acid (e.g., target nucleic acid), when the first and second nucleic acids are aligned.

The preferred or accepted location of the mismatched nucleotide can be determined through conventional technologies. For example, the mismatched nucleotides are introduced into different locations in the blocking primer, and those blocking primers are used for amplifying a target nucleic acid separately, and then the preferred or accepted location of the mismatched nucleotide for the target nucleic acid can be determined based on the results of amplification (e.g., the location decreasing the amplification of undesired nucleic acid or false positive results is preferred or accepted location). The location of the mismatched nucleotide may change along with the change of the target nucleic acid or the structure of the blocking primer. In some embodiments, the mismatched nucleotide is 2-18 bp away from the nucleotide with blocking group. In some embodiments, the mismatched nucleotide is 3, 4, 5, 6, 7, 8, 9, 10, 11, 12, 13, 14, 15, 16 or 17 bp away from the nucleotide with blocking group. In some embodiments, the mismatched nucleotide is no less than 2, 3, 4, 5, 6, 7, 8, 9 or 10 bp away from the nucleotide with blocking group. In some embodiments, the mismatched nucleotide is no more than 17, 16, 15, 14, 13, 12, 11, 10, 9, 8, 7, 6, 5, 4, 3 or 2 bp away from the nucleotide with blocking group.

In some embodiments, the modification is a modification to increase the melting temperature (Tm) between the blocking primer and the target nucleic. In some embodiments, the modification is a modification to decrease the melting temperature (Tm) between the blocking primer and the undesired nucleic acid which may be the wildtype nucleic acid in a method for selective enrichment of mutant nucleic acid in a sample. In some embodiments, wherein the modification is a modification to form an extra bridge connecting the 2' oxygen and 4' carbon of at least one nucleotide of the blocking primer, such as locked nucleic acid (LNA), see, e.g., Karkare S et al., Promising nucleic acid analogs and mimics: characteristic features and applications of PNA, LNA, and morpholino. Appl Microbiol Biotechnol 71(5): 575-586, 2006 and VesterB et al., LNA (locked nucleic acid): high-affinity targeting of complementary RNA and DNA. Biochemistry 43(42):13233-13241, 2004.

In some embodiments, the reaction mixture comprises at least 20, 25, 30, 40, 50, 60, 70, 80, 90, 100, 120, 140, 160, 180, 200, 250, 300, 400, 500, 600, 700, 800, 900 or 1000 different types of primer pairs. In some embodiments, the different types of pairs of the primers are complementary to different target nucleic acid fragments or are complementary to different sequences in the same target nucleic acid fragment.

The inventors of the present disclosure conducted a simulation experiment to evaluate the probability of forming primer pairs between primers with certain lengths generated randomly. The inventors randomly generated from 10 to 490 primer pairs in length of 20 bp to form different primer pools and, for each pool, checked primer dimer formation between any one primer and other primer in the same pool. It can be seen that the probability to form primer dimer (e.g., resulting from complementarily between different primers) is increased along with the increasing numbers of primers.

TABLE 1

Relationship between the number of the primers and the dimer length.

| Number of | Dimer Length | | | | |
|---|---|---|---|---|---|
| Primer Pairs | 4 bp | 5 bp | 6 bp | 7 bp | 8 bp |
| 10 | 100% | 90% | 20% | 0% | 0% |
| 30 | 100% | 100% | 67% | 7% | 7% |
| 50 | 100% | 100% | 88% | 22% | 0% |
| 70 | 100% | 100% | 94% | 50% | 20% |
| 90 | 100% | 100% | 96% | 48% | 9% |
| 110 | 100% | 100% | 100% | 72% | 13% |
| 130 | 100% | 100% | 99% | 61% | 23% |
| 150 | 100% | 100% | 99% | 72% | 23% |
| 170 | 100% | 100% | 100% | 79% | 29% |
| 190 | 100% | 100% | 99% | 77% | 32% |
| 210 | 100% | 100% | 100% | 82% | 31% |
| 230 | 100% | 100% | 100% | 83% | 34% |
| 250 | 100% | 100% | 100% | 87% | 34% |
| 270 | 100% | 100% | 100% | 91% | 35% |
| 290 | 100% | 100% | 100% | 90% | 39% |

TABLE 1-continued

Relationship between the number of the primers and the dimer length.

| Number of Primer Pairs | Dimer Length | | | | |
|---|---|---|---|---|---|
| | 4 bp | 5 bp | 6 bp | 7 bp | 8 bp |
| 310 | 100% | 100% | 100% | 96% | 49% |
| 330 | 100% | 100% | 100% | 96% | 47% |
| 350 | 100% | 100% | 100% | 96% | 51% |
| 370 | 100% | 100% | 100% | 95% | 48% |
| 390 | 100% | 100% | 100% | 96% | 53% |
| 410 | 100% | 100% | 100% | 97% | 52% |
| 430 | 100% | 100% | 100% | 97% | 54% |
| 450 | 100% | 100% | 100% | 97% | 54% |
| 470 | 100% | 100% | 100% | 98% | 59% |
| 490 | 100% | 100% | 100% | 98% | 63% |

For the data in Table 1, 100% means that each primer in a primer pool forms a dimer with at least one of the other primers in the same primer pool and the length of the dimer is no shorter than the indicated number; 20% means that 20% of the primers in a primer pool forms dimers in the primer pool and the length of the dimer is no shorter than the indicated number.

TABLE 2:

Relationship between the number of the primers and the dimer length in the 3' terminal of the primer

| Numbers of Primer Pairs | Dimer Length | | | | |
|---|---|---|---|---|---|
| | 4 bp | 5 bp | 6 bp | 7 bp | 8 bp |
| 10 | 50% | 10% | 0% | 0% | 0% |
| 30 | 90% | 50% | 13% | 7% | 7% |
| 50 | 98% | 56% | 26% | 2% | 0% |
| 70 | 97% | 67% | 23% | 7% | 0% |
| 90 | 100% | 80% | 33% | 12% | 6% |
| 110 | 100% | 88% | 50% | 7% | 3% |
| 130 | 100% | 82% | 40% | 10% | 4% |
| 150 | 100% | 91% | 41% | 13% | 2% |
| 170 | 100% | 95% | 49% | 15% | 4% |
| 190 | 100% | 94% | 54% | 15% | 3% |
| 210 | 100% | 94% | 50% | 14% | 3% |
| 230 | 100% | 97% | 59% | 20% | 6% |
| 250 | 100% | 99% | 58% | 21% | 7% |
| 270 | 100% | 100% | 69% | 23% | 6% |
| 290 | 100% | 99% | 65% | 19% | 5% |
| 310 | 100% | 99% | 67% | 22% | 6% |
| 330 | 100% | 99% | 70% | 24% | 4% |
| 350 | 100% | 100% | 71% | 25% | 7% |
| 370 | 100% | 100% | 73% | 26% | 6% |
| 390 | 100% | 100% | 73% | 27% | 7% |
| 410 | 100% | 100% | 75% | 31% | 10% |
| 430 | 100% | 100% | 77% | 36% | 8% |
| 450 | 100% | 100% | 79% | 34% | 7% |
| 470 | 100% | 100% | 81% | 31% | 9% |
| 490 | 100% | 100% | 82% | 36% | 9% |

For the data in Table 2, 100% means that each primer in a primer pool forms a dimer from its 3' terminal with at least one of other primers in the same primer pool and the length of the dimer is no shorter than the indicated number, 10% means that 10% of the primers in a primer pool forms dimers in the primer pool and the length of the dimer is no shorter than the indicated number.

In some embodiments, there are no more than 20 complementary nucleotide pairings between any two primers. In some embodiments, there are no more than 19, 18, 17, 16, 15, 14, 13, 12, 11, 10, 9, 8, 7, 6 or 5 complementary nucleotide pairing between any two primers. In some embodiments, there are no more than 20 consecutive complementary nucleotide pairings between any two primers. In some embodiments, there are no more than 19, 18, 17, 16, 15, 14, 13, 12, 11, 10, 9, 8, 7, 6 or 5 consecutive complementary nucleotide pairings between any two primers. In some embodiments, the above mentioned complementary nucleotides pairings are within a region from the $1^{st}$ nucleotide at the 3' terminal of a primer to the $20^{th}$, $19^{th}$, $18^{th}$, $17^{th}$, $16^{th}$, $15^{th}$, $14^{th}$, $13^{th}$, $12^{th}$, $11^{th}$, $10^{th}$, $9^{th}$ or $8^{th}$ nucleotide from the 3' terminal of the primer. In some embodiments, there are no more than 7, 6 or 5 consecutive complementary nucleotide pairings within a region from the $1^{st}$ nucleotide at the 3' terminal of a primer to the $20^{th}$, $19^{th}$, $18^{th}$, $17^{th}$, $16^{th}$, $15^{th}$, $14^{th}$, $13^{th}$, $12^{th}$, $11^{th}$, $10^{th}$, $9^{th}$ or $8^{th}$ nucleotide from the 3' terminal of the primer. In some embodiments, when calculating the number of parings between two primers, the common tailing sequence is not counted.

In some embodiments, there are no more than 20 complementary nucleotide pairings and no more than 50% sequence complementarity between any two primers. In some embodiments, there are no more than 19, 18, 17, 16, 15, 14, 13, 12, 11, 10, 9, 8, 7, 6 or 5 complementary nucleotide pairings and no more than 45%, 40%, 35%, 30%, 25% or 20% sequence complementarity between any two primers. In some embodiments, when calculating the percent complementarity between two primers, the common tailing sequence is not counted.

The term "nucleotide complementarity" or "complementarity" when in reference to nucleotide as used in the present disclosure refers to a nucleotide on a nucleic acid chain is capable of base pairing with another nucleotide on another nucleic acid chain. For example, in DNA, adenine (A) is complementary to thymine (T), and guanine (G) is complementary to cytosine (C). For another example, in RNA, adenine (A) is complementary to uracil (U), and guanine (G) is complementary to cytosine (C).

The term "percent complementarity" as used in the present disclosure refers to the percentage of nucleotide residues in a nucleic acid molecule that have complementarity with nucleotide residues of another nucleic acid molecule when the two nucleic acid molecules are annealed. Percent complementarity is calculated by dividing the number of nucleotides of the first nucleic acid that are complementary to nucleotides at corresponding positions in the second nucleic acid by the total length of the first nucleic acid.

Percent complementarity of a nucleic acid or the number of nucleotides of a nucleic acid that is complementary to another nucleic acid can also be determined routinely using BLAST programs (basic local alignment search tools) and PowerBLAST programs known in the art (Altschul et al., J. Mol. Biol., 215, 403-410, 1990; Zhang and Madden, Genome Res., 7, 649-656, 1997).

For example, primer 1 in which 18 of 20 nucleotides of the primer 1 have complementarity with 18 nucleotides of primer 2 would have 90% sequence complementarity. In this example, the complementary nucleotides may be contiguous to each other or interspersed with non-complementary nucleotides.

The term "x nucleotide pairings" as used in the present disclosure refers to the number of nucleotide residues in a nucleic acid molecule that has complementarity with the corresponding nucleotides of another nucleic acid molecule when the two nucleic acid molecules are annealed. For example, "18 nucleotide pairings" means 18 nucleotide residues of a first nucleic acid molecule has complementarity with 18 nucleotide residues of a second nucleic acid molecule. In this example, the complementary nucleotides may be contiguous to each other or interspersed with non-complementary nucleotides.

Nucleic Acid Polymerase

In some embodiments, the nucleic acid polymerase may be selected from the family of DNA polymerases like *E. coli* DNA polymerase I (such as *E. coli* DNA polymerase I, Taq DNA polymerase, Tth DNA polymerase, TfI DNA polymerase and others). This polymerase may contain the naturally occurring wild-type sequences or modified variants and fragments thereof.

In some embodiments, the nucleic acid polymerase may be selected from modified DNA polymerases of the family of DNA polymerases like *E. coli* DNA polymerase I, e.g., N-terminal deletions of the DNA polymerases, such as Klenow fragment of *E. coli* DNA polymerase I, N-terminal deletions of Taq polymerase (including the Stoffel fragment of Taq DNA polymerase, Klentaq-235, and Klentaq-278) and others.

In some embodiments, the nucleic acid polymerase includes, but is not limited to, thermostable DNA polymerases. Examples of thermostable DNA polymerases include, but are not limited to: Tth DNA polymerase, TfI DNA polymerase, Taq DNA polymerase, N-terminal deletions of Taq polymerase (e.g., Stoffel fragment of DNA polymerase, Klentaq-235, and Klentaq-278). Other DNA polymerases include KlenTaqi, Taquenase™ (Amersham), Ad-vanTaq™ (Clontech), GoTaq, GoTaq Flexi (Promega), and KlenTaq-S DNA polymerase.

In some embodiments, the nucleic acid polymerase may be commercially available DNA polymerase mixtures, including but are not limited to, TaqLA, TthLA or Expand High Fidelitypius Enzyme Blend (Roche); TthXL Klen TaqLA (Perkin-Elmer); ExTaq® (Takara Shuzo); Elongase® (Life Technologies); Advantage™ KlenTaq, Advantage™ Tth and Advantage2™ (Clontech); TaqExtender™ (Stratagene); Expand™ Long Template and Expand™ High Fidelity (Boehringer Mannheim); and TripleMaster™ Enzyme Mix (Eppendorf).

For further decreasing the amplification of undesired nucleic acid, one or more additional polymerase can be added into the reaction mixture. In some embodiments, the reaction mixture comprises high fidelity polymerase. In some embodiments, the high fidelity polymerase is PFU DNA Polymerase, Klentaq-1, Vent, or Deep Vent.

De-Blocking Agent

De-blocking agent can be selected according to the blocking group contained in the blocking primer. De-blocking agent can be any agent that may result in de-blocking the block group in the blocking primer under the condition of amplifying the target nucleic acid, when the nucleotide with the blocking group in the blocking primer is complementary to the corresponding nucleotide in the target nucleic acid. In some embodiments, the de-blocking agent is pyrophosphate, CS5 DNA polymerase with the mutations selected from G46E, L329A, Q601R, D640G, I669F, S671F, E678G or the combination thereof. In some embodiments, the de-blocking agent is ampliTaq or KlenTaq polymerase with F667Y mutation, or RNase H2.

In some embodiments, the de-blocking agent is pyrophosphate, when the blocking group is 2', 3'-dideoxynucleotide. In some embodiments, the de-blocking agent is CS5 DNA polymerase with the mutations selected from G46E, L329A, Q601R, D640G, I669F, S671F, E678G or the combination thereof (e.g., those DNA polymerases shown in U.S. 20070154914), when the blocking group is 2'-O—$PO_3$ nucleotide. In some embodiments, the blocking group is 2'-O—$PO_3$ nucleotide and the de-blocking agent is ampliTaq or KlenTaq polymerase with F667Y mutation, when the blocking group is 2'-O—$PO_3$ nucleotide. In some embodiments, the de-blocking agent is RNase H2, when the blocking group is ribonucleotide residue.

Step of Incubating the Reaction Mixture Under a Condition for Amplification of the Target Nucleic Acid Incubation of the reaction mixture of the present disclosure can be conducted in a multi-cycle process employing several alternating heating and cooling steps to amplify the DNA (see U.S. Pat. Nos. 4,683,202 and 4,683,195). In some embodiments, the incubation comprises the steps of denaturing the target nucleic acid; annealing the primers with the target nucleic acid to allow the formation of a target nucleic acid-primer hybrid; and incubating the target nucleic acid-primer hybrid to allow the nucleic acid polymerase to amplify the target nucleic acid.

An example of amplification process is briefly described below. First, a reaction mixture is heated to a temperature sufficient to denature the double stranded target DNA into its two single strands. The temperature of the reaction mixture is then decreased to allow specific single stranded primers to anneal to their respective complementary single-stranded target DNA. Following the annealing step, the temperature is maintained or adjusted to a temperature optimum of the DNA polymerase being used, which allows incorporation of complementary nucleotides at the 3' ends of the annealed oligonucleotide primers thereby recreating double stranded target DNA. Using a heat-stable DNA polymerase, the cycle of denaturing, annealing and extension may be repeated as many times as necessary to generate a desired product, without the addition of polymerase after each heat denaturation (see "Current Protocols in Molecular Biology", F. M. Ausubel et al., John Wiley and Sons, Inc., 1998).

In some embodiments, denaturing the target nucleic acid is conducted at about 90° C.-100° C. for from about 10 seconds to 10 minutes, preferably for the first circle for from about 1 to 8 minutes. In some embodiments, annealing the primers with the target nucleic acid is conducted at about 5° C.-60° C. for from about 3 seconds to 10 minutes. In some embodiments, incubating the nucleic acid-primer hybrid to allow the nucleic acid polymerase to amplify the target nucleic acid is conducted at about 60° C.-90° C. for from about 1 minute to 15 minutes.

In some embodiments, the incubation step is repeated at least 1 time, 5 times, 10 times, 15 times, 20 times, 25 times, 30 times, 35 times or 40 times. In some embodiments, the incubation step is repeated from about 20 times to about 50 times.

In some embodiments, the nucleic acid other than the target nucleic acid is not amplified in step (b) substantially. In some embodiments, the molar percentage of undesired nucleic acid in the product obtained after the incubation step is less than 20%, 15%, 10%, 5%, 3%, 2% or 1%.

The amplification method of the present disclosure can be used to construct DNA sequencing library. In some embodiments, the product obtained from the incubation step can be used as DNA sequencing library directly without enzyme digestion to reduce undesired amplification product. In some embodiments, the product obtained from the incubation step can be used as DNA sequencing library after the ligation of adaptor tags, but without enzyme digestion to reduce undesired amplification product.

"DNA sequencing library" as described in the present disclosure refers to a collection of DNA segments, in an abundance that can be sequenced, wherein one end or both ends of each segment in the collection of DNA segments contains a specific sequence partly or completely complementary to the primers used in sequencing, and thereby can be directly used in the subsequent DNA sequencing.

Some examples for construction of DNA sequencing library are shown in FIGS. 1-4 and 6-7.

In some embodiments, the method is used for selective enrichment of mutant nucleic acid in a sample comprising wildtype and mutant nucleic acid.

Figure 5:
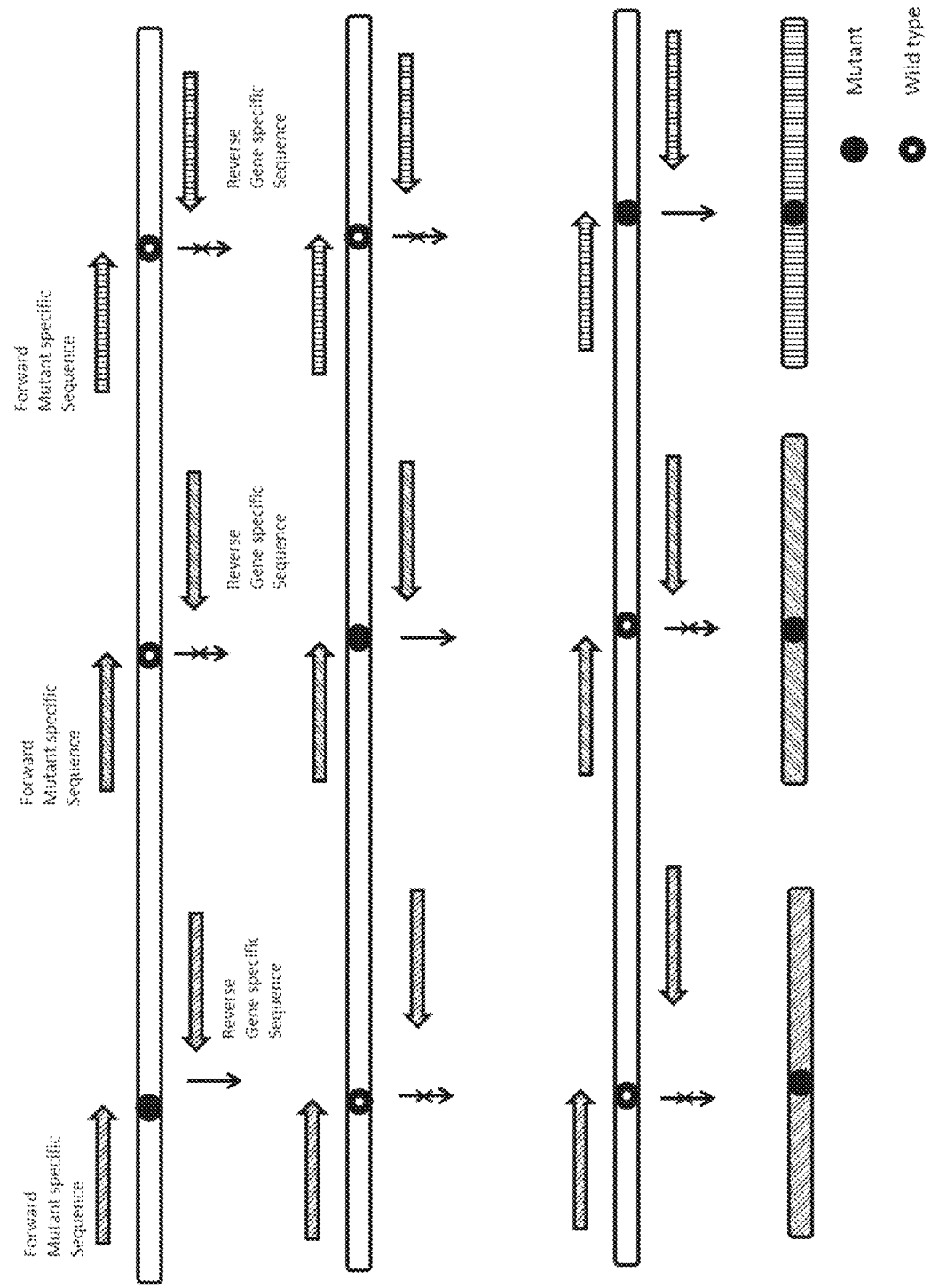
FIG. 5: Selectively amplification of mutant sequence in genomic DNA by multiplex PCR.
Figure 6:
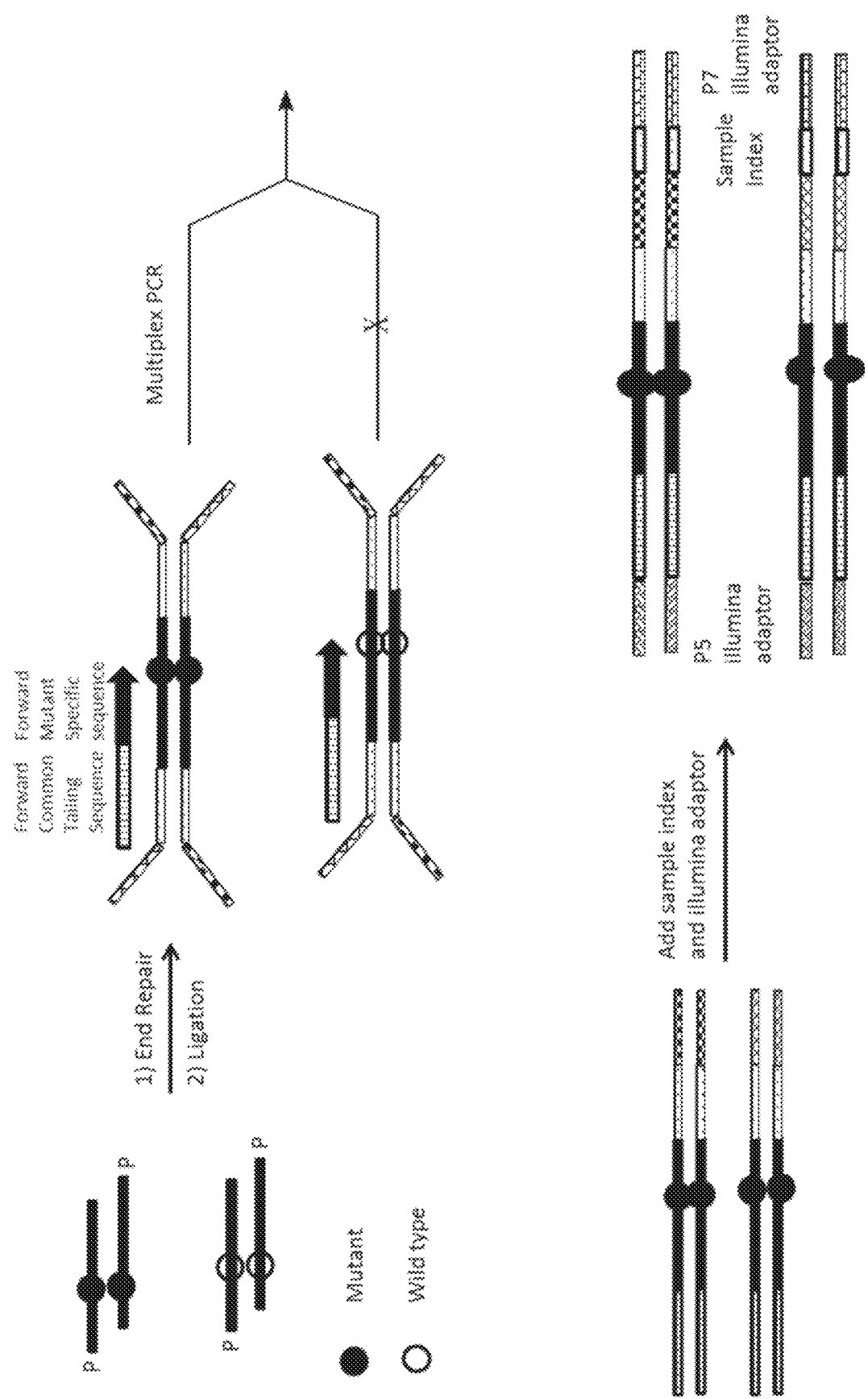
FIG. 6: Mutant enriched NGS library construction for fragmented DNA by multiplex PCR.
Figure 7:
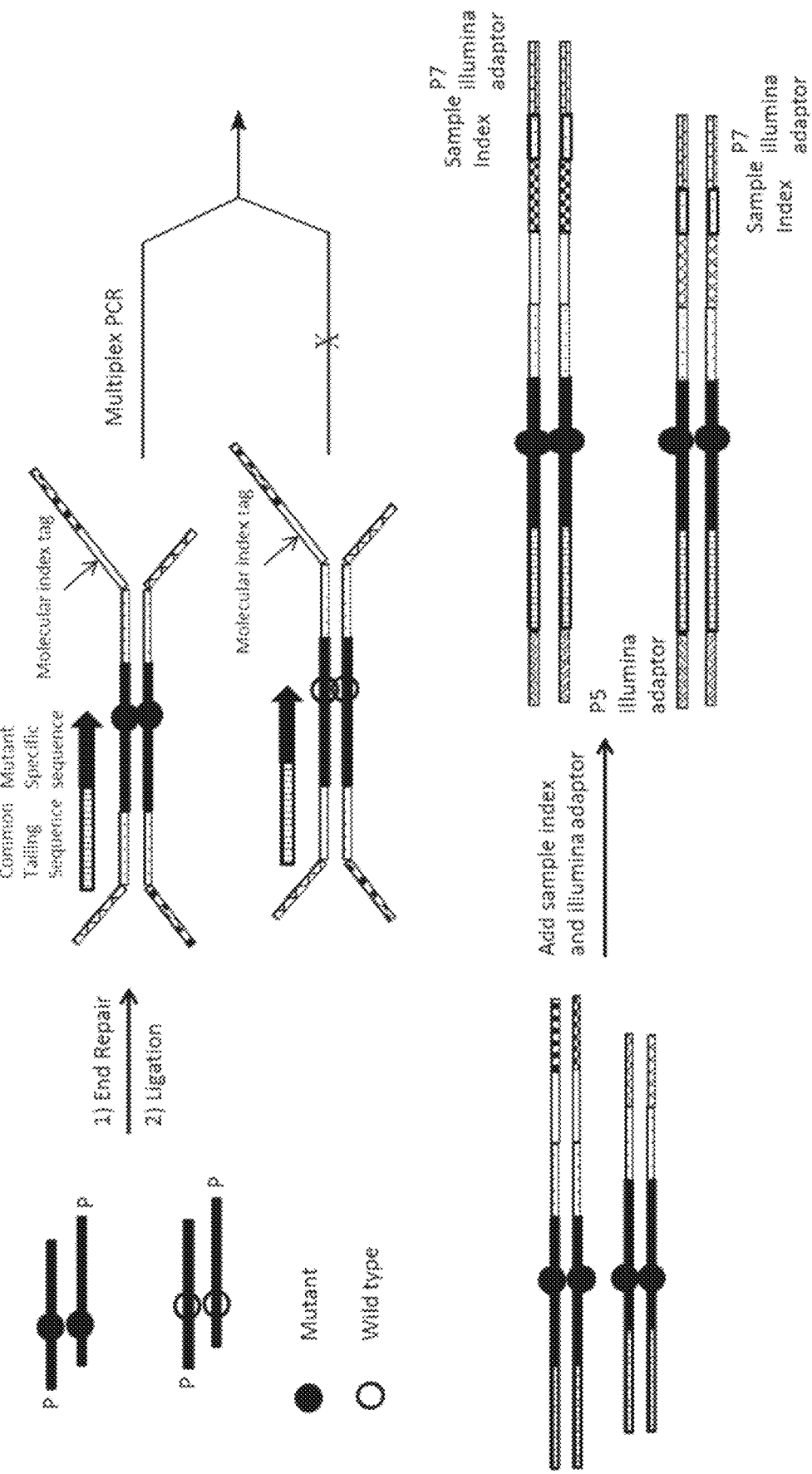
FIG. 7: Mutant enriched NGS library construction for fragmented DNA with single stranded molecular index tag by multiplex PCR.
Figure 8:
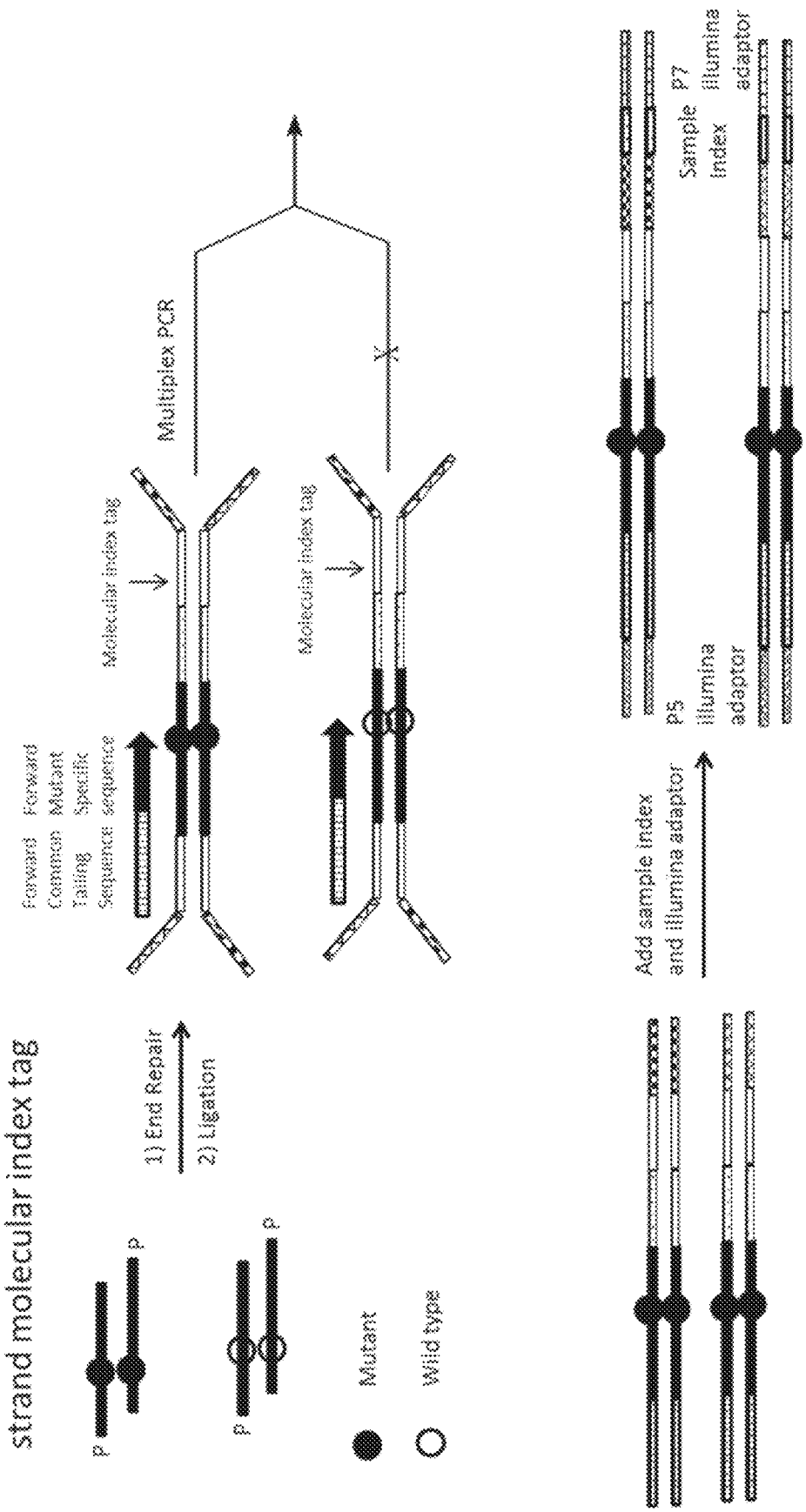
FIG. 8: NGS library construction for fragmented DNA with double stranded molecular index tags by multiplex PCR.
Figure 9:
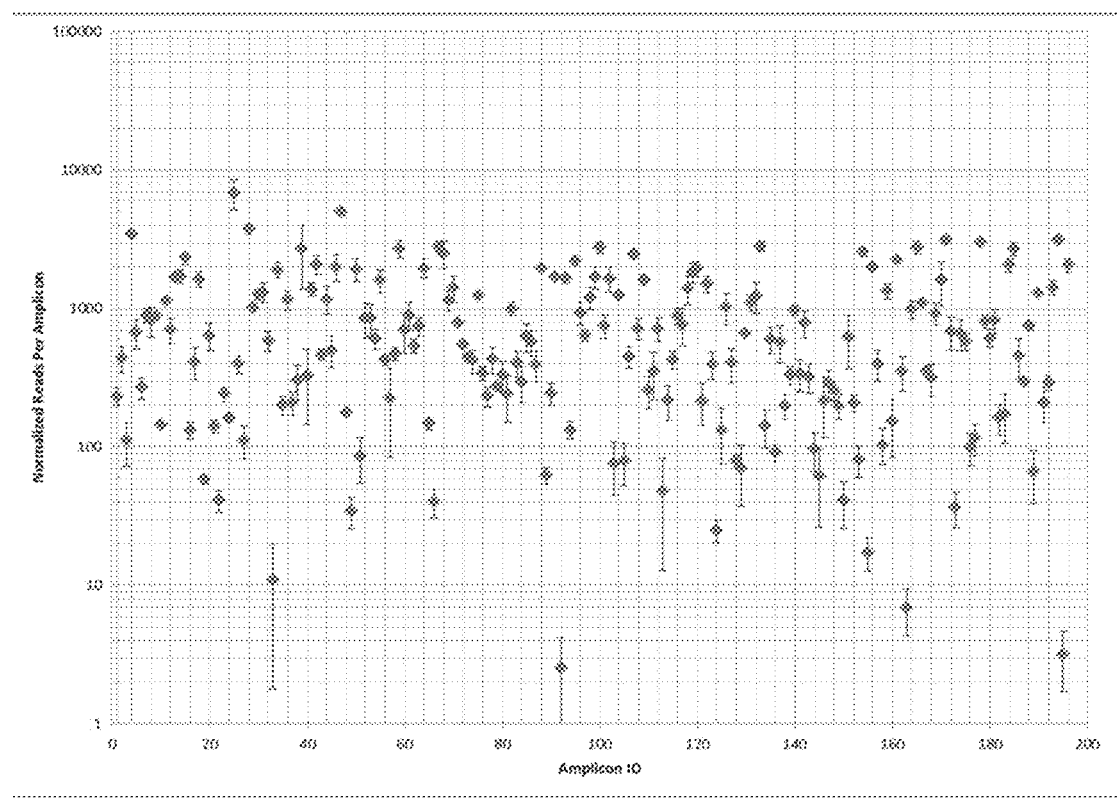
FIG. 9. The normalized reads per amplicon in a 196-plex reaction on a genomic DNA sample across six individual reactions followed by sequencing run on a MiSeq sequencer in Example 1.
Figure 10:
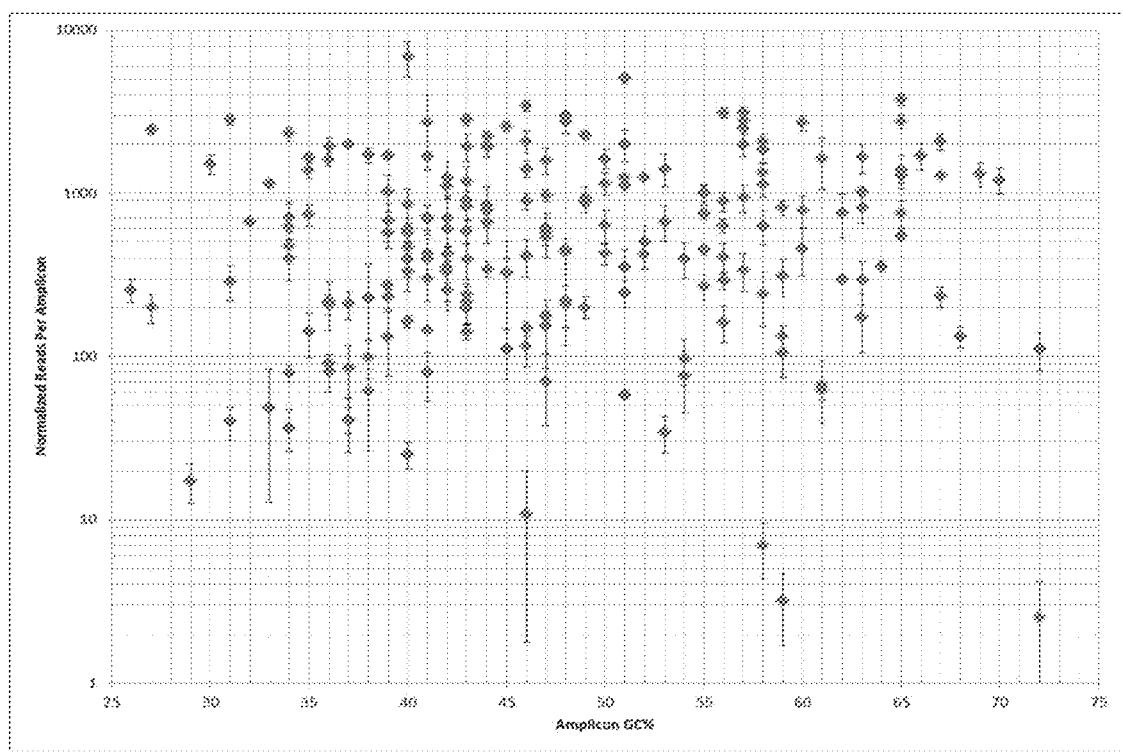
FIG. 10. The normalized reads per amplicon v.s. amplicon GC percentage in a 196-plex reaction on a genomic DNA sample across six individual reactions followed by sequencing run on a MiSeq sequencer in Example 1.
Figure 11:
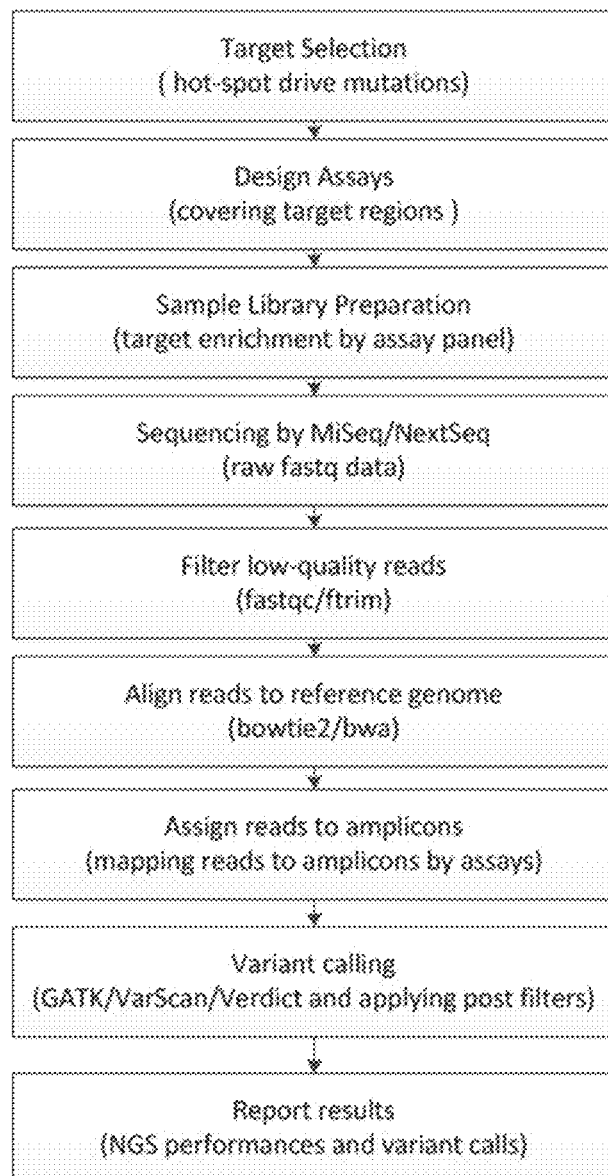
FIG. 11. General working flow for multiplex PCR reaction assay design and NGS data analysis.

Some examples for selective enrichment of mutant nucleic acid are shown in FIG. 5-7.

Another aspect of the present disclosure provides method of sequencing a target nucleic acid, wherein the method comprises: (a) providing a reaction mixture comprising: (i) a nucleic acid sample, (ii) at least 20 different pairs of primers, wherein at least one primer of each primer pair is complementary to a portion of the target nucleic acid and comprises a blocking group capable of blocking polymerase extension ("blocking primer"), (iii) nucleic acid polymerase, and (iv) de-blocking agent capable of enabling polymerization of the target nucleic acid by said nucleic acid polymerase; (b) incubating the reaction mixture under a condition for amplification of the target nucleic acid; (c) determining the sequence of the products obtained from step (b).

The terms "sequencing" as used in the present disclosure refers to any and all biochemical methods that may be used to determine the identity and order of nucleotide bases including but not limited to adenine, guanine, cytosine and thymine, in one or more molecules of DNA. In some embodiments, the method is use for sequencing by capillary electrophoresis, PCR or high throughput sequencing (e.g., next-generation sequencing (NGS)).

Yet another aspect of the present disclosure provides a method of sequencing a target nucleic acid, wherein the method comprises: (a) providing a reaction mixture comprising: (i) a nucleic acid sample, (ii) at least 20 different pairs of primers, wherein at least one primer of each primer pairs is complementary to a portion of the target nucleic acid and comprises a blocking group capable of blocking polymerase extension ("blocking primer"), (iii) nucleic acid polymerase, and (iv) de-blocking agent capable of enabling polymerization of the target nucleic acid by said nucleic acid polymerase; (b) incubating the reaction mixture under a condition for amplification of the target nucleic acid; (c) adding adaptor tag, molecular index tag and/or sample index tag to the product obtained from step (b); (d) determining the sequence of the products obtained from step (c).

In some embodiments, in the step (c), adaptor tag, molecular index tag and/or sample index tag is attached to the target nucleic acid obtained from step (b). The adaptor tag, molecular index tag and/or sample index tag can be attached according to the method mentioned above.

Yet another aspect of the present disclosure provides a kit of amplifying a target nucleic acid, wherein the kit comprises: (i) at least 20 different pairs of primers, wherein at least one primer of each primer pairs is complementary to a portion of the target nucleic acid and comprises a blocking group capable of blocking polymerase extension, (ii) nucleic acid polymerase, and (iii) de-blocking agent capable of enabling polymerization of the target nucleic acid by said nucleic acid polymerase.

In some embodiments, the kit further comprises one or more agents selected from dNTPs, $Mg^{2+}$ (e.g., $MgCl_2$), Bovin Serum Albumin, pH buffer (e.g., Tris HCL), glycerol, DNase inhibitor, RNase, $SO4^{2-}$, $Cl^-$, $K^+$, $Ca^{2+}$, $Na^+$, and $(NH_4)^+$.

In some embodiments, the kit further comprises an instruction showing how to conduct the amplification of the target nucleic acid (such as showing those methods of the present disclosure).

Yet another aspect of the present disclosure provides a method of amplifying a target nucleic acid, wherein the method comprises: (a) providing a reaction mixture comprising: (i) a nucleic acid sample, (ii) at least one primer that is complementary to a portion of the target nucleic acid and comprises a blocking group capable of blocking polymerase extension ("blocking primer"), wherein the blocking primer is modified so as to decrease the amplification of undesired nucleic acid, (iii) nucleic acid polymerase, and (iv) de-blocking agent capable of enabling polymerization of the target nucleic acid by said nucleic acid polymerase; (b) incubating the reaction mixture under a condition for amplification of the target nucleic acid.

Yet another aspect of the present disclosure provides a kit of amplifying a target nucleic acid, wherein the kit comprises: (i) at least one primer that is complementary to a portion of the target nucleic acid and comprises a blocking group capable of blocking polymerase extension ("blocking primer"), wherein the blocking primer is modified so as to decrease the amplification of undesired nucleic acid, (ii) nucleic acid polymerase, and (iii) de-blocking agent capable of enabling polymerization of the target nucleic acid by said nucleic acid polymerase.

Any embodiment following any aspect of the present disclosure can be applied to other aspects of the present disclosure, as long as the resulted embodiments are possible or reasonable for a person skilled in the art.

It is understood that as used herein and in the appended claims, the singular forms "a," "an," and "the" include the plural reference unless the context clearly dictates otherwise. Thus, for example, a reference to a "bridge probe" is a reference to one or more bridge probes, and includes equivalents thereof known to those skilled in the art and so forth.

All publications and patents cited in this specification are herein incorporated by reference to their entirety.

EXAMPLES

The invention will be more readily understood with reference to the following examples, which are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Example 1. Multiplex PCR Amplification of Genomic DNA Target

A multiplex polymerase chain reaction was performed to selectively amplify 196 amplicons (the products amplified from target nucleic acid regions) across human genomic DNA. Each primer pair contains two primers with dideoxynucleoside terminated at its 3' end and can selectively hybridize target nucleic acid. The sequence of each primer pair is shown in Table 3. The boldfaced sequences in each primer are the sequences for the following step of the library construction and other sequences in each primer are the sequences for selectively hybridizing target nucleic acid.

TABLE 3

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| 1 | PDGFRA | 1F | 1 | ACACTCTTTCCCTACACGACGCTCTTCCGATCTAAACAAGCTCTCATGTCTGAACT | 1R | 2 | GTGACTGGAGTTCAGACGTGTGCTCTTCCGATCTCATGTGGTTGTGAAAACTGTTCAA | 4 |
| 2 | CDKN2A | 2F | 3 | ACACTCTTTCCCTACACGACGCTCTTCCGATCTCATGGTTACTGCCTCTGGTG | 2R | 4 | GTGACTGGAGTTCAGACGTGTGCTCTTCCGATCTCACCAGCGTGTCCAGGAA | 9 |
| 3 | SMARCB1 | 3F | 5 | ACACTCTTTCCCTACACGACGCTCTTCCGATCTACATGGAGATCGATGGGCA | 3R | 6 | GTGACTGGAGTTCAGACGTGTGCTCTTCCGATCTGCTGCCTGTCAGGCAGAT | 22 |
| 4 | TP53 | 4F | 7 | ACACTCTTTCCCTACACGACGCTCTTCCGATCTCBGAGGTCACTCACCTGG | 4R | 8 | GTGACTGGAGTTCAGACGTGTGCTCTTCCGATCTGGGGAGAAGTAAGTATATACacagt | 17 |
| 5 | RB1 | 5F | 9 | ACACTCTTTCCCTACACGACGCTCTTCCGATCTAGAACAAAACCATGTAATAAAATTCTGA | 5R | 10 | GTGACTGGAGTTCAGACGTGTGCTCTTCCGATCTATTGTAACAGCATACAAGGATCTTCC | 13 |
| 6 | SMAD4 | 6F | 11 | ACACTCTTTCCCTACACGACGCTCTTCCGATCTTTCATTTGTTTTCCCCTTTAAACAATTA | 6R | 12 | GTGACTGGAGTTCAGACGTGTGCTCTTCCGATCTGAGTAATGGTAGGTAATCTGTTTCTTAC | 18 |
| 7 | ATM | 7F | 13 | ACACTCTTTCCCTACACGACGCTCTTCCGATCTTGAGGGTACCAGAGACAGT | 7R | 14 | GTGACTGGAGTTCAGACGTGTGCTCTTCCGATCTAATTTTTATGTACTTTTCATTCCCTGAA | 11 |
| 8 | RB1 | 8F | 15 | ACACTCTTTCCCTACACGACGCTCTTCCGATCTYTGTTATTTAGTTTTGAAACACAGAGAA | 8R | 16 | GTGACTGGAGTTCAGACGTGTGCTCTTCCGATCTCTCCACACACTCCAGTTAGGTA | 13 |
| 9 | ATM | 9F | 17 | ACACTCTTTCCCTACACGACGCTCTTCCGATCTTCTATGCAAGATACACAGTAAAGGTTC | 9R | 18 | GTGACTGGAGTTCAGACGTGTGCTCTTCCGATCTGTGCACTGAAAGAGGATCGT | 11 |
| 10 | KDR | 10F | 19 | ACACTCTTTCCCTACACGACGCTCTTCCGATCTCTCTGACAAGAGCATGCCATAG | 10R | 20 | GTGACTGGAGTTCAGACGTGTGCTCTTCCGATCTCGTTTCAGATCCACAGGGATTG | 4 |
| 11 | JAK3 | 11F | 21 | ACACTCTTTCCCTACACGACGCTCTTCCGATCTCCACCTGATTGCATGCCA | 11R | 22 | GTGACTGGAGTTCAGACGTGTGCTCTTCCGATCTGGCACTTCTCCAGCCCAA | 19 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| 12 | PIK3CA | 12F | 23 | ACACTCTTTCCCTACACGACGCTCTTCCGATCTTGACRAAGAACAGCTCAAAGC | 12R | 24 | GTGACTGGAGTTCAGACGTGTGCTCTTCCGATCTACTGAATTTGGCTGATCTCAGC | 3 |
| 13 | NPM1 | 13F | 25 | ACACTCTTTCCCTACACGACGCTCTTCCGATCTATGTCTATGAAGTGTTGTGGTTCC | 13R | 26 | GTGACTGGAGTTCAGACGTGTGCTCTTCCGATCTAAAATTTTCCGTCTTATTTCATTTCTGT | 5 |
| 14 | RET | 14F | 27 | ACACTCTTTCCCTACACGACGCTCTTCCGATCTGGTCNGATTCCAGTTAAATGG | 14R | 28 | GTGACTGGAGTTCAGACGTGTGCTCTTCCGATCTACGCAAAGTGATGTGTAAGTGTG | 10 |
| 15 | FGFR1 | 15F | 29 | ACACTCTTTCCCTACACGACGCTCTTCCGATCTACCCTGCTTGCAGGATGG | 15R | 30 | GTGACTGGAGTTCAGACGTGTGCTCTTCCGATCTCCAGTGATGGGTTGTAAACCTC | 8 |
| 16 | FLT3 | 16F | 31 | ACACTCTTTCCCTACACGACGCTCTTCCGATCTATTTTCGTGGAAGTGGGTTACC | 16R | 32 | GTGACTGGAGTTCAGACGTGTGCTCTTCCGATCTGCTTCCCAGCTGGGTCAT | 13 |
| 17 | RB1 | 17F | 33 | ACACTCTTTCCCTACACGACGCTCTTCCGATCTTGTGGTTTTAATTTCATCATGTTTCATA | 17R | 34 | GTGACTGGAGTTCAGACGTGTGCTCTTCCGATCTACTGCAGCAGATATGTAAGCAAAA | 13 |
| 18 | MLH1 | 18F | 35 | ACACTCTTTCCCTACACGACGCTCTTCCGATCTAAGTAGTGATAAGGTCTATGCCCA | 18R | 36 | GTGACTGGAGTTCAGACGTGTGCTCTTCCGATCTAGACAGATATTTCTAGTGGCAGGG | 3 |
| 19 | SMAD4 | 19F | 37 | ACACTCTTTCCCTACACGACGCTCTTCCGATCTCCTGTTCACAATGAGCTTGCA | 19R | 38 | GTGACTGGAGTTCAGACGTGTGCTCTTCCGATCTTTTCCTGTATTTAGATTGATTTAGTGGT | 18 |
| 20 | CDH1 | 20F | 39 | ACACTCTTTCCCTACACGACGCTCTTCCGATCTTCGACACCCGATTCAAAGTG | 20R | 40 | GTGACTGGAGTTCAGACGTGTGCTCTTCCGATCTGGTTTCATAACCCACAGATCCAT | 16 |
| 21 | ATM | 21F | 41 | ACACTCTTTCCCTACACGACGCTCTTCCGATCTTGCYTCTGGCTGGATTTAAAT | 21R | 42 | GTGACTGGAGTTCAGACGTGTGCTCTTCCGATCTTTTTTGGTTTTAAAATTAATGTTGGCA | 11 |
| 22 | PTEN | 22F | 43 | ACACTCTTTCCCTACACGACGCTCTTCCGATCTGCRTGCAGATAATGACAAGGAA | 22R | 44 | GTGACTGGAGTTCAGACGTGTGCTCTTCCGATCTTGACTTGTATGTATGTGATGTGTG | 10 |
| 23 | AKT1 | 23F | 45 | ACACTCTTTCCCTACACGACGCTCTTCCGATCTCGCCACACAGAGAAGTGTTGAG | 23R | 46 | GTGACTGGAGTTCAGACGTGTGCTCTTCCGATCTGTGAGAGCCACGCACACT | 14 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| 24 | FGFR3 | 24F | 47 | ACACTCTTTCCCTACACGACGCTCTTCCGATCTgCCCCTGAGCGTCATCTG | 24R | 48 | GTGACTGGAGTTCAGACGTGTGCTCTTCCGATCTGAGTTCCACTGCAAGGTGT | 4 |
| 25 | RET | 25F | 49 | ACACTCTTTCCCTACACGACGCTCTTCCGATCTCTCTGTGCTGCATTTCAGAGA | 25R | 50 | GTGACTGGAGTTCAGACGTGTGCTCTTCCGATCTCACCCACATGTCATCAAAT | 10 |
| 26 | ATM | 26F | 51 | ACACTCTTTCCCTACACGACGCTCTTCCGATCTGATGAGAAAYTCTCAGGAAACTCTGT | 26R | 52 | GTGACTGGAGTTCAGACGTGTGCTCTTCCGATCTTCAGGAAGTCACTGATGTGAAG | 11 |
| 27 | FLT3 | 27F | 53 | ACACTCTTTCCCTACACGACGCTCTTCCGATCTTTCCATTCTTACCAAACTCTAAATTTTC | 27R | 54 | GTGACTGGAGTTCAGACGTGTGCTCTTCCGATCTACCTAAATTGCTTCAGAGATGAAA | 13 |
| 28 | KRAS | 28F | 55 | ACACTCTTTCCCTACACGACGCTCTTCCGATCTGCAGAAAACAGATCTGTATTTATTTCA | 28R | 56 | GTGACTGGAGTTCAGACGTGTGCTCTTCCGATCTTTCCTACTAGGACCATAGGTACA | 12 |
| 29 | STK11 | 29F | 57 | ACACTCTTTCCCTACACGACGCTCTTCCGATCTCTGCCCCGCAGGTACTTCT | 29R | 58 | GTGACTGGAGTTCAGACGTGTGCTCTTCCGATCTCATTGTGCACAAGGACATCAAG | 19 |
| 30 | FLT3 | 30F | 59 | ACACTCTTTCCCTACACGACGCTCTTCCGATCTTGGGTATCCATCCGAGAAACA | 30R | 60 | GTGACTGGAGTTCAGACGTGTGCTCTTCCGATCTTAGAAAAGAACGTGTGAAATAAGCT | 13 |
| 31 | ABL1 | 31F | 61 | ACACTCTTTCCCTACACGACGCTCTTCCGATCTGCAACAAGCCCACTGTCTATG | 31R | 62 | GTGACTGGAGTTCAGACGTGTGCTCTTCCGATCTGAAGAAATACAGCCTGACGGTG | 9 |
| 32 | VHL | 32F | 63 | ACACTCTTTCCCTACACGACGCTCTTCCGATCTCCCAGGTCATCTTCTGCAATC | 32R | 64 | GTGACTGGAGTTCAGACGTGTGCTCTTCCGATCTCGCATCCACAGCTACCGA | 3 |
| 33 | ATM | 33F | 65 | ACACTCTTTCCCTACACGACGCTCTTCCGATCTAAAGATCACCTTCAGAAGTCACAG | 33R | 66 | GTGACTGGAGTTCAGACGTGTGCTCTTCCGATCTTGTTACCATTTTCTCATTCAGTGTCAT | 11 |
| 34 | KDR | 34F | 67 | ACACTCTTTCCCTACACGACGCTCTTCCGATCTATTTTATTTCCTCCCTGGAAGTCC | 34R | 68 | GTGACTGGAGTTCAGACGTGTGCTCTTCCGATCTGTCAAGAGTAAGGAAAGATTCAGACT | 4 |
| 35 | FGFR2 | 35F | 69 | ACACTCTTTCCCTACACGACGCTCTTCCGATCTTCACCATCCTGTGTGCAGG | 35R | 70 | GTGACTGGAGTTCAGACGTGTGCTCTTCCGATCTTCTCCATCTCTGACACCAGA | 10 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| 36 | NRAS | 36F | 71 | ACACTCTTTCCC TACACGACGCTC TTCCGATCTCAT GTATTGGTCTCT CATGGCAC | 36R | 72 | GTGACTGGAGT TCAGACGTGTGC TCTTCCGATCTTT CAATTTTTATTAA AAACCACAGGG A | 1 |
| 37 | ERBB4 | 37F | 73 | ACACTCTTTCCC TACACGACGCTC TTCCGATCTACC AGTGACTAGAAA GATCAAATTCC | 37R | 74 | GTGACTGGAGT TCAGACGTGTGC TCTTCCGATCTA GAAACAAGACT CAGAGTTAGGG G | 2 |
| 38 | RB1 | 38F | 75 | ACACTCTTTCCC TACACGACGCTC TTCCGATCTTGA CATGTAAGGAT AATTGTCAGTGA C | 38R | 76 | GTGACTGGAGT TCAGACGTGTGC TCTTCCGATCTA AAGATCTAGATG CAAGATTATTTTT GG | 13 |
| 39 | SMO | 39F | 77 | ACACTCTTTCCC TACACGACGCTC TTCCGATCTGTG CAGAACATCAAG TTCAACAGT | 39R | 78 | GTGACTGGAGT TCAGACGTGTGC TCTTCCGATCTC AGGACATGCACA GCTACATC | 7 |
| 40 | PIK3CA | 40F | 79 | ACACTCTTTCCC TACACGACGCTC TTCCGATCTTAG GTGGAATGAATG GCTGAATTA | 40R | 80 | GTGACTGGAGT TCAGACGTGTGC TCTTCCGATCTG AAAGGGTGCTA AAGAGGTAAAG | 3 |
| 41 | KRAS | 41F | 81 | ACACTCTTTCCC TACACGACGCTC TTCCGATCTTTC GTCCACAAAATG ATTCTGAATTAG | 41R | 82 | GTGACTGGAGT TCAGACGTGTGC TCTTCCGATCTC AGTCATTTTCAG CAGGCCTTATA | 12 |
| 42 | SMAD4 | 42F | 83 | ACACTCTTTCCC TACACGACGCTC TTCCGATCTTGG YGTTCCATTGCTT ACTTT | 42R | 84 | GTGACTGGAGT TCAGACGTGTGC TCTTCCGATCTT GTCCACAGGAC AGAAGC | 18 |
| 43 | PIK3CA | 43F | 85 | ACACTCTTTCCC TACACGACGCTC TTCCGATCTTTCC ATACTACTCATGA GGTGTTTATTC | 43R | 86 | GTGACTGGAGT TCAGACGTGTGC TCTTCCGATCTT GAAAGACGATG GACAAGTAATGG | 3 |
| 44 | RB1 | 44F | 87 | ACACTCTTTCCC TACACGACGCTC TTCCGATCTAGA AGGCAACTTGAC AAGAGAAAT | 44R | 88 | GTGACTGGAGT TCAGACGTGTGC TCTTCCGATCTA ATAATTGAAGAA ATTCATTCATGTG CA | 13 |
| 45 | CSF1R | 45F | 89 | ACACTCTTTCCC TACACGACGCTC TTCCGATCTTTCT GCTCAGAGCTCA AGTTC | 45R | 90 | GTGACTGGAGT TCAGACGTGTGC TCTTCCGATCTC CTGAGCAGCTAT GTCACAG | 5 |
| 46 | PTEN | 46F | 91 | ACACTCTTTCCC TACACGACGCTC TTCCGATCTCTG GTATGTATTTAAC CATGCAGATCC | 46R | 92 | GTGACTGGAGT TCAGACGTGTGC TCTTCCGATCTG TGAAGATATATTC CTCCAATTCAGG AC | 10 |
| 47 | ATM | 47F | 93 | ACACTCTTTCCC TACACGACGCTC TTCCGATCTTGTT | 47R | 94 | GTGACTGGAGT TCAGACGTGTGC TCTTCCGATCTG | 11 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| | | | | GGAAGCTGCTTGGG | | | TTATTTGAAGATAAAGAACTTCRGTGG | |
| 48 | KDR | 48F | 95 | ACACTCTTTCCCTACACGACGCTCTTCCGATCTGCTGAGCATTAGCTTGCAAGA | 48R | 96 | GTGACTGGAGTTCAGACGTGTGCTCTTCCGATCTCCTCTTTCTTCCTGAATGCTGAAA | 4 |
| 49 | GNAS | 49F | 97 | ACACTCTTTCCCTACACGACGCTCTTCCGATCTTTCAGGACCTGCTTCGCT | 49R | 98 | GTGACTGGAGTTCAGACGTGTGCTCTTCCGATCTCAGTAAGCCAACTGTTACCTTTT | 20 |
| 50 | PIK3CA | 50F | 99 | ACACTCTTTCCCTACACGACGCTCTTCCGATCTTGCACAATAAAACAGTTAGCCAGA | 50R | 100 | GTGACTGGAGTTCAGACGTGTGCTCTTCCGATCTTCTCAAACAGGAGAAGAAGGATGA | 3 |
| 51 | RB1 | 51F | 101 | ACACTCTTTCCCTACACGACGCTCTTCCGATCTTCTGCATTGGTGCTAAAAGTTTCT | 51R | 102 | GTGACTGGAGTTCAGACGTGTGCTCTTCCGATCTTGTAATAATTAAATTGGCATTCCTTTGG | 13 |
| 52 | MPL | 52F | 103 | ACACTCTTTCCCTACACGACGCTCTTCCGATCTCATCTAGTGCTGGGCCTCA | 52R | 104 | GTGACTGGAGTTCAGACGTGTGCTCTTCCGATCTGACCAGGTGGAGCCGAAG | 1 |
| 53 | STK11 | 53F | 105 | ACACTCTTTCCCTACACGACGCTCTTCCGATCTTGCATAGCCAGGGCATTG | 53R | 106 | GTGACTGGAGTTCAGACGTGTGCTCTTCCGATCTGTAGGCACGTGCTAGGGG | 19 |
| 54 | FGFR1 | 54F | 107 | ACACTCTTTCCCTACACGACGCTCTTCCGATCTCTGTTTCTTTCTCCTCTGAAGAGG | 54R | 108 | GTGACTGGAGTTCAGACGTGTGCTCTTCCGATCTCTAGTGCAGTTCCAGATGAACAC | 8 |
| 55 | TP53 | 55F | 109 | ACACTCTTTCCCTACACGACGCTCTTCCGATCTGAAAATGTTTCCTGACTCAGAGGG | 55R | 110 | GTGACTGGAGTTCAGACGTGTGCTCTTCCGATCTGTGACCCGAAGGCAGTC | 17 |
| 56 | RB1 | 56F | 111 | ACACTCTTTCCCTACACGACGCTCTTCCGATCTTTTCCTTTGTAGTGTCCATAAATTCTTT | 56R | 112 | GTGACTGGAGTTCAGACGTGTGCTCTTCCGATCTTGTTGAAGAAGTATGATGTATTGTTTGC | 13 |
| 57 | CDH1 | 57F | 113 | ACACTCTTTCCCTACACGACGCTCTTCCGATCTCGTCGTAATCACCACACTGAAAG | 57R | 114 | GTGACTGGAGTTCAGACGTGTGCTCTTCCGATCTGGGAGGCTGTATACACCATATTGA | 16 |
| 58 | FLT3 | 58F | 115 | ACACTCTTTCCCTACACGACGCTCTTCCGATCTTCACATTGCCCCTGACAAC | 58R | 116 | GTGACTGGAGTTCAGACGTGTGCTCTTCCGATCTCTTCACCACTTTCCCGTGG | 13 |
| 59 | PDGFRA | 59F | 117 | ACACTCTTTCCCTACACGACGCTCTTCCGATCTTCCT | 59R | 118 | GTGACTGGAGTTCAGACGTGTGCTCTTCCGATCTA | 4 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| | | | | GAGTCATTTCTT CCTTTTCC | | | CTATGTGTCGAA AGGCAGTGTA | |
| 60 | HNF1A | 60F | 119 | ACACTCTTTCCC TACACGACGCTC TTCCGATCTATG AGCTACCAACCA AGAAGG | 60R | 120 | GTGACTGGAGT TCAGACGTGTGC TCTTCCGATCTC AGATCCTGTTCC AGGCCTAT | 12 |
| 61 | MET | 61F | 121 | ACACTCTTTCCC TACACGACGCTC TTCCGATCTATTT TGGTCTTGCCAG AGACATG | 61R | 122 | GTGACTGGAGT TCAGACGTGTGC TCTTCCGATCTG CTTTGGAAAGTC TGCAAACTCAA | 7 |
| 62 | MET | 62F | 123 | ACACTCTTTCCC TACACGACGCTC TTCCGATCTTTCC CTGCAACAGCTG AATC | 62R | 124 | GTGACTGGAGT TCAGACGTGTGC TCTTCCGATCTTC TCAATGGGCAAT GAAAATGTA | 7 |
| 63 | MET | 63F | 125 | ACACTCTTTCCC TACACGACGCTC TTCCGATCTGCA GTGCTAACCAAG TTCTTTCT | 63R | 126 | GTGACTGGAGT TCAGACGTGTGC TCTTCCGATCTCA TGGAGTATACTT TTGTGGTTTGC | 7 |
| 64 | AKT1 | 64F | 127 | ACACTCTTTCCC TACACGACGCTC TTCCGATCTACR ATGACTTCCTTCT TGAGGA | 64R | 128 | GTGACTGGAGT TCAGACGTGTGC TCTTCCGATCTC CAGGATCACCTT GCCGAA | 14 |
| 65 | GNA11 | 65F | 129 | ACACTCTTTCCC TACACGACGCTC TTCCGATCTCTG TGTCCTTTCAGG ATGGTG | 65R | 130 | GTGACTGGAGT TCAGACGTGTGC TCTTCCGATCTCC ACTGCTTTGAGA ACGTGAC | 19 |
| 66 | GNAS | 66F | 131 | ACACTCTTTCCC TACACGACGCTC TTCCGATCTCYC CACCAGCATGTT TGA | 66R | 132 | GTGACTGGAGT TCAGACGTGTGC TCTTCCGATCTCT TTGCTTCTGTGT TGTTAGGG | 20 |
| 67 | KIT | 67F | 133 | ACACTCTTTCCC TACACGACGCTC TTCCGATCTTTCT AGTGCATTCAAG CACAATGG | 67R | 134 | GTGACTGGAGT TCAGACGTGTGC TCTTCCGATCTC CAATTTAAGGGG ATGTTTAGGCT | 4 |
| 68 | PTPN11 | 68F | 135 | ACACTCTTTCCC TACACGACGCTC TTCCGATCTCCA ATGGACTATTTTA GAAGAAATGGA | 68R | 136 | GTGACTGGAGT TCAGACGTGTGC TCTTCCGATCTG GGCAATTAAAAG AGAAGAATGGA | 12 |
| 69 | ALK | 69F | 137 | ACACTCTTTCCC TACACGACGCTC TTCCGATCTGTC TCTCGGAGGAA GGACTT | 69R | 138 | GTGACTGGAGT TCAGACGTGTGC TCTTCCGATCTG CAGAGAGGGAT GTAACCAAATT | 2 |
| 70 | JAK3 | 70F | 139 | ACACTCTTTCCC TACACGACGCTC TTCCGATCTTGA CCTTAGCAGGAT CCAGG | 70R | 140 | GTGACTGGAGT TCAGACGTGTGC TCTTCCGATCTC CTGTCGGTGAGC ACTGA | 19 |
| 71 | NRAS | 71F | 141 | ACACTCTTTCCC TACACGACGCTC TTCCGATCTTGA AAGCTGTACCAT ACCTGTCT | 71R | 142 | GTGACTGGAGT TCAGACGTGTGC TCTTCCGATCTC CAGTTCGTGGGC TTGTT | 1 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| 72 | BRAF | 72F | 143 | ACACTCTTTCCCTACACGACGCTCTTCCGATCTGTCACAATGTCACCACATTACATACT | 72R | 144 | GTGACTGGAGTTCAGACGTGTGCTCTTCCGATCTTCTACCAAGTGTTTTCTTGATAAAAAC | 7 |
| 73 | ATM | 73F | 145 | ACACTCTTTCCCTACACGACGCTCTTCCGATCTATTTGACCGTGGAGAAGTAGAATC | 73R | 146 | GTGACTGGAGTTCAGACGTGTGCTCTTCCGATCTGAGAGAGCCAAAGTACCATAGGTA | 11 |
| 74 | KRAS | 74F | 147 | ACACTCTTTCCCTACACGACGCTCTTCCGATCTTCATGTACTGGTCCCTCATTGC | 74R | 148 | GTGACTGGAGTTCAGACGTGTGCTCTTCCGATCTCAAGAGACAGGTTTCTCCATCA | 12 |
| 75 | MET | 75F | 149 | ACACTCTTTCCCTACACGACGCTCTTCCGATCTATGATAGCCGTCTTTAACAAGCTC | 75R | 150 | GTGACTGGAGTTCAGACGTGTGCTCTTCCGATCTCAGAAATGGTTTCAAATGAATCTGT | 7 |
| 76 | EGFR | 76F | 151 | ACACTCTTTCCCTACACGACGCTCTTCCGATCTCCAGGAACGTACTGGTGAAAAC | 76R | 152 | GTGACTGGAGTTCAGACGTGTGCTCTTCCGATCTCATTTTCCTGACACCAGGGAC | 7 |
| 77 | TP53 | 77F | 153 | ACACTCTTTCCCTACACGACGCTCTTCCGATCTTGTCCCAGAATGCAAGAAGC | 77R | 154 | GTGACTGGAGTTCAGACGTGTGCTCTTCCGATCTGAGCAGCCTCTGGCATT | 17 |
| 78 | SMO | 78F | 155 | ACACTCTTTCCCTACACGACGCTCTTCCGATCTTGTTTTGTGGGCTACAAGAACT | 78R | 156 | GTGACTGGAGTTCAGACGTGTGCTCTTCCGATCTGGGCACTTGCTGCCAGTA | 7 |
| 79 | FBXW7 | 79F | 157 | ACACTCTTTCCCTACACGACGCTCTTCCGATCTTAAACTTACTTTGCCTGTGACTGC | 79R | 158 | GTGACTGGAGTTCAGACGTGTGCTCTTCCGATCTGCACCTATAAGAAAGATGTGCAGA | 4 |
| 80 | SMO | 80F | 159 | ACACTCTTTCCCTACACGACGCTCTTCCGATCTGTGGAGAAGATCAACCTGTTTGC | 80R | 160 | GTGACTGGAGTTCAGACGTGTGCTCTTCCGATCTCTCACCCTCAGCCTTGGG | 7 |
| 81 | MET | 81F | 161 | ACACTCTTTCCCTACACGACGCTCTTCCGATCTGCCTGAATGATGACATTCTTTTCG | 81R | 162 | GTGACTGGAGTTCAGACGTGTGCTCTTCCGATCTGTCAACAAAACAATGTGAGATGTC | 7 |
| 82 | ATM | 82F | 163 | ACACTCTTTCCCTACACGACGCTCTTCCGATCTACCAGAGTTTCAACAAAGTAGCTG | 82R | 164 | GTGACTGGAGTTCAGACGTGTGCTCTTCCGATCTGAGTGGAAGAAGGCACTGTG | 11 |
| 83 | FGFR2 | 83F | 165 | ACACTCTTTCCCTACACGACGCTCTTCCGATCTCGGCAYAGGATGACTGTTAC | 83R | 166 | GTGACTGGAGTTCAGACGTGTGCTCTTCCGATCTAGAGTTAGCACACCAGACTG | 10 |
| 84 | PTEN | 84F | 167 | ACACTCTTTCCCTACACGACGCTC | 84R | 168 | GTGACTGGAGTTCAGACGTGTGC | 10 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| | | | | TTCCGATCTATTTCCATCCTGCAGAAGAAGC | | | TCTTCCGATCTAGGATGGATTCGACTTAGACTTGA | |
| 85 | VHL | 85F | 169 | ACACTCTTTCCCTACACGACGCTCTTCCGATCTGCTCTTTAACAACCTTTGCTTGTC | 85R | 170 | GTGACTGGAGTTCAGACGTGTGCTCTTCCGATCTCAATATCACACTGCCAGGTACTG | 3 |
| 86 | KIT | 86F | 171 | ACACTCTTTCCCTACACGACGCTCTTCCGATCTTCTCTTCCATTGTAGAGCAAATCC | 86R | 172 | GTGACTGGAGTTCAGACGTGTGCTCTTCCGATCTGTTCTCTCCAGAGTGCTCTAAT | 4 |
| 87 | FBXW7 | 87F | 173 | ACACTCTTTCCCTACACGACGCTCTTCCGATCTTATTCAAATAACACCCAATGAAGAATGT | 87R | 174 | GTGACTGGAGTTCAGACGTGTGCTCTTCCGATCTGGTTCACAACTATCAATGAGTTCAT | 4 |
| 88 | EGFR | 88F | 175 | ACACTCTTTCCCTACACGACGCTCTTCCGATCTCTCATCACGCAGCTCATGC | 88R | 176 | GTGACTGGAGTTCAGACGTGTGCTCTTCCGATCTGAGATAAGGAGCCAGGATCCTC | 7 |
| 89 | SMO | 89F | 177 | ACACTCTTTCCCTACACGACGCTCTTCCGATCTCCCAGCATGTCACCAAGATG | 89R | 178 | GTGACTGGAGTTCAGACGTGTGCTCTTCCGATCTGCTTCTGGGACTGGAGTACAG | 7 |
| 90 | FBXW7 | 90F | 179 | ACACTCTTTCCCTACACGACGCTCTTCCGATCTAAGTCCCAACCATGACAAGATTTT | 90R | 180 | GTGACTGGAGTTCAGACGTGTGCTCTTCCGATCTGTGTCCGATCTGTAGATCCACTAA | 4 |
| 91 | PTEN | 91F | 181 | ACACTCTTTCCCTACACGACGCTCTTCCGATCTTGCCAGCTAAAGGTGAAGAT | 91R | 182 | GTGACTGGAGTTCAGACGTGTGCTCTTCCGATCTTTGTACTTTACTTTCATTGGGAGA | 10 |
| 92 | SMAD4 | 92F | 183 | ACACTCTTTCCCTACACGACGCTCTTCCGATCTCTCCATCAAGTATGATGGTGAAGG | 92R | 184 | GTGACTGGAGTTCAGACGTGTGCTCTTCCGATCTCATCCAGCATCCACCAAGTAAT | 18 |
| 93 | PIK3CA | 93F | 185 | ACACTCTTTCCCTACACGACGCTCTTCCGATCTTCTTCCACACAATTAAACAGCATG | 93R | 186 | GTGACTGGAGTTCAGACGTGTGCTCTTCCGATCTGAATTGCACAATCCATGAACAGC | 3 |
| 94 | KIT | 94F | 187 | ACACTCTTTCCCTACACGACGCTCTTCCGATCTTAGTGTATTCACAGAGACTTGGCA | 94R | 188 | GTGACTGGAGTTCAGACGTGTGCTCTTCCGATCTGAAACGTGAGTACCCATTCTCTG | 4 |
| 95 | KIT | 95F | 189 | ACACTCTTTCCCTACACGACGCTCTTCCGATCTCATGTTTCCAATTTTAGCGAGTGC | 95R | 190 | GTGACTGGAGTTCAGACGTGTGCTCTTCCGATCTTGTCCAAGCTGCCTTTTATTGTC | 4 |
| 96 | ATM | 96F | 191 | ACACTCTTTCCCTACACGACGCTCTTCCGATCTTGT | 96R | 192 | GTGACTGGAGTTCAGACGTGTGCTCTTCCGATCTG | 11 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| | | | | GTAGGAAAGGTACAATGATTTCC | | | TGGATTCCTCTAAGTGAAAATCATGA | |
| 97 | SMAD4 | 97F | 193 | ACACTCTTTCCCTACACGACGCTCTTCCGATCTGAAGGACTGTTGCAGATAGCATC | 97R | 194 | GTGACTGGAGTTCAGACGTGTGCTCTTCCGATCTAAGTAGGCAGCCTTTATAAAGCA | 18 |
| 98 | ALK | 98F | 195 | ACACTCTTTCCCTACACGACGCTCTTCCGATCTGGGTGAGGCAGTCTTTACTCA | 98R | 196 | GTGACTGGAGTTCAGACGTGTGCTCTTCCGATCTGGGAAGAAAGGAAATGCATTTCCT | 2 |
| 99 | EGFR | 99F | 197 | ACACTCTTTCCCTACACGACGCTCTTCCGATCTGCGAAGCCACACTGACGT | 99R | 198 | GTGACTGGAGTTCAGACGTGTGCTCTTCCGATCTGCTGCCTCCTGGACTATGTC | 7 |
| 100 | BRAF | 100F | 199 | ACACTCTTTCCCTACACGACGCTCTTCCGATCTTTACATCCACAAAATGGATCCAG | 100R | 200 | GTGACTGGAGTTCAGACGTGTGCTCTTCCGATCTGTAAGTAAAGGAAAACAGTAGATCTCA | 7 |
| 101 | ABL1 | 101F | 201 | ACACTCTTTCCCTACACGACGCTCTTCCGATCTCGAAACTGCCTGGTAGGG | 101R | 202 | GTGACTGGAGTTCAGACGTGTGCTCTTCCGATCTGGAGCCAAGTTCCCCATC | 9 |
| 102 | ERBB4 | 102F | 203 | ACACTCTTTCCCTACACGACGCTCTTCCGATCTACTTACGTGGACATTTCTTGACAC | 102R | 204 | GTGACTGGAGTTCAGACGTGTGCTCTTCCGATCTTCCACTGTCATTGAAATTCATGCA | 2 |
| 103 | APC | 103F | 205 | ACACTCTTTCCCTACACGACGCTCTTCCGATCTCAGACTGCAGGGTTCTAGTTTATC | 103R | 206 | GTGACTGGAGTTCAGACGTGTGCTCTTCCGATCTCCCACTCATGTTTAGCAGATGTAC | 5 |
| 104 | FGFR2 | 104F | 207 | ACACTCTTTCCCTACACGACGCTCTTCCGATCTCAGTCCGGCTTGGAGGAT | 104R | 208 | GTGACTGGAGTTCAGACGTGTGCTCTTCCGATCTGGAGTGGGGATGGGAGAA | 10 |
| 105 | PTEN | 105F | 209 | ACACTCTTTCCCTACACGACGCTCTTCCGATCTACCACAGCTAGAACTTATCAAACC | 105R | 210 | GTGACTGGAGTTCAGACGTGTGCTCTTCCGATCTTGTGCATATTTATTACATCGGGGC | 10 |
| 106 | RET | 106F | 211 | ACACTCTTTCCCTACACGACGCTCTTCCGATCTGGCTATGGCACCTGCAAC | 106R | 212 | GTGACTGGAGTTCAGACGTGTGCTCTTCCGATCTCAGCCCCACAGAGGTCTC | 10 |
| 107 | ERBB4 | 107F | 213 | ACACTCTTTCCCTACACGACGCTCTTCCGATCTTTGCAGTCTTACATTTGACCATGA | 107R | 214 | GTGACTGGAGTTCAGACGTGTGCTCTTCCGATCTTTTTCCTCCAAAGGTCATCAGTTC | 2 |
| 108 | CTNNB1 | 108F | 215 | ACACTCTTTCCCTACACGACGCTCTTCCGATCTTAG | 108R | 216 | GTGACTGGAGTTCAGACGTGTGCTCTTCCGATCTGT | 3 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| | | | | CTGATTTGATGGAGTTGGAC | | | AAAGGCAATCCTGAGGAAGAG | |
| 109 | HNF1A | 109F | 217 | ACACTCTTTCCCTACACGACGCTCTTCCGATCTCTGGGCTCCAACCTCGTC | 109R | 218 | GTGACTGGAGTTCAGACGTGTGCTCTTCCGATCTCACAAGCTGGCCATGGAC | 12 |
| 110 | PDGFRA | 110F | 219 | ACACTCTTTCCCTACACGACGCTCTTCCGATCTTTGGTAATTCACCAGTTACCTGTC | 110R | 220 | GTGACTGGAGTTCAGACGTGTGCTCTTCCGATCTGCCTTATGACTCAAGATGGGAGTT | 4 |
| 111 | STK11 | 111F | 221 | ACACTCTTTCCCTACACGACGCTCTTCCGATCTGTGGGTATGGACACGTTCATC | 111R | 222 | GTGACTGGAGTTCAGACGTGTGCTCTTCCGATCTGCAAGGTGAAGGAGGTGC | 19 |
| 112 | ATM | 112F | 223 | ACACTCTTTCCCTACACGACGCTCTTCCGATCTGCTGTTCCTCAGTTTGTCACTAAA | 112R | 224 | GTGACTGGAGTTCAGACGTGTGCTCTTCCGATCTAAGGTAATTTGCAATTAACTCTTGATT | 11 |
| 113 | KDR | 113F | 225 | ACACTCTTTCCCTACACGACGCTCTTCCGATCTAACAACACTTGAAAATCTGAGCAG | 113R | 226 | GTGACTGGAGTTCAGACGTGTGCTCTTCCGATCTGGTTTGCACTCCAATCTCTATCAG | 4 |
| 114 | ERBB2 | 114F | 227 | ACACTCTTTCCCTACACGACGCTCTTCCGATCTAATTCCAGTGGCCATCAAAGT | 114R | 228 | GTGACTGGAGTTCAGACGTGTGCTCTTCCGATCTCACCCTCTCCTGCTAGGA | 17 |
| 115 | FBXW7 | 115F | 229 | ACACTCTTTCCCTACACGACGCTCTTCCGATCTACCYTGCAATGTTTGTAAACACTG | 115R | 230 | GTGACTGGAGTTCAGACGTGTGCTCTTCCGATCTGTGTGAATGCAATTCCCTGTC | 4 |
| 116 | SMAD4 | 116F | 231 | ACACTCTTTCCCTACACGACGCTCTTCCGATCTTCTGATGTCTTCCAAATCTTTTCT | 116R | 232 | GTGACTGGAGTTCAGACGTGTGCTCTTCCGATCTAAATTCACTTACACCCGGGCC | 18 |
| 117 | SMAD4 | 117F | 233 | ACACTCTTTCCCTACACGACGCTCTTCCGATCTTTTGATTTGCGTCAGTGTCAT | 117R | 234 | GTGACTGGAGTTCAGACGTGTGCTCTTCCGATCTGTAGGTGGAATAGCTCCAGC | 18 |
| 118 | EGFR | 118F | 235 | ACACTCTTTCCCTACACGACGCTCTTCCGATCTTTAACGTCTTCCTTCTCTCTCTGT | 118R | 236 | GTGACTGGAGTTCAGACGTGTGCTCTTCCGATCTTGAGTTTCTGCTTTGCTGTGTG | 7 |
| 119 | JAK3 | 119F | 237 | ACACTCTTTCCCTACACGACGCTCTTCCGATCTCTCACTGTCTCCAGCCATG | 119R | 238 | GTGACTGGAGTTCAGACGTGTGCTCTTCCGATCTCAAATTTTGTGCTCACAGACCT | 19 |
| 120 | IDH1 | 120F | 239 | ACACTCTTTCCCTACACGACGCTCTTCCGATCTTGCCAACATGACTTACTTGATCC | 120R | 240 | GTGACTGGAGTTCAGACGTGTGCTCTTCCGATCTCAGAATATTTCGTATGGTGCCAT | 2 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| 121 | APC | 121F | 241 | ACACTCTTTCCC TACACGACGCTC TTCCGATCTATG CCTCCAGTTCAG GAAAAT | 121R | 242 | GTGACTGGAGT TCAGACGTGTGC TCTTCCGATCTTT ATTTCTGCCATG CCAACA | 5 |
| 122 | FGFR2 | 122F | 243 | ACACTCTTTCCC TACACGACGCTC TTCCGATCTAAG TCCTCACCTTGA GAACC | 122R | 244 | GTGACTGGAGT TCAGACGTGTGC TCTTCCGATCTG GGCTGGGCATC ACTGTA | 10 |
| 123 | PTEN | 123F | 245 | ACACTCTTTCCC TACACGACGCTC TTCCGATCTAGG ACCAGAGGAAA CCTCAG | 123R | 246 | GTGACTGGAGT TCAGACGTGTGC TCTTCCGATCTA AATGATCTTGAC AAAGCAAATAAA GAC | 10 |
| 124 | SMAD4 | 124F | 247 | ACACTCTTTCCC TACACGACGCTC TTCCGATCTGTG ATCTATGCCCGTC TCTGG | 124R | 248 | GTGACTGGAGT TCAGACGTGTGC TCTTCCGATCTG AGTTGTATCACC TGGAATTGGTA | 18 |
| 125 | APC | 125F | 249 | ACACTCTTTCCC TACACGACGCTC TTCCGATCTACT GAGAGCACTGAT GATAAACAC | 125R | 250 | GTGACTGGAGT TCAGACGTGTGC TCTTCCGATCTA AATGTAAGCCAG TCTTTGTGTCA | 5 |
| 126 | TP53 | 126F | 251 | ACACTCTTTCCC TACACGACGCTC TTCCGATCTTTG TCCTGCTTGCTT ACCTC | 126R | 252 | GTGACTGGAGT TCAGACGTGTGC TCTTCCGATCTA CTACTCAGGATA GGAAAAGAGAA | 17 |
| 127 | ERBB4 | 127F | 253 | ACACTCTTTCCC TACACGACGCTC TTCCGATCTTGT GGATAACACATA CCAGGTGA | 127R | 254 | GTGACTGGAGT TCAGACGTGTGC TCTTCCGATCTCT GGACATTTTTCC ACACAGTTTG | 2 |
| 128 | RB1 | 128F | 255 | ACACTCTTTCCC TACACGACGCTC TTCCGATCTGTG ATTTCTAAAATA GCAGGCTCTTAT | 128R | 256 | GTGACTGGAGT TCAGACGTGTGC TCTTCCGATCTA AAATTTCAgccgg gcgc | 13 |
| 129 | ATM | 129F | 257 | ACACTCTTTCCC TACACGACGCTC TTCCGATCTTGC TTAATTATTCTGA AGGGCCG | 129R | 258 | GTGACTGGAGT TCAGACGTGTGC TCTTCCGATCTC AGGTCTTCCAGA TGTGTAATACATT | 11 |
| 130 | HRAS | 130F | 259 | ACACTCTTTCCC TACACGACGCTC TTCCGATCTCGG TGCGCATGTACT GGT | 130R | 260 | GTGACTGGAGT TCAGACGTGTGC TCTTCCGATCTTC CAACAGGCACG TCTCC | 11 |
| 131 | PTPN11 | 131F | 261 | ACACTCTTTCCC TACACGACGCTC TTCCGATCTTCTT CATGATGTTTCCT TCGTAGG | 131R | 262 | GTGACTGGAGT TCAGACGTGTGC TCTTCCGATCTAT TGAAACACTACA GCGCAGG | 12 |
| 132 | SMO | 132F | 263 | ACACTCTTTCCC TACACGACGCTC TTCCGATCTCTC CAATGAGACTCT GTCCTGC | 132R | 264 | GTGACTGGAGT TCAGACGTGTGC TCTTCCGATCTC GGGCAAGACCT CCTACTT | 7 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| 133 | KIT | 133F | 265 | ACACTCTTTCCC TACACGACGCTC TTCCGATCTTCTC AACCATCTGTGA GTCCA | 133R | 266 | GTGACTGGAGT TCAGACGTGTGC TCTTCCGATCTT GGACTTTTGAGA TCCTGGATGAA | 4 |
| 134 | ATM | 134F | 267 | ACACTCTTTCCC TACACGACGCTC TTCCGATCTCAG CTGTTACCTGTTT GAAAAACATTT | 134R | 268 | GTGACTGGAGT TCAGACGTGTGC TCTTCCGATCTA GATCCAATGCTG GCCTA | 11 |
| 135 | EGFR | 135F | 269 | ACACTCTTTCCC TACACGACGCTC TTCCGATCTCCA CTACATTGACGG CCC | 135R | 270 | GTGACTGGAGT TCAGACGTGTGC TCTTCCGATCTG TGGAAAGTGAA GGAGAACAGAA C | 7 |
| 136 | NOTCH1 | 136F | 271 | ACACTCTTTCCC TACACGACGCTC TTCCGATCTGAC CAGCGAGGATG GCAG | 136R | 272 | GTGACTGGAGT TCAGACGTGTGC TCTTCCGATCTC ACTCAGGAAGCT CCGGC | 9 |
| 137 | FGFR3 | 137F | 273 | ACACTCTTTCCC TACACGACGCTC TTCCGATCTCAA TGTGCTGGTGAC CGAG | 137R | 274 | GTGACTGGAGT TCAGACGTGTGC TCTTCCGATCTG GGTCATGCCAGT AGGACG | 4 |
| 138 | FGFR3 | 138F | 275 | ACACTCTTTCCC TACACGACGCTC TTCCGATCTGGG ACGACTCCGTGT TTG | 138R | 276 | GTGACTGGAGT TCAGACGTGTGC TCTTCCGATCTG TGAGGGGTCCCT AGCAG | 4 |
| 139 | KDR | 139F | 277 | ACACTCTTTCCC TACACGACGCTC TTCCGATCTCCC ACTGGATGCTGC ACA | 139R | 278 | GTGACTGGAGT TCAGACGTGTGC TCTTCCGATCTG TTGACTGAACTT CCAAAGCAC | 4 |
| 140 | ABL1 | 140F | 279 | ACACTCTTTCCC TACACGACGCTC TTCCGATCTGTC TTGTTGGCAGG GGTC | 140R | 280 | GTGACTGGAGT TCAGACGTGTGC TCTTCCGATCTTC ATCCACAGGTAG GGGC | 9 |
| 141 | APC | 141F | 281 | ACACTCTTTCCC TACACGACGCTC TTCCGATCTCATC AGCTGAAGATG AAATAGGATGTA A | 141R | 282 | GTGACTGGAGT TCAGACGTGTGC TCTTCCGATCTA GCACCCTAGAAC CAAATCC | 5 |
| 142 | TP53 | 142F | 283 | ACACTCTTTCCC TACACGACGCTC TTCCGATCTSCC AGTTGCAAACCA GAC | 142R | 284 | GTGACTGGAGT TCAGACGTGTGC TCTTCCGATCTAT CAGTGAGGAATC AGAGGC | 17 |
| 143 | FGFR3 | 143F | 285 | ACACTCTTTCCC TACACGACGCTC TTCCGATCTGTG TCTGTCCTGGGA GTCT | 143R | 286 | GTGACTGGAGT TCAGACGTGTGC TCTTCCGATCTCA TCCCTGTGGAGG AGCT | 4 |
| 144 | KIT | 144F | 287 | ACACTCTTTCCC TACACGACGCTC TTCCGATCTCTG TTGTGCTTCTATT ACAGGCTC | 144R | 288 | GTGACTGGAGT TCAGACGTGTGC TCTTCCGATCTA ATGATCCTTGCC AAAGACAACT | 4 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| 145 | KDR | 145F | 289 | ACACTCTTTCCC TACACGACGCTC TTCCGATCTCTG GCTTTGAATCATT AGCGTTAC | 145R | 290 | GTGACTGGAGT TCAGACGTGTGC TCTTCCGATCTC GGACTCAGAAC CACATCATAAAT | 4 |
| 146 | ERBB4 | 146F | 291 | ACACTCTTTCCC TACACGACGCTC TTCCGATCTAAG GTTTACACATTTT AATCCCATTTT | 146R | 292 | GTGACTGGAGT TCAGACGTGTGC TCTTCCGATCTA CATTCAGCAAAC AAGCTCAAAAC | 2 |
| 147 | ATM | 147F | 293 | ACACTCTTTCCC TACACGACGCTC TTCCGATCTATTA GGTGGACCACA CAGGA | 147R | 294 | GTGACTGGAGT TCAGACGTGTGC TCTTCCGATCTTA AGGTGAGCCTTC CCTTC | 11 |
| 148 | RET | 148F | 295 | ACACTCTTTCCC TACACGACGCTC TTCCGATCTACT CGTGCTATTTTTC CTCACAG | 148R | 296 | GTGACTGGAGT TCAGACGTGTGC TCTTCCGATCTTA CGTGAAGAGGA GCCAG | 10 |
| 149 | IDH2 | 149F | 297 | ACACTCTTTCCC TACACGACGCTC TTCCGATCTGCC TACCTGGTCGCC ATG | 149R | 298 | GTGACTGGAGT TCAGACGTGTGC TCTTCCGATCTCA TTGGGACTTTTC CACATCTTCT | 15 |
| 150 | MET | 150F | 299 | ACACTCTTTCCC TACACGACGCTC TTCCGATCTGAC ATGTCTTTCCCC ACAATCATA | 150R | 300 | GTGACTGGAGT TCAGACGTGTGC TCTTCCGATCTCT TTCATCTGTAAA GGACCGGTTC | 7 |
| 151 | SMARCB1 | 151F | 301 | ACACTCTTTCCC TACACGACGCTC TTCCGATCTTACT CATAGGTGGGA AACTACCTC | 151R | 302 | GTGACTGGAGT TCAGACGTGTGC TCTTCCGATCTC CTAACACTAAGG GTGCGT | 22 |
| 152 | SRC | 152F | 303 | ACACTCTTTCCC TACACGACGCTC TTCCGATCTCTTC CTGGAGGACTAC TTCACG | 152R | 304 | GTGACTGGAGT TCAGACGTGTGC TCTTCCGATCTCT CTGCCTGCCTGC TGTT | 20 |
| 153 | ATM | 153F | 305 | ACACTCTTTCCC TACACGACGCTC TTCCGATCTATCT AGGATCCAAATT TTAGAAGTCAAG | 153R | 306 | GTGACTGGAGT TCAGACGTGTGC TCTTCCGATCTTC ATCTTGTACTGG AGAAAATTCTTG TG | 11 |
| 154 | NOTCH1 | 154F | 307 | ACACTCTTTCCC TACACGACGCTC TTCCGATCTCAC TGCCGGTTGTCA ATCTC | 154R | 308 | GTGACTGGAGT TCAGACGTGTGC TCTTCCGATCTT GACGCCACAGTC AGGAC | 9 |
| 155 | KIT | 155F | 309 | ACACTCTTTCCC TACACGACGCTC TTCCGATCTTCA CCTTCTTTCTAAC CTTTTCTTATGT | 155R | 310 | GTGACTGGAGT TCAGACGTGTGC TCTTCCGATCTA AACGTGATTCAT TTATTTGTTCAAA GC | 4 |
| 156 | KDR | 156F | 311 | ACACTCTTTCCC TACACGACGCTC TTCCGATCTGAT GCTCACTGTGTG TTGCT | 156R | 312 | GTGACTGGAGT TCAGACGTGTGC TCTTCCGATCTA ATAATTGGGGTC CCTCCCT | 4 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| 157 | RET | 157F | 313 | ACACTCTTTCCC TACACGACGCTC TTCCGATCTCGC AGCCTGTACCCA GTG | 157R | 314 | GTGACTGGAGT TCAGACGTGTGC TCTTCCGATCTT GCTACCACAAGT TTGCCC | 10 |
| 158 | PTEN | 158F | 315 | ACACTCTTTCCC TACACGACGCTC TTCCGATCTGCT ACGACCCAGTTA CCATAGC | 158R | 316 | GTGACTGGAGT TCAGACGTGTGC TCTTCCGATCTA GCTACCTGTTAA AGAATCATCTGG A | 10 |
| 159 | GNAQ | 159F | 317 | ACACTCTTTCCC TACACGACGCTC TTCCGATCTGAG GTGACATTTTCA AAGCAGTG | 159R | 318 | GTGACTGGAGT TCAGACGTGTGC TCTTCCGATCTA AATATAGCACTA CTTACAAACTTA GGG | 9 |
| 160 | ERBB4 | 160F | 319 | ACACTCTTTCCC TACACGACGCTC TTCCGATCTAAA GTGGCTAAAGTT GATCTGATTGT | 160R | 320 | GTGACTGGAGT TCAGACGTGTGC TCTTCCGATCTG TCCTGAGCAGC MTCCAG | 2 |
| 161 | JAK2 | 161F | 321 | ACACTCTTTCCC TACACGACGCTC TTCCGATCTCCTT AGTCTTTCTTTG AAGCAGCA | 161R | 322 | GTGACTGGAGT TCAGACGTGTGC TCTTCCGATCTC CTTTCTCAGAGC ATCTGTTTTG | 9 |
| 162 | ERBB4 | 162F | 323 | ACACTCTTTCCC TACACGACGCTC TTCCGATCTATA ACTCATTCATCG CCACATAGG | 162R | 324 | GTGACTGGAGT TCAGACGTGTGC TCTTCCGATCTT GAATGGTGTCTG CATAACAAAGG | 2 |
| 163 | EGFR | 163F | 325 | ACACTCTTTCCC TACACGACGCTC TTCCGATCTGTC TCTGTGTTCTTGT CCCC | 163R | 326 | GTGACTGGAGT TCAGACGTGTGC TCTTCCGATCTT GTATAAGGTAAG GTCCCTGG | 7 |
| 164 | CSF1R | 164F | 327 | ACACTCTTTCCC TACACGACGCTC TTCCGATCTCATC CATGGAGGAGTT GAAGTTT | 164R | 328 | GTGACTGGAGT TCAGACGTGTGC TCTTCCGATCTC AGGTGCTCACTA GAGCTC | 5 |
| 165 | VHL | 165F | 329 | ACACTCTTTCCC TACACGACGCTC TTCCGATCTCTCT TGTTCGTTCCTT GTACTGAG | 165R | 330 | GTGACTGGAGT TCAGACGTGTGC TCTTCCGATCTA GGAGACTGGAC ATCGTCAG | 3 |
| 166 | PDGFRA | 166F | 331 | ACACTCTTTCCC TACACGACGCTC TTCCGATCTAGG CYCCATTTACATC ATCA | 166R | 332 | GTGACTGGAGT TCAGACGTGTGC TCTTCCGATCTC ACCCAGAGAAG CCAAAGAAAG | 4 |
| 167 | ATM | 167F | 333 | ACACTCTTTCCC TACACGACGCTC TTCCGATCTATA GGAAGTAGAGG AAAGTATTCTTC AG | 167R | 334 | GTGACTGGAGT TCAGACGTGTGC TCTTCCGATCTC CAGGTACAGTAA GTAGGTCATGT | 11 |
| 168 | SMARCB1 | 168F | 335 | ACACTCTTTCCC TACACGACGCTC TTCCGATCTCAC CCCTACACTTGG CTG | 168R | 336 | GTGACTGGAGT TCAGACGTGTGC TCTTCCGATCTCT GGTAACCAGCCC ATCAG | 22 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| 169 | STK11 | 169F | 337 | ACACTCTTTCCC TACACGACGCTC TTCCGATCTCTC CCCTCGAAATGA AGCTA | 169R | 338 | GTGACTGGAGT TCAGACGTGTGC TCTTCCGATCTG GGAGCCTCATCC CTCTG | 19 |
| 170 | HRAS | 170F | 339 | ACACTCTTTCCC TACACGACGCTC TTCCGATCTCCA GGCTCACCTCTA TAGTGG | 170R | 340 | GTGACTGGAGT TCAGACGTGTGC TCTTCCGATCTC ACCACCAGCTTA TATTCCGT | 11 |
| 171 | ERBB2 | 171F | 341 | ACACTCTTTCCC TACACGACGCTC TTCCGATCTCCT CTCAGCGTACCC TTGT | 171R | 342 | GTGACTGGAGT TCAGACGTGTGC TCTTCCGATCTG GTGCAGCTGGT GACACA | 17 |
| 172 | EZH2 | 172F | 343 | ACACTCTTTCCC TACACGACGCTC TTCCGATCTATAC AATGCCACCTGA ATACAGG | 172R | 344 | GTGACTGGAGT TCAGACGTGTGC TCTTCCGATCTG TGCCAGCAATAG ATGCTAGA | 7 |
| 173 | FBXW7 | 173F | 345 | ACACTCTTTCCC TACACGACGCTC TTCCGATCTCTC CTGCCATCATATT GAACACAG | 173R | 346 | GTGACTGGAGT TCAGACGTGTGC TCTTCCGATCTT GCAGAGGGAGA AACAGAAAAAC | 4 |
| 174 | KIT | 174F | 347 | ACACTCTTTCCC TACACGACGCTC TTCCGATCTGTA GAGCATGACCCA TGAGTG | 174R | 348 | GTGACTGGAGT TCAGACGTGTGC TCTTCCGATCTAT GGACATGAAAC CTGGAGTT | 4 |
| 175 | RB1 | 175F | 349 | ACACTCTTTCCC TACACGACGCTC TTCCGATCTGTT CTTCCTCAGACA TTCAAACGT | 175R | 350 | GTGACTGGAGT TCAGACGTGTGC TCTTCCGATCTC CAGGGTAGGTC AAAAGTATCCTT | 13 |
| 176 | EGFR | 176F | 351 | ACACTCTTTCCC TACACGACGCTC TTCCGATCTTACC AGATGGATGTGA ACCCC | 176R | 352 | GTGACTGGAGT TCAGACGTGTGC TCTTCCGATCTG GAGTATCCCATC TTGGAGAGTC | 7 |
| 177 | ERBB4 | 177F | 353 | ACACTCTTTCCC TACACGACGCTC TTCCGATCTTG CCATTTTGGATAT ATTCCTTACCT | 177R | 354 | GTGACTGGAGT TCAGACGTGTGC TCTTCCGATCTTT GTCCCACGAATA ATGCGTAAAT | 2 |
| 178 | CDH1 | 178F | 355 | ACACTCTTTCCC TACACGACGCTC TTCCGATCTACT TGGTTGTGTCGA TCTCTCT | 178R | 356 | GTGACTGGAGT TCAGACGTGTGC TCTTCCGATCTC TTCAATCCCACC ACGGTAAT | 16 |
| 179 | STK11 | 179F | 357 | ACACTCTTTCCC TACACGACGCTC TTCCGATCTAGA CACCAAGGACC GGTG | 179R | 358 | GTGACTGGAGT TCAGACGTGTGC TCTTCCGATCTA CATCGAGGATGA CATCATCTACA | 19 |
| 180 | ABL1 | 180F | 359 | ACACTCTTTCCC TACACGACGCTC TTCCGATCTTCA AGTACTTACCCA CTGAAAAGC | 180R | 360 | GTGACTGGAGT TCAGACGTGTGC TCTTCCGATCTT GCAGCTCCTTGG TGAGTAA | 9 |
| 181 | PTEN | 181F | 361 | ACACTCTTTCCC TACACGACGCTC | 181R | 362 | GTGACTGGAGT TCAGACGTGTGC | 10 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| | | | | TTCCGATCTAGC TCATTTTGTTAA TGGTGGCT | | | TCTTCCGATCTT GCTTGCAAATAT CTTCTAAAACAA CTA | |
| 182 | ATM | 182F | 363 | ACACTCTTTCCC TACACGACGCTC TTCCGATCTTGAT AAATKAGCAGTC AGCAGAA | 182R | 364 | GTGACTGGAGT TCAGACGTGTGC TCTTCCGATCTCA TGGAATGTTGTT TGCCTACC | 11 |
| 183 | RB1 | 183F | 365 | ACACTCTTTCCC TACACGACGCTC TTCCGATCTTTTC TTATTCCCACAGT GTATCGG | 183R | 366 | GTGACTGGAGT TCAGACGTGTGC TCTTCCGATCTC CTGCAGAATGAG TATGAACTCAT | 13 |
| 184 | KDR | 184F | 367 | ACACTCTTTCCC TACACGACGCTC TTCCGATCTAGC TTTAAAAGTTCT GCTTCCTCA | 184R | 368 | GTGACTGGAGT TCAGACGTGTGC TCTTCCGATCTC ACCATTCCACTG CAGAAGAAAT | 4 |
| 185 | EGFR | 185F | 369 | ACACTCTTTCCC TACACGACGCTC TTCCGATCTTCC TCAAAAGAGAA ATCACGCAT | 185R | 370 | GTGACTGGAGT TCAGACGTGTGC TCTTCCGATCTA AATATGTACTACG AAAATTCCTATG CC | 7 |
| 186 | NOTCH1 | 186F | 371 | ACACTCTTTCCC TACACGACGCTC TTCCGATCTAAG ATCATCTGCTGG CCGT | 186R | 372 | GTGACTGGAGT TCAGACGTGTGC TCTTCCGATCTC CAGCCTCTCGGG TACAT | 9 |
| 187 | TP53 | 187F | 373 | ACACTCTTTCCC TACACGACGCTC TTCCGATCTAGA GGCAAGCAGAG GCTG | 187R | 374 | GTGACTGGAGT TCAGACGTGTGC TCTTCCGATCTA CCTAGGAGATAA CACAGGCC | 17 |
| 188 | APC | 188F | 375 | ACACTCTTTCCC TACACGACGCTC TTCCGATCTAGA GAACGCGGAAT TGGTCT | 188R | 376 | GTGACTGGAGT TCAGACGTGTGC TCTTCCGATCTA GCCATTCATACCT CTCAGGAA | 5 |
| 189 | SMAD4 | 189F | 377 | ACACTCTTTCCC TACACGACGCTC TTCCGATCTCTTT TTYCTTCCTAAG GTTGCACA | 189R | 378 | GTGACTGGAGT TCAGACGTGTGC TCTTCCGATCTC GTGCACCTGGA GATGCT | 18 |
| 190 | SMARCB1 | 190F | 379 | ACACTCTTTCCC TACACGACGCTC TTCCGATCTTCTT GTATCTCCTCAG GGAACAG | 190R | 380 | GTGACTGGAGT TCAGACGTGTGC TCTTCCGATCTA GACAAGAAGAG AACCTTCCCC | 22 |
| 191 | ERBB2 | 191F | 381 | ACACTCTTTCCC TACACGACGCTC TTCCGATCTTACA TGGGTGCTTCCC ATTC | 191R | 382 | GTGACTGGAGT TCAGACGTGTGC TCTTCCGATCTG GGGCAAGGTTA GGTGAAG | 17 |
| 192 | NRAS | 192F | 383 | ACACTCTTTCCC TACACGACGCTC TTCCGATCTTAC AAAGTGGTTCTG GATTAGCTG | 192R | 384 | GTGACTGGAGT TCAGACGTGTGC TCTTCCGATCTG CGAGCCACATCT ACAGTACTTTA | 1 |
| 193 | FGFR3 | 193F | 385 | ACACTCTTTCCC TACACGACGCTC TTCCGATCTCAT | 193R | 386 | GTGACTGGAGT TCAGACGTGTGC TCTTCCGATCTC | 4 |

TABLE 3-continued

Amplicons and corresponding primer pairs

| Assay_ID | Target_Gene | Forward_Primer_ID | SEQ. ID NO: | Forward_Primer | Reverse_Primer_ID | SEQ. ID NO: | Reverse_Primer | Chr |
|---|---|---|---|---|---|---|---|---|
| | | | | GTCTTTGCAGCCGAGG | | | CAAGAAAGGCCTGGGCT | |
| 194 | KIT | 194F | 387 | ACACTCTTTCCCTACACGACGCTCTTCCGATCTGGTGATCTATTTTCCCTTTCTCCC | 194R | 388 | GTGACTGGAGTTCAGACGTGTGCTCTTCCGATCTAGAAACAGGCTGAGTTTTGGTC | 4 |
| 195 | KDR | 195F | 389 | ACACTCTTTCCCTACACGACGCTCTTCCGATCTTAGACAAGGTCTTCCTTCCACTT | 195R | 390 | GTGACTGGAGTTCAGACGTGTGCTCTTCCGATCTTCCTCCTCCATACAGGAAACAG | 4 |
| 196 | PIK3CA | 196F | 391 | ACACTCTTTCCCTACACGACGCTCTTCCGATCTTTCTCAATGATGCTTGGCTC | 196R | 392 | GTGACTGGAGTTCAGACGTGTGCTCTTCCGATCTTGGCTGGACAACAAAAATGGA | 3 |

Amplification of the target nucleic acid regions. A pool of 196 amplicon primer pairs in a concentration of 50 nM for each primer were added to a single PCR tube, 50 ng of human genomic DNA (GenBank No.: NA12878) and 10 µL of amplification reaction mixture which contains 3% glycerol, 0.2 nM dNTPs, 50 nM pyrophosphate and 2 units of KlenTaq-S DNA polymerase to a final volume of 20 µL with DNase/RNase free water. The PCR tube was put on a thermal cycler and run the following temperature profile to get the amplified amplicon library. An initial holding stage was carried out at 98° C. for 2 minutes, followed by 98° C. 15 seconds, 55° C. 8 minutes, for 17 cycles. After cycling, the reaction was held at 72° C. for 5 minutes and then 4° C. until proceeding to the beads purification step to remove excess primers. The tube cap was carefully removed and 24 µL of Agencourt AMPure® XP Reagent (Beckman Coulter, CA) was added to the reaction mixture to purify the DNA. The reaction mixture was vortex mixed and incubated for 5 minutes at room temperature. The tube was placed in a magnetic rack and incubated until solution clears. The supernatant was carefully remove and discarded without disturbing the pellet, then 150 µL of freshly prepared 70% ethanol was added. The reaction mixture was vortexed to mix well, pulsed spin, and incubated until solution clears. The supernatant was carefully removed and discarded without disturbing the pellet. Another portion of 150 µL of freshly prepared 70% ethanol was added. The reaction mixture was vortexed to mix well, pulsed spin, and incubated until solution clears. The supernatant was carefully removed and discarded without disturbing the pellet. Leave the tube open to evaporate for about 2 minutes. The remaining bead pellet in the tube contains the purified DNA.

Construction of library. Then 50 µL of Platinum® PCR SuperMix High Fidelity DNA Polymerase (Thermo Fisher, Cat #12532016) and 2 µL of Library Amplification Barcoded Primer Mix (10 µM concentration for each primer was added to bead pellet). The sequence of each primer is shown in Table 4. The PCR tube was put on a thermal cycler and run the following temperature profile to get the amplified amplicon library. An initial holding stage was carried out at 98° C. for 2 minutes, followed by 98° C. 15 seconds, 60° C. 1 minute, for 5 cycles. After cycling, the reaction was held at 72° C. for 5 minutes and then kept at 4° C. until purification. The tube cap was carefully removed and 44 µL of Agencourt AMPure® XP Reagent (Beckman Coulter, CA) was added to the reaction mix for purifying the product. The reaction was vortex mixed and incubated for 5 minutes at room temperature. The tube was placed in a magnetic rack and incubated until solution clears. The supernatant was carefully removed and discarded without disturbing the pellet. Then 150 µL of freshly prepared 70% ethanol was added to the pellet; the reaction mixture was vortexed to mix well, pulsed spin, and incubated until solution clears; the supernatant was carefully removed and discarded without disturbing the pellet; the foregoing wash step was repeated for another time. After the wash, leave the tube open to evaporate for about 2 minutes. Then 50 µL of low TE buffer was added and the solution was vortexed thoroughly. The tube was placed in the magnet until solution clears. The supernatant containing library was collected to a separate clean tube. The library was quantified using Qubit® 2.0 Fluorometer (Life Technologies, CA) and Bioanalyzer (Agilent Technologies, CA) according to manufacturer protocol.

TABLE 4

Primers for construction of library

| Primer Name | SEQ ID NO: | Primer Sequence |
|---|---|---|
| R2TruSeqBC001 | 393 | CAAGCAGAAGACGGCATACGAGATcgcgactgaaGTGACTGGAGTTCAGACGTGT |
| R2TruSeqBC002 | 394 | CAAGCAGAAGACGGCATACGAGATagcatcgataGTGACTGGAGTTCAGACGTGT |

TABLE 4-continued

Primers for construction of library

| Primer Name | SEQ ID NO: | Primer Sequence |
|---|---|---|
| R2TruSeqBC003 | 395 | CAAGCAGAAGACGGCATACGAGATcgacacatggGT GACTGGAGTTCAGACGTGT |
| R2TruSeqBC004 | 396 | CAAGCAGAAGACGGCATACGAGATcgactacgcaGT GACTGGAGTTCAGACGTGT |
| R2TruSeqBC005 | 397 | CAAGCAGAAGACGGCATACGAGATcactgctgagGTG ACTGGAGTTCAGACGTGT |
| R2TruSeqBC006 | 398 | CAAGCAGAAGACGGCATACGAGATtcgctgtacaGTG ACTGGAGTTCAGACGTGT |
| R2TruSeqBC007 | 399 | CAAGCAGAAGACGGCATACGAGATcgctgcagtaGTG ACTGGAGTTCAGACGTGT |
| R2TruSeqBC008 | 400 | CAAGCAGAAGACGGCATACGAGATagacttgcagGTG ACTGGAGTTCAGACGTGT |
| R1_TruSeq_primer | 401 | AATGATACGGCGACCACCGAGATCTACACTCTTT CCCTACACGAC |

The library was sequenced on Illumina MiSeq sequencer according to manufacturer's procedure.

Data Processing

Sequencing reads were aligned to GRC37/hg19 reference genome downloaded from web of ucsc genome browser (hgdownload.soe.ucsc.edu/goldenPath/hg19/bigZips/) using the software of bowtie2 (downloaded from sourceforge.net/projects/bowtie-bio/files/bowtie/1.2.1.1) with default settings. The aligned reads were further assigned to amplicons based on the match between positions of reads of R1 and R2 in genome and positions of forward and reverse primers of designed assays. The preliminary results indicated that performances of cancer hot spot panel were (1) 69.7% reads aligned to genome; (2) 95.5% reads aligned to target regions of design; (3) 98.1% of assays with amplicon read coverage within 5-fold of the mean average.

Example 2. Multiplex Enrichment of Mutant Nucleic Acid for Sequencing

Figure 12:
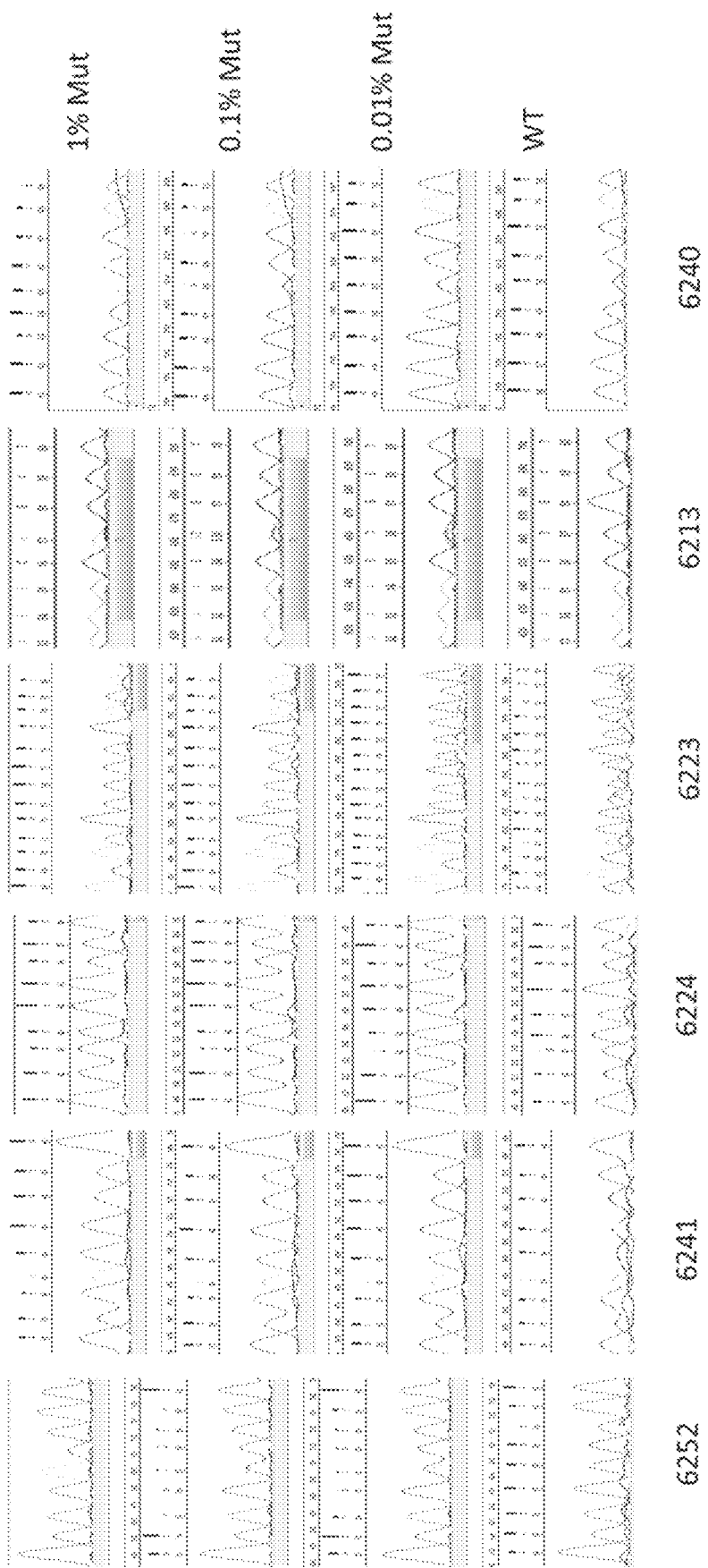
FIG. 12. Electropherogram of selectively enriched different mutant nucleic acids after multiplex PCR reaction in Example 2.

In 20 μL PCR reaction solution, two pools of 8 primer pairs (see Table 5) with each primer containing dideoxynucleotide at its 3' end in 0.5 μM concentration were added together with 2 μL of 10×PCR buffer, 3 mM MgCl$_2$, 0.2 mM dNTP, 50 nM pyrophosphate, 2 units of AmpliTaq DNA polymerase FS and 1%, 0.1% or 0.01% mutant nucleic acid (Horizon discovery, Cambridge, United Kingdomin), 30 ng of human genomic DNA (GenBank No.: NA12878). The PCR tube was loaded on a thermal cycler and run the following temperature profile: 95° C. for 2 min; 95° C. 15 seconds, 65° C. 120 seconds, for 40 cycles; hold at 4° C. 5 μL ExoSAP-IT™ solution (Affymetrix, CA) was added to the tube, and the reaction was incubated at 37° C. for 15 min, 80° C. for 10 min, held at 4° C. 2 μL of reaction solution was used to perform cycle sequencing with BigDye™ Terminator v3.1 cycle sequencing kit (Life Technologies, CA) and the resulting DNA was purified according to manufacturer protocol. The purified sample electrophoresis was carried out on ABI Prism 3730 DNA analyzer according to manufacturer recommended protocol. Electropherogram in FIG. 12 showed examples of enrichment of mutant nucleic acid (EGFR COSMIC6240 mutation, EGFR COSMIC6252 mutation, COSMIC6241 mutation, COSMIC6224 mutation, COSMIC6223 mutation and COSMIC6213 mutation from FIG. 12 from 1%, 0.1% or 0.01% (Mol/Mol) of mutant in wildtype background after amplification reaction.

TABLE 5

Primers for enrichment of mutant nucleic acid

| Pool ID | Forward Primer ID | SEQ ID NO: | Forward Primer Sequence | Reverse Primer ID | SEQ ID NO: | Reverse Primer Sequence |
|---|---|---|---|---|---|---|
| PMS001 | SMDM13CF0033 | 402 | CAGGAAACAGCTATGACCGTGGAGAAGCTCCCAACCAAGC | SMDM13MR0033 | 403 | TGTAAAACGACGGCCAGTCGAACGCACCGGAGCT |
|  | SMDM13MF0055 | 404 | TGTAAAACGACGGCCAGTGAAAGTTAAAATTCCCGTCGCTATCAAA | SMDM13CR0055 | 405 | CAGGAAACAGCTATGACCGGCCTGAGGTTCAGAGCCATG |
|  | SMDM13CF0014 | 406 | CAGGAAACAGCTATGACCGAAGCCACACTGACGTGCCTCT | SMDM13MR0014 | 407 | TGTAAAACGACGGCCAGTGGCACGTGGGGTTGTCCACGA |

TABLE 5-continued

Primers for enrichment of mutant nucleic acid

| Pool ID | Forward Primer ID | SEQ ID NO: | Forward Primer Sequence | Reverse Primer ID | SEQ ID NO: | Reverse Primer Sequence |
|---|---|---|---|---|---|---|
| | SMDM13CF0041 | 408 | CAGGAAACAGCTATGACCCAGCCAGGAACGTACTGGTGAA | SMDM13MR0041 | 409 | TGTAAAACGACGGCCAGTGCACCCAGCAGTTTGGCCC |
| PMS002 | SMDM13CF0002 | 410 | CAGGAAACAGCTATGACCGTGGAGAAGCTCCCAACCAAGC | SMDM13MR0002 | 411 | TGTAAAACGACGGCCAGTTGCCGAACGCACCGGAGCA |
| | SMDM13MF0010 | 412 | TGTAAAACGACGGCCAGTGAAAGTTAAAATTCCCGTCGCTATCAAGA | SMDM13CR0010 | 413 | CAGGAAACAGCTATGACCGGCCTGAGGTTCAGAGCCATG |
| | SMDM13MF0044 | 414 | TGTAAAACGACGGCCAGTCACCGTGCAGCTCATCAT | SMDM13CR0044 | 415 | CAGGAAACAGCTATGACCGTTGAGCAGGTACTGGGAGCCA |
| | SMDM13CF0009 | 416 | CAGGAAACAGCTATGACCCAGCCAGGAACGTACTGGTGAA | SMDM13MR0009 | 417 | TGTAAAACGACGGCCAGTCTTTCTCTTCCGCACCCAGCT |

Figure 13:
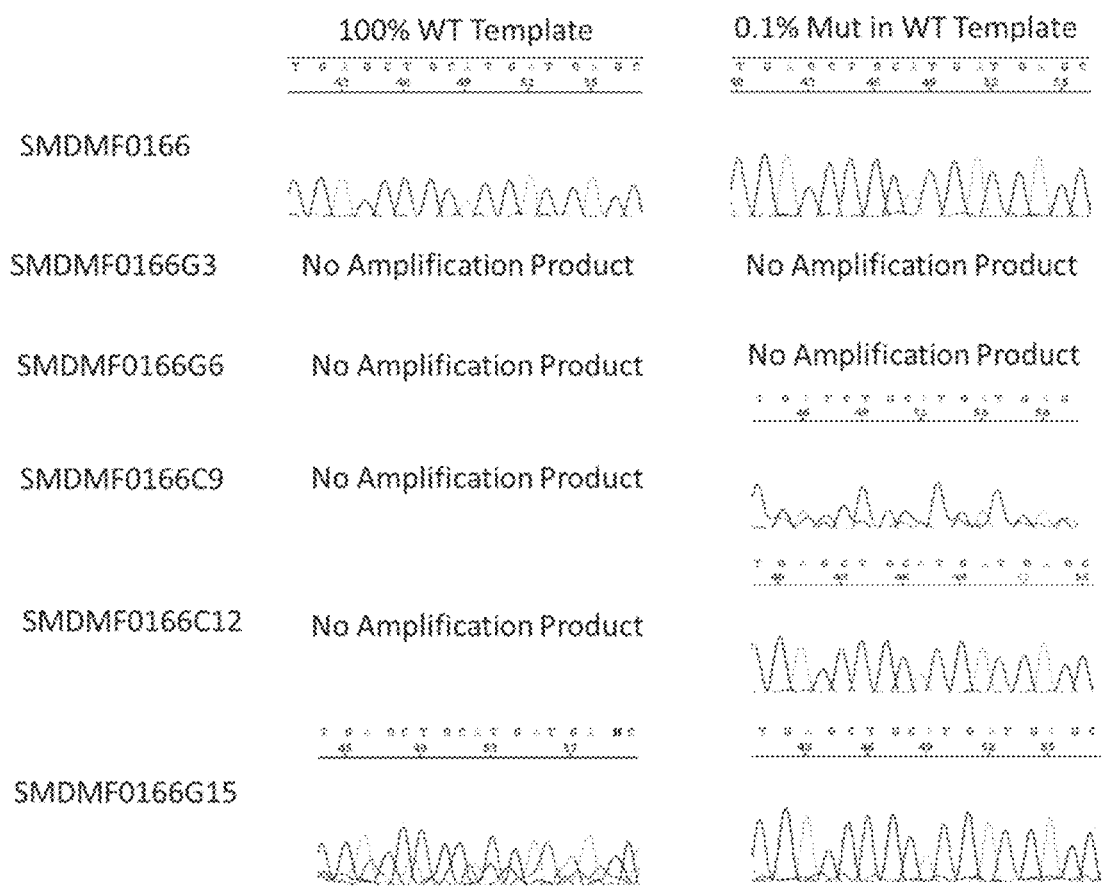
FIG. 13. Electropherogram of selectively enriched mutant nucleic acid after multiplex PCR reaction in Example 3.

Example 3. Enrichment of Mutant Nucleic Acid by Mismatched PAP Primers for Sequencing In 20 μL PCR reaction solution, a pair of primers (one primer is SMDCR0166 and the other primer is selected from one of SMDMF0166, SMDMF0166G3, SMDMF0166G6, SMDMF0166C9, SMDMF0166C12, SMDMF0166G15) (see Table 6) with each primer containing dideoxynucleotide at its 3' end in 0.5 μM concentration were added with 2 μL of 10×PCR buffer, with final concentration of 3 mM MgCl$_2$, 0.2 mM dNTP, 90 μM of pyrophosphate and 2 units of KlenTaq-S. 30 ng of 100% wild type human genomic DNA (see Table 6) or wild type human genomic DNA spiked with 0.1% mutant genomic DNA (EGFR T790M, see Table 6) was also added to the PCR reaction mixture. The PCR tube was loaded on a thermal cycler and run the following temperature profile: 95° C. for 2 min; 95° C. 15 seconds, 65° C. 120 seconds, for 40 cycles; held at 4° C. 5 μL ExoSAP-IT™ solution (Affymetrix, CA) was added to the tube, and the reaction was incubated at 37° C. for 15 min, 80° C. for 10 min, held at 4° C. 2 μL of treated reaction solution was used to perform cycle sequencing reaction with BigDye™ Terminator v3.1 cycle sequencing kit (Life Technologies, CA) and purified according to manufacturer protocol. The purified sample electrophoresis was carried out on ABI Prism 3730 DNA analyzer according to manufacturer recommended protocol. The results are shown in FIG. 13. It can be seen that the mismatched nucleotide contributes to decreasing false positive results.

TABLE 6

Primer and template sequence for EGFR T790M detection

| Primer or Template | SEQ ID NO: | Sequence |
|---|---|---|
| SMDMF0166 | 418 | CTCCACCGTGCAGCTCATCAddT |
| SMDMF0166G3 | 419 | CTCCACCGTGCAGCTCATGAddT |
| SMDMF0166G6 | 420 | CTCCACCGTGCAGCTGATCAddT |
| SMDMF0166C9 | 421 | CTCCACCGTGCAGCTCATCAddT |
| SMDMF0166C12 | 422 | CTCCACCGTGCAGCTCATCAddT |
| SMDMF0166O15 | 423 | CTCCACGGTGCAGCTCATCAddT |
| SMDCR0166 | 424 | GTTGAGCAGGTACTGGGAGCCddA |
| WT Template (3' to 5') | 425 | GAGGTGGCACGTCGAGTAGTGCGTCGAGTACGGGAAGCCGACGGAGGACCTGATACAGGC--- |
| Mut Template (3' to 5') | 426 | GAGGTGGCACGTCGAGTAGTACGTCGAGTACGGGAAGCCGACGGAGGACCTGATACAGGC--- |

Figure 14:
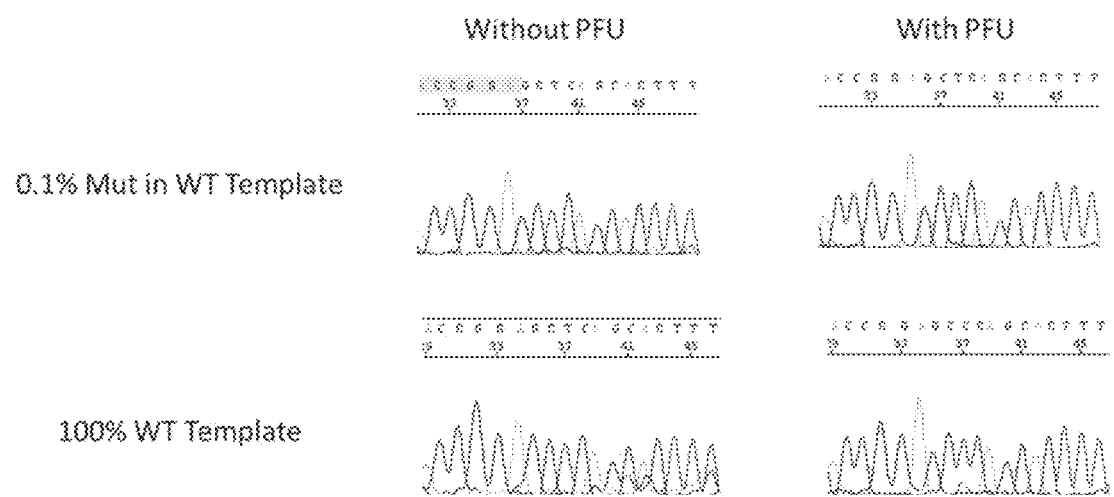
FIG. 14. Electropherogram of selectively enriched mutant nucleic acid after multiplex PCR reaction in Example 4.
Figure 15:
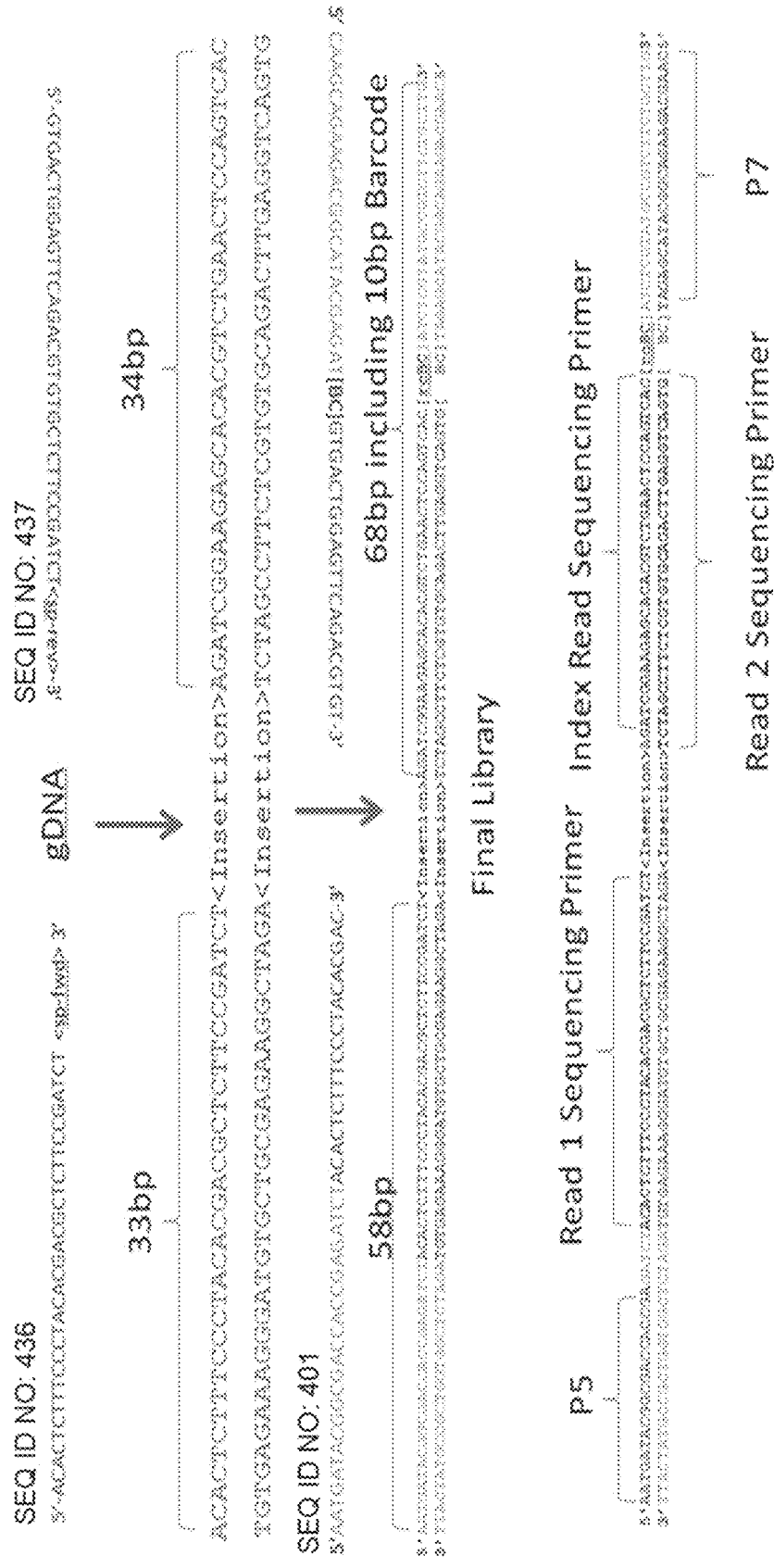
FIG. 15. The sketch of multiplex PCR and the construction of library in Example 1.

Example 4. Enrichment of Mutant Nucleic Acid by PAP Primers and Proof-Reading PFU Enzyme for Sequencing In 20 μL PCR reaction solution, forward and reverse primer pairs (see Table 7) with each primer containing dideoxynucleotide at its 3' end in 0.5 μM concentration were added with 2 μL of 10×PCR buffer, with final concentration of 3 mM $MgCl_2$, 0.2 mM dNTP, 90 μM of pyrophosphate and 2 units of KlenTaq-S with or without 2 units of Pfu DNA polymerase (Promega, Wis.) were added to the reaction mixture. Then 30 ng of 100% wild type human genomic DNA (NA12878) (see Table 7) or wild type human genomic DNA (NA12878) spiked with 0.10% mutant genomic DNA (EGFR G719S, see Table 7) was also added to the PCR reaction mixture. The PCR tube was loaded on a thermal cycler and run the following temperature profile: 95° C. for 2 min; 95° C. 15 seconds, 65° C. 120 seconds, for 40 cycles, held at V° C. 5 μL ExoSAP-IT™ solution (Affymetrix, CA) was added to the tube, and the reaction was incubated at 37° C. for 15 min, 80° C. for 10 min, held at 4° C. 2 μL of treated reaction solution was used to perform cycle sequencing with BigDye™ Terminator v3.1 cycle sequencing kit (Life Technologies, CA) and purified according to manufacturer protocol. The purified sample electrophoresis was carried out on ABI Prism 3730 DNA analyzer according to manufacturer recommended protocol. The results are shown in FIG. 14. It can be seen that the proof-reading PFU enzyme contributes to decreasing false positive results.

TABLE 7

Primer and template sequence for EGFR G719S detection

| Primer or Template | SEQ ID NO: | Sequence |
| --- | --- | --- |
| SMDMF0166 | 427 | CTCCACCGTGCAGCTCATCAddT |
| SMDMF0166G3 | 428 | CTCCACCGTGCAGCTCATGAddT |
| SMDMF0166G6 | 429 | CTCCACCGTGCAGCTGATCAddT |
| SMDMF0166C9 | 430 | CTCCACCGTGCAGCTCATCAddT |
| SMDMF0166C12 | 431 | CTCCACCGTCCAGCTCATCAddT |
| SMDMF0166O15 | 432 | CTCCACCGTGCAGCTCATCAddT |
| SMDCR0166 | 433 | GTTGAGCAGGTACGGGAGCCddA |
| WT Template (3' to 5') | 434 | GAGGTGGCACGTCGAGTAGTGCGTCGAGTACGGGAAGCCGACGGAGGACCTGATACAGGC--- |
| Mut Template (3' to 5') | 435 | GAGGTGGCACGTCGAGTAGTACGTCGAGTACGGGAAGCCGACGGAGGACCTGATACAGGC--- |

The invention claimed is:

1. A method of amplifying a target nucleic acid, wherein the method comprises:
   (a) providing a reaction mixture comprising: (i) a nucleic acid sample comprising or suspected of comprising the target nucleic acid, (ii) at least 20 different types of primer pairs, wherein at least one primer of each type of primer pairs is complementary to a portion of the target nucleic acid, and each primer pair has two blocking primers comprising a blocking group capable of blocking polymerase extension, wherein the blocking group is 2', 3'-dideoxynucleotide and the blocking group is at 3' terminal of each blocking primer, (iii) nucleic acid polymerase, and (iv) de-blocking agent capable of enabling polymerization of the target nucleic acid by said nucleic acid polymerase using the blocking primers; and
   (b) incubating the reaction mixture under a condition for amplification of the target nucleic acid.

2. The method of claim 1, wherein the blocking primer is further modified to decrease the amplification of undesired nucleic acid.

3. The method of claim 2, wherein the modification is introduction of at least one mismatched nucleotide in the primer.

4. The method of claim 3, wherein the mismatched nucleotide is 3, 4, 5, 6, 7, 8, 9, 10, 11, 12, 13, 14, 15, 16 or 17 bp away from the nucleotide with the blocking group.

5. The method of claim 3, wherein the mismatched nucleotide base is located on the 5' side of the nucleotide with the blocking group.

6. The method of claim 2, wherein the modification is a modification to form an extra bridge connecting the 2' oxygen and 4' carbon of at least one nucleotide of the blocking primer.

7. The method of claim 1, wherein the reaction mixture comprises at least 30, 40, 50, 60, 70, 80, 90, 100, 120, 140, 160, 180, 200, 250, 300, 400, 500, 600, 700, 800, 900 or 1000 different types of primer pairs.

8. The method of claim 1, wherein the different types of primers pairs can complementarily bind to different target nucleic acids or different sequences in the same target nucleic acid.

9. The method of claim 1, wherein the target nucleic acid is double strand DNA ligated with single or double adaptor tags or single stranded DNA ligated with single adaptor tag.

10. The method of claim 1, wherein the target nucleic acid is double stranded DNA comprising single or double molecular index tag or single stranded DNA comprising single molecular index tag.

11. The method of claim 10, wherein the molecular index tag comprises unique identifier nucleic acid sequence and an adaptor tag.

12. The method of claim 1, wherein the primers have common tailing sequence at or near 5' terminal of the primers.

13. The method of claim 12, wherein the common tailing sequence can be used as molecular index tag, sample index tag or adaptor tag or combinations of three tags.

14. The method of claim 1, wherein the nucleic acid other than the target nucleic acid is not amplified in step (b) substantially.

15. The method of claim 1, wherein the method is used for selective enrichment of mutant nucleic acid in a sample comprising wildtype nucleic acid.

16. The method of claim 15, wherein at least one blocking primer is complementary to the mutant nucleic acid at the mutant residues and the nucleotide of the blocking primer corresponding to a mutant residue has the blocking group.

17. A method of sequencing a target nucleic acid, wherein the method comprises:
(a) providing a reaction mixture comprising: (i) a nucleic acid sample comprising or suspected of comprising the target nucleic acid, (ii) at least 20 different types of primer pairs, wherein at least one primer of each type of primer pairs is complementary to a portion of the target nucleic acid, and each primer pair has two blocking primers comprising a blocking group capable of blocking polymerase extension, wherein the blocking group is 2', 3'-dideoxynucleotide and the blocking group is at 3' terminal of each blocking primer, (iii) nucleic acid polymerase, and (iv) de-blocking agent capable of enabling polymerization of the target nucleic acid by said nucleic acid polymerase using the blocking primers;
(b) incubating the reaction mixture under a condition for amplification of the target nucleic acid;
(c) adding adaptor tag, molecular index tag and/or sample index tag to the reaction products obtained from step (b); and
(d) determining the sequence of the reaction products obtained from step (c).

\* \* \* \* \*